US012168061B2

(12) United States Patent
Wang et al.

(10) Patent No.: US 12,168,061 B2
(45) Date of Patent: *Dec. 17, 2024

(54) ANTIBODY AGAINST GLYPICAN-3 AND APPLICATION THEREOF

(71) Applicant: CRAGE MEDICAL CO., LIMITED, Hong Kong (CN)

(72) Inventors: Huamao Wang, Shanghai (CN); Bo Song, Shanghai (CN)

(73) Assignee: CRAGE MEDICAL CO., LIMITED, Hongkong (CN)

(*) Notice: Subject to any disclaimer, the term of this patent is extended or adjusted under 35 U.S.C. 154(b) by 15 days.

This patent is subject to a terminal disclaimer.

(21) Appl. No.: 15/750,271

(22) PCT Filed: Aug. 2, 2016

(86) PCT No.: PCT/CN2016/092833
§ 371 (c)(1),
(2) Date: Feb. 5, 2018

(87) PCT Pub. No.: WO2017/020812
PCT Pub. Date: Feb. 9, 2017

(65) Prior Publication Data
US 2019/0046659 A1  Feb. 14, 2019

(30) Foreign Application Priority Data

Aug. 3, 2015 (CN) .......................... 201510481235.1

(51) Int. Cl.
| | | |
|---|---|---|
| C07K 16/30 | (2006.01) | |
| A61K 35/17 | (2015.01) | |
| A61K 39/00 | (2006.01) | |
| A61K 39/395 | (2006.01) | |
| A61K 47/68 | (2017.01) | |
| A61K 48/00 | (2006.01) | |
| C07K 14/705 | (2006.01) | |
| C07K 14/715 | (2006.01) | |
| C07K 14/725 | (2006.01) | |
| C07K 16/28 | (2006.01) | |
| C07K 16/46 | (2006.01) | |
| C07K 19/00 | (2006.01) | |
| C12N 5/10 | (2006.01) | |
| C12N 15/62 | (2006.01) | |
| C12N 15/63 | (2006.01) | |
| G01N 33/574 | (2006.01) | |

(52) U.S. Cl.
CPC .......... *A61K 47/6879* (2017.08); *A61K 35/17* (2013.01); *A61K 39/0011* (2013.01); *A61K 39/395* (2013.01); *A61K 48/00* (2013.01); *C07K 14/7051* (2013.01); *C07K 14/70517* (2013.01); *C07K 14/70521* (2013.01); *C07K 14/7151* (2013.01); *C07K 16/2809* (2013.01); *C07K 16/30* (2013.01); *C07K 16/303* (2013.01); *C07K 16/46* (2013.01); *C07K 19/00* (2013.01); *C12N 5/10* (2013.01); *C12N 15/62* (2013.01); *C12N 15/63* (2013.01); *A61K 2039/5156* (2013.01); *C07K 2317/21* (2013.01); *C07K 2317/24* (2013.01); *C07K 2317/31* (2013.01); *C07K 2317/565* (2013.01); *C07K 2317/73* (2013.01); *C07K 2317/92* (2013.01); *C07K 2319/03* (2013.01); *C07K 2319/33* (2013.01); *G01N 33/57438* (2013.01)

(58) Field of Classification Search
CPC ..... C07K 16/30; C07K 19/00; C07K 14/7051
See application file for complete search history.

(56) References Cited

U.S. PATENT DOCUMENTS

| | | | | |
|---|---|---|---|---|
| 7,883,853 B2 * | 2/2011 | Filmus | ................. | C07K 16/303 |
| | | | | 435/7.1 |
| 2004/0236080 A1 * | 11/2004 | Aburatani | .............. | C07K 16/18 |
| | | | | 530/388.26 |

FOREIGN PATENT DOCUMENTS

| | | |
|---|---|---|
| CN | 1842540 | 10/2006 |
| CN | 1842540 B | 7/2012 |
| CN | 103596985 | 2/2014 |
| CN | 103833852 | 6/2014 |
| EP | 2995682 A1 | 3/2016 |
| WO | 2008021156 A2 | 2/2008 |
| WO | 2009012394 A1 | 1/2009 |
| WO | 2012145469 A1 | 10/2012 |
| WO | 2013070468 A1 | 5/2013 |
| WO | 2014180306 A1 | 11/2014 |
| WO | WO2017/186121 | * 11/2017 |

OTHER PUBLICATIONS

Paul (Fundamental Immunology, 3rd Edition, 1993, pp. 292-295) (Year: 1993).*
Bendig M. M. (Methods: A Companion to Methods in Enzymology, 1995; 8:83-93) (Year: 1995).*
Rudikoff et al. (Proceedings of the National Academy of Sciences USA, vol. 79, p. 1979-1983, 1982) (Year: 1982).*
Wall et al. (Theriogenology, vol. 45, p. 57-68, 1996) (Year: 1996).*
Houdebine et al. (Journal of Biotechnology, vol. 34, p. 269-287, 1994) (Year: 1994).*
Kappell et al. (Current Opinions in Biotechnology, vol. 3, p. 548-553, 1992) (Year: 1992).*
Houdebine (Comparative Immunology, Microbiology, and Infectious Diseases, vol. 32, p. 107-121, 2009) (Year: 2009).*
International Search Report for international appl. No. PCT/CN2016/092833, dated Oct. 27, 2016 (6 pages, Including English translation).
Li et al., "Validation of glypican-3-specific scFv isolated from paired display/secretory yeast display library", BMC Biotechnology, 2012, 12:23, 10 pages provided.

(Continued)

*Primary Examiner* — Michael Allen
(74) *Attorney, Agent, or Firm* — HSML P. C.

(57) ABSTRACT

The present invention provides an antibody against glypican-3 (GPC3) and application thereof, and the antibody comprises a single chain antibody and humanized antibody.

26 Claims, 3 Drawing Sheets
Specification includes a Sequence Listing.

(56) References Cited

OTHER PUBLICATIONS

Feng et al., "Glypican-3 Antibodies: A New Therapeutic Target for Liver Cancer", Elsevier, FEBS Letters, 2014, 588(2), 6 pages provided.
Grupp et al., "Adoptive Cellular Therapy", Cancer Immunology and Immunotherapy, Aug. 11, 2010, pp. 149-172.
Davies et al., "Combining CD19 Redirection and Alloanergization to Generate Tumor-Specific Human T Cells for Allogeneic Cell Therapy of B-Cell Malignancies", Cancer Res., Published May 2010, 18 pages provided.
The extended European search report issued in European Application No. 16832300.4, dated Feb. 25, 2019, 12 pages provided.
Grupp et al., "Adoptive Cellular Therapy", Cancer Immunology and Immunotherapy, published Aug. 11, 2010, 24 pages provided, discussed in specification.
Davies JK et al.,"Combining CD19 redirection and alloanergization to generate tumor-specific human T cells for allogeneic cell therapy of B-cell malignancies", downloaded from cancerres.aacrjournals. org, American Association for Cancer Research, Published Online First Apr. 27, 2010, 11 pages provided, discussed in specification.

\* cited by examiner

ANTIBODY AGAINST GLYPICAN-3 AND APPLICATION THEREOF

TECHNICAL FIELD

The present invention relates to the field of immunotherapy or diagnosis of tumor, and in particular, to antibodies that specifically recognize glypican-3 (GPC3) and uses thereof.

BACKGROUND

At present, adoptive immunotherapy based on immune effector cells has achieved some effects in some tumors, and this immunotherapy method can overcome the defects of antibody treatment, however the therapeutic effects in most tumors are still unsatisfactory [Grupp S A, et al. Adoptive cellular therapy. Curr Top Microbiol Immunol., 2011; 344: 149-72.]. In recent years, it was discovered that the recognition specificity of cytotoxic lymphocytes (CTLs) to target cells depends on T cell receptors (TCRs), scFv of antibodies against tumor cell associated antigens and intracellular signal-activating motifs of T lymphocyte receptor CD3ζ or FcεRIγ were fused to a chimeric antigen receptor (CAR), and T lymphocyte was genetically modified by the chimeric antigen receptors on its surface by means of, for example, lentivirus infection. Such CAR T lymphocytes are capable of selectively targeting T lymphocytes to tumor cells and specifically killing the tumor in a non-limiting manner by Major Histocompatibility Complex (MHC). CAR T lymphocyte is a new immunotherapy strategy in the field of tumor immunotherapy. When designing CAR-modified immune effector cells, especially T cells, the targeted antigen genes are in fact a crucial choice. Given the complexity of gene expressions in vivo and various uncontrollable factors, selection for suitable genes for a CAR is very difficult. Moreover, for many tumor-specific antigens, it is difficult to find a specific molecule directed against them and suitable for constructing CAR-modified immune effector cells.

Glypican-3 (GPC3, also known as DGSX, GTR2-2, MXR7, OCI-5, SDYS, SGB, SGBS or SGBS1) is a cell surface protein belonging to heparan sulfate proteoglycan family. GPC3 gene encodes a precursor core protein of about 70-kDa which is cleaved by furin to produce a soluble, blood-accessible, amino-terminal (N-terminal) peptide of about 40-kDa and a membrane bound carboxy-terminal (C-terminal) peptide containing about 2 heparan sulfate (HS) sugar chains of about 30-kDa. GPC3 proteins attach to the cell membrane via glycosylphosphatidylinositol (GPI) anchors.

GPC3 is highly expressed in fetal liver, while not in normal adult liver tissue, however its expression is restored in hepatocellular carcinoma and closely related to the development and progression of hepatocellular carcinoma. GPC3 is not only highly detected in early stage of hepatocellular carcinoma, but the detection rate is also increased with the development of liver cancer. GPC3 expression was not detected in liver adenocarcinoma, cholangiocarcinoma, liver metastases, and 12 common solid tumors and 21 non-hepatoma cell lines. In addition, GPC3 is also expressed in tumors such as melanoma, ovarian clear cell carcinoma, yolk sac tumor and neuroblastoma. GPC3 is considered as a candidate target for tumor immunotherapy in view of the high specific expression of GPC3 in tumors such as hepatocellular carcinoma and melanoma.

Although protocols for the detection of liver cancer using anti-GPC3 antibodies and antibody-dependent (ADCC) or complement-dependent (CDC) cytotoxicity assays using anti-GPC3 antibodies have been reported, there are currently no available anti-GPC3 antibodies. Only GC33 antibody discloded in CN200580000807.4 was in phase I of clinical research, while clinical application remains to unclear.

In addition, anti-GPC3 antibodies can be used not only as therapeutic antibodies but also as immunotherapies such as T lymphocytes for diagnosis and chimeric antigen receptor modification (CAR). Current research shows that different antibodies may have different immunogenicity, and such immunogenicity will lead to the therapeutic effects and side effects of an antibody or its derived therapeutic agent. For example, CAR T cells based on mouse anti-mesothelin antibodies can cause allergic reactions that affect their long-term survival in human body. In view of the above considerations, there is a need in the art for further optimization and preparation of new anti-GPC3 antibodies that have good tumor-killing activity and excellent clinical application prospects when applied in solid tumors, so that GPC3 antibodies can be effectively used in tumor diagnosis and treatment, and benefit patients.

SUMMARY OF THE INVENTION

It is an object of the present invention to provide anti-glypican-3 antibodies and uses thereof.

In the first aspect of the present invention, an antibody that specifically recognizes glypican-3 (GPC3) is provided, and the antibody has a light chain variable region and a heavy chain variable region, and CDR1 of the light chain variable region has an amino acid sequence selected from a group consisting of SEQ ID NO: 16, SEQ ID NO: 67, SEQ ID NO: 69;

CDR2 of the light chain variable region has an amino acid sequence selected from a group consisting of SEQ ID NO: 18, SEQ ID NO: 68, SEQ ID NO: 70;

CDR3 of the light chain variable region has the amino acid sequence: SEQ ID NO: 20;

CDR1 of the heavy chain variable region has an amino acid sequence selected from a group consisting of SEQ ID NO: 10, SEQ ID NO: 60, SEQ ID NO: 62, SEQ ID NO: 64;

CDR2 of the heavy chain variable region has an amino acid sequence selected from a group consisting of SEQ ID NO: 12, SEQ ID NO: 61, SEQ ID NO: 63, SEQ ID NO: 65, SEQ ID NO: 66, SEQ ID NO: 71;

CDR3 of the heavy chain variable region has an amino acid sequence selected from a group consisting of SEQ ID NO: 14, SEQ ID NO: 72.

In a preferred embodiment, the antibody comprises:

antibody (a) (P7D4), and its light chain variable region has CDR1 of SEQ ID NO: 16, CDR2 of SEQ ID NO: 18 and CDR3 of SEQ ID NO: 20, or its heavy chain variable region has CDR1 of SEQ ID NO: 10, CDR2 of SEQ ID NO: 12 and CDR3 of SEQ ID NO: 14;

antibody (b) (am4), and its light chain variable region has CDR1 of SEQ ID NO: 16, CDR2 of SEQ ID NO: 18 and CDR3 of SEQ ID NO: 20; or its heavy chain variable region has CDR1 of SEQ ID NO: 60, CDR2 of SEQ ID NO: 61 and CDR3 of SEQ ID NO: 14;

antibody (c) (am14), and its light chain variable region has CDR1 of SEQ ID NO: 16, CDR2 of SEQ ID NO: 18 and CDR3 of SEQ ID NO: 20, or its heavy chain variable region has CDR1 of SEQ ID NO: 62, CDR2 of SEQ ID NO: 63 and CDR3 of SEQ ID NO: 14;

antibody (d) (am20), and its light chain variable region has CDR1 of SEQ ID NO: 16, CDR2 of SEQ ID NO: 18 and CDR3 of SEQ ID NO: 20; or its heavy chain variable region has CDR1 of SEQ ID NO: 64, CDR2 of SEQ ID NO: 65 and CDR3 of SEQ ID NO: 14;

antibody (e) (am35), and its light chain variable region has CDR1 of SEQ ID NO: 67, CDR2 of SEQ ID NO: 68 and CDR3 of SEQ ID NO: 20; or its heavy chain variable region has CDR1 of SEQ ID NO: 10, CDR2 of SEQ ID NO: 66 and CDR3 of SEQ ID NO: 14;

antibody (f) (am42), and its light chain variable region has CDR1 of SEQ ID NO: 69, CDR2 of SEQ ID NO: 70 and CDR3 of SEQ ID NO: 20, or its heavy chain variable region has CDR1 of SEQ ID NO: 10, CDR2 of SEQ ID NO: 66 and CDR3 of SEQ ID NO: 14;

antibody (g) (T2-23), and its light chain variable region has CDR1 of SEQ ID NO: 16, CDR2 of SEQ ID NO: 70 and CDR3 of SEQ ID NO: 20, or its heavy chain variable region has CDR1 of SEQ ID NO: 10, CDR2 of SEQ ID NO: 71 and CDR3 of SEQ ID NO: 72;

antibody (h), which recognizes the same antigenic determinant as that recognized by the antibody according to any one of (a) to (g).

In another preferred embodiment, the antibody specifically recognizing glypican-3 (GPC3) may be single chain antibody (scFV), monoclonal antibody, domain antibody, Fab fragment, Fd fragment, Fv fragment, F (ab')$_2$ fragment and a derivative thereof, or other forms of antibody; preferably single chain antibody.

In another preferred embodiment, the antibody that specifically recognizes glypican-3 (GPC3) is humanized or fully fully humanized; preferably, fully fully humanized.

In another preferred embodiment, the amino acid sequence of the heavy chain variable region of antibody (a) (P7D4) is shown in positions 1-121 of SEQ ID NO: 4; or the amino acid sequence of the light chain variable region of the antibody is shown in positions 137-247 of SEQ ID NO: 4;

The amino acid sequence of the heavy chain variable region of antibody (b) (am4) is shown in positions 1-121 of SEQ ID NO: 25; or the amino acid sequence of the light chain variable region of the antibody is shown in positions 137-247 of SEQ ID NO: 25;

The amino acid sequence of the heavy chain variable region of antibody (c) (am14) is shown in positions 1-121 of SEQ ID NO: 27; or the amino acid sequence of the light chain variable region of the antibody is shown in positions 137-247 of SEQ ID NO: 27;

The amino acid sequence of the heavy chain variable region of the antibody (d) (am20) is shown in positions 1-121 of SEQ ID NO: 29; or the amino acid sequence of the light chain variable region of the antibody is shown in positions 137-247 of SEQ ID NO: 29;

The amino acid sequence of the heavy chain variable region of antibody (e) (am35) is shown in positions 1-121 of SEQ ID NO: 31; or the amino acid sequence of the light chain variable region of the antibody is shown in positions 137-247 of SEQ ID NO: 31;

The amino acid sequence of the heavy chain variable region of the antibody (f) (am42) is shown in positions 1-121 of SEQ ID NO: 33; or the amino acid sequence of the light chain variable region of the antibody is shown in positions 137-247 of SEQ ID NO: 33; or The amino acid sequence of the heavy chain variable region of antibody (g) (T2-23) is shown in positions 1-121 of SEQ ID NO: 35; or the amino acid sequence of the light chain variable region of the antibody is shown in positions 137-247 of SEQ ID NO: 35.

In another aspect of the present invention, an antibody that specifically recognizes glypican-3 (GPC3) is provided, which is a humanized monoclonal antibody comprising a heavy chain variable region and a light chain variable region. Its heavy chain variable region comprises: CDR1 of the amino acid sequence of SEQ ID NO: 73, CDR2 of the amino acid sequence of SEQ ID NO: 74 and CDR3 of the amino acid sequence of SEQ ID NO: 75; or its light chain variable region comprises CDR1 of the amino acid sequence of SEQ ID NO: 76, CDR2 of the amino acid sequence of SEQ ID NO: 77 and CDR3 of the amino acid sequence of SEQ ID NO: 78.

In a preferred embodiment, the antibody has a heavy chain variable region of the amino acid sequence of SEQ ID NO: 58 or a light chain variable region of the amino acid sequence of SEQ ID NO: 59.

In another aspect of the invention, a nucleic acid encoding any one of the preceding antibodies is provided.

In another aspect of the present invention, an expression vector comprising the nucleic acid is provided.

In another aspect of the present invention, a host cell comprising the expression vector or having the nucleic acid integrated into its genome is provided.

In another aspect of the invention, use of any one of the antibodies described above is provided for the preparation of a targeted drug, antibody-drug conjugate, or a polyfunctional antibody that specifically targets tumor cells expressing glypican-3; or for the preparation of a reagent for diagnosing a tumor expressing Glypican-3; or for the preparation of chimeric antigen receptor-modified immune cells.

In another aspect of the present invention, a multi-functional immunoconjugate is provided, comprising: any one of the antibodies described above; and a functional molecule linked thereto (including covalently linked, conjugated, attached, adsorbed); and the functional molecule is selected from a group consisting of a molecule targeting a tumor surface marker, a tumor-suppressing molecule, a molecule targeting a surface marker of an immune cell, or a detectable label.

In a preferred embodiment, in the multifunctional immunoconjugate, the molecule that targets a tumor surface marker is an antibody or ligand that binds to a tumor surface marker; or the tumor-suppressing molecule is an anti-tumor cytokine or anti-tumor toxin; and preferably, the cytokine includes, but are not limited to: IL-12, IL-15, IFN-beta and TNF-alpha.

In another preferred embodiment, the detectable label in the multi-functional immunoconjugate includes a fluorescent label and a chromogenic label.

In another preferred embodiment, in the multifunctional immunoconjugate, the antibody that binds to a tumor surface marker refers to an antibody that recognizes antigens other than glypican-3, wherein the other antigens include: EGFR, EGFRvIII, mesothelin, HER2, EphA2, Her3, EpCAM, MUC1, MUC16, CEA, Claudin 18.2, folate receptor, Claudin 6, WT1, NY-ESO-1, MAGE 3, ASGPR1 or CDH16.

In another preferred embodiment, in the multifunctional immunoconjugate, the molecule that targets the surface marker of the immune cell is an antibody that binds to T cell surface marker, which can form a T-cell-engaging bifunctional antibody with any one of the above described antibodies (bispecific T cell engager, BiTE).

In another preferred embodiment, in the multifunctional immunoconjugate, the antibody that binds to the immune cell surface marker is an anti-CD3 antibody.

In another preferred embodiment, the anti-CD3 antibody is a single chain antibody (scFV), a monoclonal antibody, a Fab fragment, an Fd fragment, an Fv fragment, an F(ab')₂ fragment and a derivative thereof, or an antibody of other form; preferably single chain antibody.

In another preferred embodiment, the anti-CD3 antibody is humanized, chimeric, fully human or murine.

In another preferred embodiment, the multifunctional immunoconjugate is a fusion peptide, and further comprises a linker peptide (linker) between any one of the above described antibodies and the functional molecule linked thereto.

In another preferred embodiment, the linker peptide has the sequence (GlyGlyGlyGlySer (SEQ ID NO: 99))n, where n is an integer from 1 to 5; more preferably, n=3.

In another preferred embodiment, the multi-functional immunoconjugate is administered in a form of polypeptide or in the manner of gene administration.

In another aspect of the invention, a nucleic acid encoding any one of the multi-functional immunoconjugates described above is provided.

In another aspect of the present invention, use of any one of the above described multi-functional immunoconjugates is provided, for the preparation of an antineoplastic agent or an agent for diagnosis of tumors that express Glypican-3; or for the preparation of chimeric antigen receptor-modified immune cells. Preferably, the immune cells include T lymphocyte, NK cell or NKT lymphocyte.

In another aspect of the present invention, a chimeric antigen receptor (CAR) comprising any one of the above described antibodies is provided, and the chimeric antigen receptor comprises: any one of the above described antibodies, a transmembrane region and an intracellular signal region, which are sequentially linked; and the intracellular signal region is selected from a group consisting of intracellular signal region sequences of CD3ζ, FcεRIγ, CD27, CD28, CD137, CD134, MyD88, CD40 or a combination thereof.

In another preferred embodiment, the transmembrane region in the chimeric antigen receptor comprises a transmembrane region of CD8 or CD28.

In another preferred embodiment, in the chimeric antigen receptor, the chimeric antigen receptor comprises the following sequentially connected antibody, a transmembrane region and an intracellular signal region: any one of the above described antibodies, CD8, and CD3ζ; any one of the above described antibodies, CD8, CD137 and CD3ζ; any one of the above described antibodies, the transmembrane region of CD28 molecule, the intracellular signaling region of CD28 molecule and CD3ζ; or any one of the above described antibodies, the transmembrane region of CD28 molecule, the intracellular signaling region of CD28 molecule, CD137 and CD3ζ.

In another preferred embodiment, in the chimeric antigen receptor, the antibody is a single chain antibody or a domain antibody. In another preferred embodiment, the chimeric antigen receptor comprises:
SEQ ID NO: 49 or the amino acid sequence shown in positions 22-346 thereof;
SEQ ID NO: 50 or the amino acid sequence shown in positions 22-447 thereof;
SEQ ID NO: 51 or the amino acid sequence shown in positions 22-491 thereof;
SEQ ID NO: 52 or the amino acid sequence shown in positions 22-494 thereof;
SEQ ID NO: 53 or the amino acid sequence shown in positions 22-536 thereof;
The amino acid sequence of SEQ ID NO: 85;
The amino acid sequence of SEQ ID NO: 86; or
The amino acid sequence of SEQ ID NO: 87.

In another aspect of the invention, a nucleic acid encoding the chimeric antigen receptor is provided. In another preferred embodiment, the nucleic acid encoding the chimeric antigen receptor comprises:
SEQ ID NO: 44 or the nucleotide sequence shown in positions 380-1420 or 443-1420;
SEQ ID NO: 45 or the nucleotide sequence shown in positions 380-1723 or 443-1723;
SEQ ID NO: 46 or the nucleotide sequence shown in positions 380-1855 or 443-1855;
SEQ ID NO: 47 or the nucleotide sequence shown in positions 380-1864 or 443-1864;
SEQ ID NO: 48 or the nucleotide sequence shown in positions 380-1990 or 443-1990;
The nucleotide sequence of SEQ ID NO: 85;
The nucleotide sequence of SEQ ID NO: 87; or
The nucleotide sequence of SEQ ID NO: 89.

In another aspect of the present invention, an expression vector comprising a nucleic acid encoding the chimeric antigen receptor is provided. In another preferred embodiment, the expression vector is derived from lentiviral plasmid pWPT (or pWPT-eGFP).

In another aspect of the present invention, a virus comprising said vector is provided.

Use of the chimeric antigen receptor, or a encoding nucleic acid thereof, or a expression vector or virus comprising the nucleic acid for the preparation of genetically modified immune cells targeting the tumor that expresses Glypican-3 is provided.

In another preferred embodiment, the tumor expressing glypican-3 includes (but is not limited to) liver cancer, melanoma, ovarian clear cell carcinoma, yolk sac tumor and neuroblastoma.

In another aspect of the present invention, a genetically modified immune cell is provided, which is transduced with a nucleic acid encoding the chimeric antigen receptor or an expression vector or a virus containing the nucleic acid; or has the chimeric antigen receptor expressed on its surface.

In another preferred embodiment, the immune cells further carry an exogenous encoding sequence for cytokines; and preferably, the cytokines include IL-12, IL-15 or IL-21.

In another preferred embodiment, the immune cell also expresses another chimeric antigen receptor which does not contain CD3ζ but contains the intracellular signaling domain of CD28, the intracellular signaling domain of CD137, or a combination of both.

In another preferred embodiment, the immune cell further expresses a chemokine receptor; and preferably, the chemokine receptor includes: CCR2.

In another preferred embodiment, the immune cell further expresses siRNA which can reduce expression of PD-1 or a protein which blocks PD-L1.

In another preferred embodiment, the immune cell further expresses a safety switch; and preferably, the safety switch includes iCaspase-9, Truancated EGFR or RQR8.

In another preferred embodiment, the immune cells include T lymphocytes, NK cells or NKT cells.

In another aspect of the invention, use of the genetically modified immune cells is provided for the preparation of a tumor-inhibiting drug, and the tumor is a tumor expressing glypican-3.

In another aspect of the invention, a pharmaceutical composition (including a medicament or diagnostic reagent) is provided, comprising:
any one of the above described antibodies or a nucleic acid encoding the antibody; or any one of the above described immunoconjugates or a nucleic acid encoding the conjugate; or any one of the above described chimeric antigen receptors or a nucleic acid encoding the chimeric antigen receptor; or any one of the above described genetically modified immune cells.

Other aspects of the invention will be apparent to those skilled in the art from the disclosure herein.

MODES FOR CARRYING OUT THE INVENTION

Figure 1:
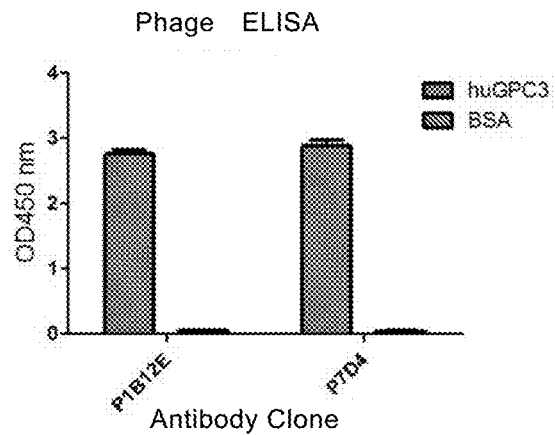
FIG. 1 shows binding of antibodies P1B12E and P7D4 to human GPC3 and control BSA in a single phage ELISA assay. The values for antibodies P1B12E and P7D4 to human GPC3 and negative control BSA demonstrate that the two selected antibodies can specifically bind to human GPC3.

After intensive research and screening, the inventors obtained antibodies that specifically recognize GPC3, including single chain antibodies and humanized antibodies. The antibody of the present invention can be used to prepare various targeting-antitumor drugs and drugs for diagnosing tumors.

Anti-GPC3 Antibody

Specific antibodies with good binding properties to GPC3 were screened and obtained in all-human natural antibody libraries by the present inventors, and further subjected to amino acid mutations to obtain anti-GPC3 antibodies with significantly increased affinity, and key CDR regions for them to exert their binding properties were also found by the inventors.

The present inventors also obtained a mouse antibody against GPC3 using hybridoma technique, humanized it, and obtained a humanized anti-GPC3 antibody through repeated comparison with extremely excellent binding property to GPC3 and key CDR regions for its binding performance were also found.

Antibodies of the invention may be intact immunoglobulin molecules or antigen-binding fragments including but not limited to Fab fragments, Fd fragments, Fv fragments, F(ab')$_2$ fragments, complementarity determining region (CDR) fragments, single chain antibody (scFv), domain antibody, bivalent single chain antibody, single chain phage antibody, bispecific diabody, triple chain antibody, quadruple chain antibody.

The antigen-binding properties of an antibody can be described by three specific regions located in variable regions of the heavy and light chains, termed complementarity determining regions (CDRs), which divide the variable regions into four framework regions (FR), and the amino acid sequences of four FRs are relatively conservative, not directly involved in binding reaction. These CDRs form a loop structure, in which β-folds formed by the FRs are located close to each other in space and the antigen binding site of the antibody is constituted by CDRs on the heavy chain and CDRs on the corresponding light chain. It is possible to determine which amino acids make up FR or CDR regions by comparing the amino acid sequences of the same type of antibody. The CDR regions are sequences of immunologically interesting proteins and the CDR regions of the antibodies of the invention are brand new. The antibody may comprise two, three, four, five, or all six of the CDR regions disclosed herein.

Another aspect of the invention includes functional variants of the antibodies described herein. If the variant is capable of competing with the parental antibody for specific binding to GPC3 and its ability to recognize GPC3 expressed on the surface of tumor cells is close to that of the specific antibodies provided in Examples of the present invention. The functional variants may have conservative sequence modifications, including nucleotide and amino acid substitutions, additions and deletions. These modifications can be introduced by standard techniques known in the art, such as directed mutagenesis and random PCR-mediated mutagenesis, and can include both natural and non-natural nucleotides and amino acids. Preferably, modification of the sequence occurs on a region outside the CDR region of the antibody.

Immunoconjugate

In the present invention, a multifunctional immunoconjugate is also provided, comprising the antibodies described herein and further comprising at least one functional molecule of other type. The functional molecule is selected from, but not limited to, a molecule that targets a tumor surface marker, a tumor-suppressing molecule, a molecule that targets a surface marker of an immune cell, or a detectable label. The antibody and the functional molecule may form a conjugate by covalent attachment, coupling, attachment, cross-linking, or the like.

As a preferred mode, the immunoconjugate may comprise an antibody of the invention and at least one molecule that targets a tumor surface marker or a tumor-suppressing molecule. The tumor-suppressing molecule may be anti-tumor cytokines or anti-tumor toxins. Preferably, the cytokines include but are not limited to IL-12, IL-15, IFN-beta, TNF-alpha. The molecules that target tumor surface markers, for example, can act synergistically with the antibodies of the invention to more precisely target tumor cells.

As a preferred mode, the immunoconjugate may comprise an antibody of the present invention and a detectable label. Such detectable labels include, but are not limited to, fluorescent labels, chromogenic labels such as enzymes, prosthetic groups, fluorescent materials, luminescent materials, bioluminescent materials, radioactive materials, positron-emitting metals and non-radioactive paramagnetic metal ion. More than one marker can also be included. The label used to label the antibody for the purpose of detection and/or analysis and/or diagnosis depends on the used particular detection/analysis/diagnosis technique and/or method, eg, immunohistochemical staining (tissue) samples, flow cytometry, and the like. Suitable labels for detection/analysis/diagnosis techniques and/or methods known in the art are well known to those skilled in the art.

As a preferred mode, the immunoconjugate may comprise an antibody of the invention as well as a molecule that targets a surface marker of an immune cell. The molecule that targets surface markers of immune cells can recognize immune cells and carry the antibodies of the invention to the immune cells, so that the antibodies of the invention can target the immune cells to the tumor cells and thus trigger immunocyte for specifically killing tumor.

As a means of chemically generating an immunoconjugate by conjugation, either directly or indirectly (eg, by a linker), the immunoconjugate can be produced as a fusion protein comprising an antibody of the invention and other suitable proteins. The fusion protein can be produced by a method known in the art, for example recombinantly produced by constructing and subsequently expressing the nucleic acid molecule which comprises the nucleotide sequence encoding the antibody in frame with a nucleotide sequence encoding a suitable label.

In another aspect of the invention, a nucleic acid molecule encoding at least one antibody of the invention, a functional variant, or an immunoconjugate thereof is provided. Once obtaining the relevant sequence, the recombination method can be used to obtain the relevant sequence in large quantities. This is usually done by cloning it into a vector, transferring it to a cell, and then isolating the relevant sequence from the proliferating host cells by conventional methods.

The present invention also relates to vectors comprising the appropriate DNA sequences described above as well as appropriate promoters or control sequences. These vectors can be used to transform an appropriate host cell to enable expression of the protein. The host cell may be a prokaryotic cell, such as a bacterial cell; or a lower eukaryotic cell, such as a yeast cell; or a higher eukaryotic cell, such as a mammalian cell.

Chimeric Antigen Receptor and Genetically Modified Immune Cell

In the present invention, a chimeric antigen receptor expressed on the surface of an immune effector cell (immune cell) is provided, wherein the chimeric antigen receptor comprises sequentially linked: extracellular binding region, transmembrane region and intracellular signal region, and the extracellular binding region comprises the antibody of the invention. By expressing the chimeric antigen receptor on the surface of immune effector cells, immune effector cells can have a highly specific cytotoxic effect on tumor cells that express GPC3.

As used herein, "immune cells" and "immune effector cells" are used interchangeably and include: T lymphocytes, NK cells or NKT cells, and the like; and preferably, NK cells and T lymphocytes.

As a preferred embodiment of the present invention, the antibody contained in the chimeric antigen receptor is a single chain antibody, which is connected to CD8 or the transmembrane region of CD28 through the hinge region of CD8, and the transmembrane region is immediately followed by the intracellular signal region.

The invention also includes nucleic acids encoding the chimeric antigen receptors. The present invention also relates to variants of the above described polynucleotides, which encode a polypeptide, or a fragment, analog and derivative of the polypeptide having the same amino acid sequence as the present invention.

The transmembrane region of the chimeric antigen receptor may be selected from the transmembrane region of a protein such as CD8 or CD28. The human CD8 protein is a heterodimer composed of two chains, $\alpha\beta$ or $\gamma\delta$. In one embodiment of the invention, the transmembrane region is selected from the transmembrane region of CD8a or CD28. In addition, the CD8α hinge is a flexible region so that CD8 or CD28 and the transmembrane region as well as the hinge region are used to connect the target recognition domain scFv of the chimeric antigen receptor CAR to the intracellular signal region.

The intracellular signal region may be selected from a group consisting of intracellular signal region of CD3ζ, FcεRIγ, CD27, CD28, CD137, CD134, MyD88, CD4 protein, and combinations thereof. The CD3 molecule consists of five subunits, in which CD3ζ subunit (also known as CD3 zeta, abbreviated as Z) contains 3 ITAM motifs that are important signal transduction regions in TCR-CD3 complex. CD3δZ is a truncated CD3ζ sequence without ITAM motif and is generally constructed in the present invention as a negative control. FcεRIγ is mainly distributed on the surface of mast cells and basophils, which contains an ITAM motif, which is similar to CD3ζ in structure, distribution and function. In addition, as mentioned above, CD28, CD137 and CD134 are co-stimulatory signaling molecules. The co-stimulatory effect of their intracellular signaling segments upon binding to the respective ligands results in the continued proliferation of immune effector cells, primarily T lymphocytes, and increase in the level of cytokines such as IL-2 and IFN-γ secreted by immune effector cells, and the survival period and anti-tumor effect of CAR immune effector cells in vivo are increased.

The chimeric antigen receptor of the present invention can be sequentially linked as follows:

The antibody of the invention, CD8 and CD3ζ;

The antibody of the invention, CD8, CD137 and CD3ζ;

The antibody of the invention, the transmembrane region of CD28 molecule, the intracellular signal region of CD28 molecule and CD3ζ; or The antibodies of the invention, the transmembrane region of CD28 molecule, the intracellular signal region of CD28 molecule, CD137 and CD3ζ.

And combinations thereof, wherein CD28a in the relevant chimeric antigen receptor protein represents the transmembrane region of CD28 molecule and CD28b represents the intracellular signal region of CD28 molecule. The various chimeric antigen receptors described above are collectively referred to as scFv (GPC3)-CAR.

The present invention also provides a vector comprising the above-mentioned nucleic acid encoding a chimeric antigen receptor protein expressed on the surface of an immune effector cell. In a specific embodiment, the vector used in the present invention is a lentiviral plasmid vector pWPT-eGFP. This plasmid belongs to the third generation of self-inactivating lentiviral vector system. The system has three plasmids, packaging plasmid psPAX2 encoding protein Gag/Pol, encoding Rev protein; envelope plasmid PMD2.G encoding VSV-G protein; and empty vector pWPT-eGFP, which can be used for recombinant introduction of a nucleic acid sequence of interest, i.e., a nucleic acid encoding CAR. In the empty vector pWPT-eGFP, the expression of enhanced green fluorescent protein (eGFP) is regulated by elongation factor-1α (EF-1α) promoter. While in the recombinant expression vector pWPT-eGFP-F2A-CAR containing the nucleic acid sequence encoding CAR, co-expression of eGFP and CAR is achieved by ribosomal skipping sequence 2A (abbreviated as F2A) from food-and-mouth disease virus (FMDV).

The invention also includes viruses comprising the vectors described above. The viruses of the invention include packaged infectious viruses as well as viruses to be packaged that contain the necessary components for packaging into infectious viruses. Other viruses known in the art that can be used to transduce exogenous genes into immune effector cells and their corresponding plasmid vectors are also useful in the present invention.

The present invention further includes a genetically modified T lymphocyte, which is transduced with a nucleic acid of the present invention or transduced with the above-mentioned recombinant plasmid containing the nucleic acid of the present invention or a viral system containing the plasmid. Conventional nucleic acid transduction methods in the art, including non-viral and viral transduction methods, can be used in the present invention. Non-viral transduction methods include electroporation and transposon methods. Recently, nucleofector nuclear transfection instrument developed by Amaxa can directly introduce foreign genes into nucleus to achieve highly efficient transduction of target genes. In addition, compared with conventional electroporation, the transduction efficiency of transposon system based on Sleeping Beauty system or PiggyBac transposon was significantly improved. The combination of nucleofector transfection instrument and SB Sleeping Beauty transposon system has been reported [Davies J K., et al. Combining CD19 redirection and alloanergization to generate tumor-specific human T cells for allogeneic cell therapy of B-cell malignancies. Cancer Res, 2010, 70(10): OF1-10.], and high transduction efficiency and site-directed integration of target genes can be achieved by this method. In one embodiment of the invention, the transduction method of a T lymphocyte modified by a chimeric antigen receptor gene is a transduction method based on a virus such as a retrovirus or a lentivirus. The method has the advantages of high transduction efficiency and stable expression of exogenous gene, and the time for in vitro culturing T lymphocytes to clinical level can be shorten. The transduced nucleic acid is expressed on the surface of the transgenic T lymphocytes by transcription, translation. In vitro cytotoxicity assay performed on various cultured tumor cells demonstrated that the immune effector cells of the present invention have highly specific tumor cell killing effects (also known as cytotoxicity). Therefore, the nucleic acid encoding a chimeric antigen receptor protein of the present invention, a plasmid comprising the nucleic acid, a virus comprising the plasmid, and a transgenic immune effector cells transfected with the nucleic acid, plasmid or virus described above can be effectively used in tumor immunotherapy.

The immune cells of the present invention may also carry exogenous encoding sequences for cytokines, including but not limited to IL-12, IL-15 or IL-21. These cytokines have immunomodulatory or antitumor activity, enhance the function of effector T cells and activated NK cells, or directly exert anti-tumor effects. Therefore, those skilled in the art will understand that the use of these cytokines will help the immune cells to function better.

In addition to the chimeric antigen receptor described above, the immune cells of the present invention may also express another chimeric antigen receptor, which does not contain CD3ζ, but contains intracellular signaling domain of CD28 and intracellular signal domain of CD137, or a combination of both.

The immune cells of the present invention may also express chemokine receptors; the chemokine receptors include, but are not limited to, CCR2. A skilled person will understand that the CCR2 chemokine receptor can competitively bind CCR2 in the body and is beneficial for blocking the metastasis of the tumor.

The immune cells of the present invention may also express siRNAs that can reduce PD-1 expression or PD-L1-blocking proteins. A skilled person will understand that competitive blocking of the interaction between PD-L1 and its receptor PD-1 will facilitate the recovery of anti-tumor T-cell responses, thereby inhibiting tumor growth.

The immune cells of the present invention may also express a safety switch; preferably, the safety switch includes iCaspase-9, Truancated EGFR or RQR8.

Pharmaceutical Composition

The antibodies, immunoconjugates comprising the antibodies, and genetically modified immune cells of the present invention can be used in the preparation of a pharmaceutical composition or diagnostic reagent. In addition to an effective amount of the antibody, immunological conjugate, or immune cell, the composition may further comprise a pharmaceutically acceptable carrier. The term "pharmaceutically acceptable" means that when the molecular entities and compositions are properly administered to animals or humans, they do not cause adverse, allergic or other untoward reactions.

Specific examples of some of the substances which may be used as pharmaceutically acceptable carriers or components thereof are sugars, such as lactose, dextrose and sucrose; starches, such as corn starch and potato starch; cellulose and its derivatives, such as carboxymethylcellulose sodium, ethylcellulose and methylcellulose; gum tragacanth; malt; gelatin; talc; solid lubricants such as stearic acid and magnesium stearate; calcium sulfate; vegetable oils, such as peanut oil, cottonseed oil, sesame oil, olive oil, corn oil and cocoa butter; polyhydric alcohols such as propylene glycol, glycerin, sorbitol, mannitol and polyethylene glycol; alginic acid; emulsifiers such as Tween®; wetting agents such as sodium lauryl sulfate; coloring agents; flavoring agents; tablets, stabilizers; antioxidants; preservatives; pyrogen-free water; isotonic saline solutions; and phosphate buffers and the like.

The composition of the present invention can be prepared into various dosage forms as needed, and the dosage to be administered to a patient can be determined by a physician according to factors, such as type, age, body weight, and general disease condition of a patient, mode of administration, and the like. For example, injection or other treatment may be used.

The present invention is further described below with reference to specific embodiments. It should be understood that these examples are only for illustrating the present invention and are not intended to limit the scope of the present invention. Experimental procedures in the following examples where no specific conditions are indicated are generally carried out in accordance with the conditions described in customary conditions such as those compiled by J. Sambrook et al., Molecular Cloning Experiments Guide, Third Edition, Science Press, 2002, or according to the manufacturer Suggested conditions.

Example 1. Preparation of a Specific Single Chain Antibody (scFv) Binding to Human GPC3

1.1 Screening of GPC3-Specific Binding Antibodies Based on Phage Display

Using phage display technology, human GPC3 (hereinafter referred to as huGPC3) specific antibody was screened from the all-human natural antibodies library. For this purpose, glycerol bacteria (purchased from Shanghai Rui Jin Biotechnology Co., Ltd.) from the natural library of phage-displayed all-human single-chain antibody were inoculated in 400 ml of 2×YT/ampicillin medium so that the cell density reached $OD_{600}$=0.1, and incubated at 37° C. and 200 rpm until cell density reached $OD_{600}$=0.5. Cells were infected with $10^{12}$ pfu of M13KO7 helper phage (purchased from Invitrogen) and incubated at 30° C. and 50 rpm for 30 minutes. After 50 mg/L kanamycin was added and shaking-culture was performed at 37° C. and 200 rpm for 30 minutes, the pellet was separated by centrifugation (15 minutes, 1600×g, 4° C.) and resuspended in 400 ml of 2×YT/Penicillin/kanamycin medium and shaken for 16 hours at 37° C. and 200 rpm. Finally, the pellet was separated by centrifugation (5000 rpm, 4° C. for 20 minutes) and discarded. The supernatant was filtered through a 0.45 μm filter and ¼ volume of 20% (w/v) PEG 8000, 2.5 M NaCl solution was added and incubated in an ice bath for 1 hour to precipitate bacteriophage pellets. The pellet was then percipitated by centrifugation (20 min, 8000×g, 4° C.) and the supernatant discarded. The phage were resuspended in 25 ml of prechilled PBS (137 mM NaCl, 2.7 mM KCl, 8 mM $Na_2HPO_4$, 2 mM $KH_2PO_4$) and centrifuged (5 minutes, 20000×g, 4° C.). ¼ volume of 20% (w/v) PEG8000, 2.5 M NaCl solution was added to the supernatant and incubated in an ice bath for 30 minutes to precipitate phage particles again. The pellets were centrifuged (30 min, 20000×g, 4° C.) and the phage pellets were resuspended in 2 ml of prechilled PBS again, kept on ice for 30 min and centrifuged (30 min, 17000×g, 4° C.). Supernatants were mixed with 4% (w/v) BSA in PBS at 1:1, placed on a rotary mixer and incubated for 30 minutes at room temperature before being directly used for screening.

Using the above phage antibody library, four rounds of directional screening were performed on biotinylated human GPC3 recombinant protein (purchased from Shanghai Rui Jin Biotechnology Co., Ltd.) with the following scheme: The phage antibody library was incubated with biotin-labeled antigen GPC3 at room temperature for 2 hours and then incubated with streptavidin magnetic beads MyOne Cl (from Invitrogen) blocked with 2% (w/v) BSA (bovine serum albumin, purchased from Shanghai Bioengineering) at room temperature for 30 minutes. The beads were then washed with PBST (containing 0.1% Tween-20) buffer to remove phages which were not specifically bound or with weak binding capacities. Strongly-binding phages were then eluted from magnetic beads with glycine-HCl (pH 2.2), neutralized with Tris neutralizing solution (pH 9.1), and used to infect E. coli ER2738 in the mid-logarithmic growth phase and for the next round of screening. In the four rounds of screening, the beads were used in an amount of 50 μl, 20 μl, 10 μl and 10 μl, and the concentrations of biotin-labeled antigen GPC3 were 200 nM, 10 nM, 5 nM and 1 nM, respectively, and the time for PBST-washing was 10, 10, 15 and 20, respectively.

1.2 Identification of GPC3-Specific Binding Antibodies 96 clones were randomly selected in the clones obtained from the fourth round of screening and their binding capability to human GPC3 was analyzed by single phage ELISA (enzyme-linked immunosorbent assay). For this purpose, each single colony was inoculated in 300 μl of 2×YT/ampicillin medium (containing 2% glucose) in a 96-well deep-well plate and cultured with shaking at 37° C. and 250 rpm for 16 hours. 20 μl of culture was inoculated into 500 μl of 2×YT/ampicillin medium (containing 0.1% glucose) and shaken at 37° C. and 250 rpm for 1.5 hours. To prepare the helper phage solution, 75 μl of M13KO7 (titer of $3 \times 10^{12}$ pfu/ml) was taken and mixed into 15 ml of 2×YT medium and added into a culture plate at 50 μl/well, and incubated at 37° C. and 150 rpm for 30 minutes. And then prepared kanamycin solution (180 μl of 50 mg/ml kanamycin was taken and added into 15 ml of 2×YT medium) was added at 50 μl/well and incubated with shaking for 16 hours at 37° C. and 250 rpm. Finally, cells were precipitated by centrifugation (30 mins, 5000×g, 4° C.) and the supernatant was transferred to a new 96-well deep-well plate.

For single phage ELISA, 100 ng/well of antigen GPC3 and negative control protein BSA (100 μl/well) were used in a 96-well MediSorp ELISA plate (purchased from Nunc) and coated overnight at 4° C. Each well was blocked with PBST containing 2% BSA (w/v). The wells were then washed with PBST for three times and PBST was discarded. Then, each phage solution prepared above was added into each well of the plate at 100 μl/well. After incubated at 37° C. for 2 hours, the plate was washed for three times with PBST. To detect bound phage, anti-M13 antibody peroxide dismutase conjugate (purchased from GE Healthcare) was diluted at 1:5000 in PBST and 100 μl was taken and added into each well. After incubated at 37° C. for 1 hour, the wells were rinsed for three times with PBST and then rinsed for three times with PBS. Finally, 50 μl of TMB substrate was pipetted into the wells and developed for 10 minutes at room temperature, followed by addition of 50 μl of 2M $H_2SO_4$ per well to quench the color reaction. Extinction values were measured at 450 nm with an enzyme-linked immunosorbent (Bio-Rad).

Two different single chain antibodies P1B12E (SEQ ID NO: 1 (nucleotide), 2 (amino acid)) and P7D4 (SEQ ID NO: 3 (nucleotide), 4 (amino acid)) were observed with sequencing analysis, which exhibited significantly stronger binding signal to human GPC3 (huGPC3) in ELISA assay, while not binding to BSA (FIG. 1).

Example 2. Expression and Purification of Anti-GPC3 Single-Chain Antibody

According to the standard protocol, scFv-P1B12E fragment was amplified from the plasmid (pCantab 5E-P1B12E) of screened clone P1B12E using primer pair V5-P1B12E-F (SEQ ID NO: 5) and V5-P1B12E-R (SEQ ID NO: 6), and scFv-P7D4 fragment was amplified from the plasmid (pCantab 5E-P7D4) of screened clone p7D4 (pCantab 5E-P7D4) using primer pair V5-P7D4-F (SEQ ID NO: 7) and V5-P7D4-R (SEQ ID NO: 8), digested with NheI/BamHI (purchased from NEB) and connected to vector plasmid pCMV-V5-Fc (Fc fragment of human antibody IgG1 was fused and expressed downstream to the multiple cloning site of this vector, hereinafter referred to as V5-Fc, purchased from Shanghai Rui Jin Biotechnology Co., Ltd.) digested with NheI/BamHI using T4 DNA ligase (purchased from NEB) and was transformed into host strain TOP10. Clones were picked out and positive clones were identified by PCR and confirmed by sequencing, thereby obtaining V5-scFv-P1B12E-Fc and V5-scFv-P7D4-Fc eukaryotic expression plasmids, respectively.

Figure 2:
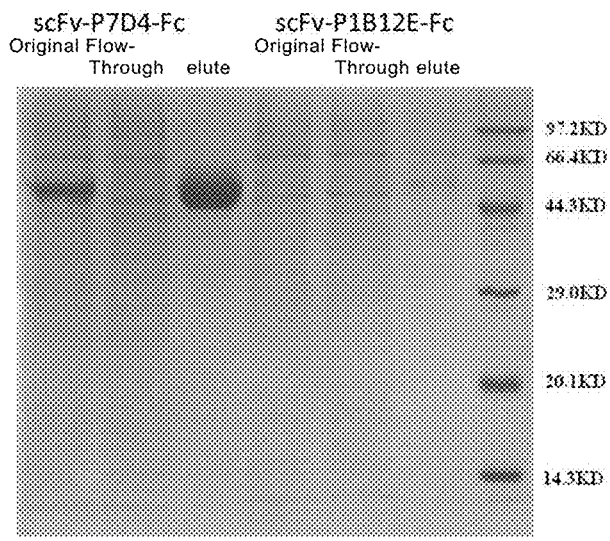
FIG. 2 shows purification electrophoresis of antibodies to human GPC3.

The above expression plasmids were respectively transfected into well-grown HEK-293F cells, which were cultured at 37° C., 5% $CO_2$, 125 rpm for 7 days and centrifuged at 4000 rpm for 10 mins. Pellets were removed, and the supernatant was collected and filtered with 0.45 μm membrane. Processed samples were affinity-purified with protein A (from GE) affinity column, and purified antibody-Fc fusion protein scFv-P1B12E-Fc and scFv-P7D4-Fc were finally obtained. The identification results are shown in FIG. 2, and their molecular weights are around 50 kD.

Example 3. Binding of Each Cell Line to Anti-GPC3 Single Chain Antibody Analyzed Through Flow Cytometry The ability of each of antibodies scFv-P1B12E-Fc and scFv-P7D4-Fc to bind to GPC3-positive hepatocarcinoma HepG2 cell line (ATCC) was analyzed by fluorescence activated cell sorter (FACS) (BD FACSCalibur).

Specific methods are as follows:

1) inoculating HepG2 hepatocarcinoma cell line in logarithmic growth phase into a 6 cm dish at inoculation cell density of about 90%, and incubating overnight at 37° C. in an incubator.

2) digesting cells with 10 mM EDTA, collecting cells through centrifugation at 200 g×5 mins, and resuspending cells in 1% phosphate buffered saline (NBS PBS) containing calf serum at $1×10^6$ to $1×10^7$/mL into a flow-specific tube in an amount of 100 μl per tube.

3) centrifuging at 200 g×5 min, and discarding the supernatant.

4) adding antibodies scFv-P1B12E-Fc and scFv-P7D4-Fc to be tested, respectively, while using PBS as a negative control. The final concentration of antibody is 10 μg/ml. 100 μl was added to each tube, and incubated in an ice bath for 45 minutes.

5). Adding 2 ml of 1% NBS PBS to each tube and centrifuging at 200 g×5 min for two times.

6) Discarding the supernatant and adding FITC fluorescently labeled goat anti-human antibody (Shanghai Kangcheng Bioengineering Co., Ltd.) at a dilution of 1:50 with 100 ul being added to each tube, incubating in an ice bath for 45 minutes.

7). Adding 2 ml of 1% NBS PBS into each tube, centrifuging at 200 g×5 min for two times.

8) Discarding the supernatant, resuspending in 300 ul of 1% NBS PBS and detecting by flow cytometry.

9). analyzing the data using flow cytometry data analysis software WinMDI 2.9.

Figure 3:
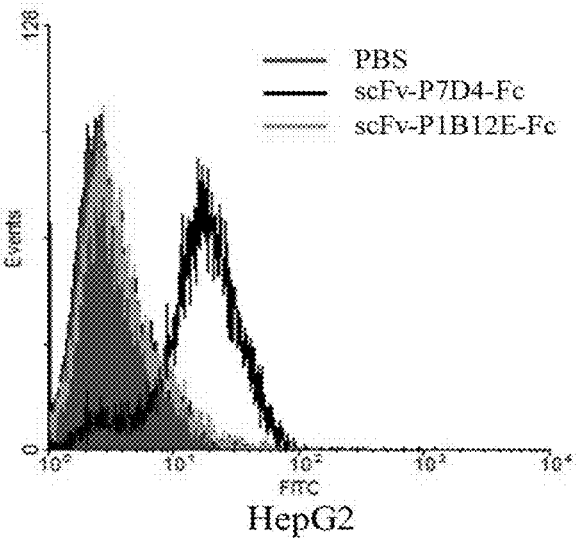
FIG. 3 shows binding activity analysis of antibodies scFv-P1B12E-Fc and scFv-P7D4-Fc to GPC3-expression positive HepG2 cells.

The results are shown in FIG. 3, and the results of flow cytometry showed that antibody scFv-P7D4-Fc can specifically recognize GPC3-expressing HepG2 cells, and antibody scFv-P1B12E-Fc did not bind to HepG2 cells.

Example 4. Screening and Preparation of P7D4 Single Chain Antibody Mutants with Increased GPC3 Binding Capacity For enhancing the ability of P7D4 single-chain antibody to bind to GPC3, some amino acids in its heavy chain CDR1 and CDR2 regions, or light chain CDR1 and CDR2 were randomly mutated and the corresponding affinity mature libraries H12 and L12 were constructed.

4.1 CDR ☒ P7D4 Light and Heavy Chains and CDR Regions Thereof

The nucleotide sequence of P7D4 scFv is shown as follows (SEQ ID NO: 3; wherein positions 76-105 is heavy chain CDR1, positions 148-198 is the heavy chain CDR2, positions 295-330 is heavy chain CDR3, positions 475-516 is light chain CDR1; positions 562-582 is light chain CDR2, positions 679-708 is light chain CDR3; wherein positions 1-363 is heavy chain nucleotide sequence, 409-741 is light chain nucleotide sequence, positions 364-408 is $(Gly_4Ser)_3$ linker).

CAGGTGCAGCTGCAGGAGTCCGGGGGAGGCTTAGTTCAGCCTGGGAGGTC

CCTGAGACTCTCCTGTGCAGCCTCTGGATTCACCTTCAGTAGCTATGCTA

TGCACTGGGTCCGCCAGGCTCCAGGCAAGGGGCTGGAGTGGGTCTCAGCT

ATTAGTGGTAGTGGTGGTAGCACATACTACGCAGACTCCGTGAAGGGCCG

GTTCACCATCTCCAGAGACAATTCCAAGAACACGCTGTATCTGCAAATGA

ACAGCCTGAGAGCCGAGGACACGGCCGTATATTACTGTGCGAAAGATCGA

CGAGGGAGCCACGCTGATGCTTTTGATGTCTGGGGCCAAGGAACCCTGGT

CACCGTCTCGAGT*GGTGGAGGCGGTTCAGGCGGAGGTGGTTCTGG*

*CGGTGGCGGATCG*CAGTCTGCCCTGACTCAGCCTCCCTCCGCGTCCGGG

TCTCCTGGACAGTCAGTCACCATCTCCTGCACTGGAACCAGCAGTGACGT

TGGTGGTTATAACTATGTCTCCTGGTACCAACAGTACCCAGGCAAAGCCC

CCAAACTCCTCATCTATGGTAACAGCAATCGGCCCTCAGGGGTCCCTGAC

CGATTCTCTGGCTCCAAGTCTGGCACCTCAGCCTCCCTGGCCATCACTGG

GCTCCAGGCTGAGGATGGGGCTGATTATTACTGCCAGTCCTATGACAGCA

GCCTGCGTGTGGTATTCGGCGGAGGGACCAAGGTCACCGTCCTAGGT

P7D4 scFv amino acid sequence
is shown as follows (SEQ ID NO: 4):

QVQLQESGGGLVQPGRSLRLSCAASGFTFSSYAMHWVRQAPGKGLEWVSA

ISGSGGSTYYADSVKGRFTISRDNSKNTLYLQMNSLRAEDTAVYYCAKDR

RGSHADAFDVWGQGTLVTVSS*GGGGSGGGGSGGGGS*QSALTQPPSASGS

PGQSVTISCTGTSSDVGGYNYVSWYQQYPGKAPKLLIYGNSNRPSGVPDR

FSGSKSGTSASLAITGLQAEDGADYYCQSYDSSLRVVFGGGTKVTVLG

P7D4 VH CDR1:
nucleotide sequence:
(SEQ ID NO: 9)
GGATTCACCTTCAGTAGCTATGCTATGCAC;

amino acid sequence:
(SEQ ID NO: 10)
GFTFSSYAMH.

P7D4 VH CDR2:
nucleotide sequence:
(SEQ ID NO: 11)
gctattagtggtagtggtggtagcacatactacgcagactccgtgaaggg
c;

-continued amino acid sequence:
(SEQ ID NO: 12)
AISGSGGSTYYADSVKG.

P7D4 VH CDR3:
nucleotide sequence:
(SEQ ID NO: 13)
gatcgacgagggagccacgctgatgcttttgatgtc;

amino acid sequence:
(SEQ ID NO: 14)
DRRGSHADAFDV.

P7D4 VL CDR1:
nucleotide sequence:
(SEQ ID NO: 15)
actggaaccagcagtgacgttggtggttataactatgtctcc;

amino acid sequence:
(SEQ ID NO: 16)
TGTSSDVGGYNYVS.

P7D4 VL CDR2:
nucleotide sequence:
(SEQ ID NO: 17)
ggtaacagcaatcggccctca;

amino acid sequence:
(SEQ ID NO: 18)
GNSNRPS.

P7D4 VL CDR3:
nucleotide sequence:
(SEQ ID NO: 19)
cagtcctatgacagcagcctgcgtgtggta;

amino acid sequence:
(SEQ ID NO: 20)
QSYDSSLRVV.

4.2 Construction of Affinity Mature Library of H12

By sequence alignment and analysis of P7D4 single-chain antibody, part of amino acids in the first and second CDR regions of P7D4 heavy chain were selected and randomized mutations were introduced by primers to construct a heavy chain affinity mature library.

To prepare a DNA fragment encoding the P7D4 mutant library, two DNA fragments were respectively obtained by PCR using plasmid pCantab P7D4 as a template, followed by splicing through bypass PCR method. Specifically, the following procedure was used: for synthesizing genes, PCR reactions were performed in a volume of 50 μl each using plasmid pCantab P7D4 as a template with a final concentration of 0.2 μM for each primer and 5 μl of 10×KOD Plus buffer, 4 μl dNTPs (dATP, dCTP, dGTP and dTTP, 2 mM each), 2 μl 25 mM MgSO$_4$ and 1 U KOD Plus (from Takara) were added and the PCR procedure was started in a thermal cycler after making up the volume with water. The reaction was firstly heated to 94° C. for 5 minutes and then incubated for 25 cycles of 94° C. for 30 seconds, 56° C. for 30 seconds and 68° C. for 30 seconds, and finally, at 68° C. for 10 minutes. The first fragment was amplified using primers S1
(SEQ ID NO: 21, CAACGTGAAAAAATTATTATTCGC)
and 74H12F1r
(SEQ ID NO: 22,
CCAGCCCCTTGCCTGGAGCCTGGCGGACCCAMNNCATAGCATAMNNACTG

AAGGTGAATCCAG)

and the second fragment was amplified using primer 74H12F2f (SEQ ID NO: 23,

GCTCCAGGCAAGGGGCTGGAGTGGGTCTCANNKATTAGTNNKNNKGNTNN

KNNKACATACTACGCAGACTCC)
and

S6
(SEQ ID NO: 21, GTAAATGAATTTTCTGTATGAGG).

Expected PCR products were identified by analytical agarose gel electrophoresis and purified from samples by Wizard SV Gel and PCR Clean-up Kit (available from Promega). The two fragments were added in equimolar ratio to a second round of bridge PCR as a template and the reaction system still used KOD Plus system mentioned above. The reaction was firstly heated to 94° C. for 5 minutes and then incubated for 10 cycles, each cycling reaction conditions were 94° C. for 30 seconds, 60° C. for 30 seconds and 68° C. for 30 seconds, and finally, at 68° C. for 10 minutes. Subsequently, primers S1 and S6 were directly added to the reaction system at a final concentration of 0.2 μM, and the PCR program was started. The reaction was firstly heated to 94° C. for 5 minutes and then incubated for 25 cycles of 94° C. for 30 seconds, 56° C. for 30 seconds and 68° C. for 30 seconds, and finally, at 68° C. for 10 minutes. The expected PCR products were separated by preparative agarose gel electrophoresis and purified by Wizard SV Gel and PCR Clean-up kits according to the manufacturer's instructions.

In the library, complete DNA fragments contained sfiI and NotI restriction enzyme recognition sites at each end, and was digested by restriction endonuclease sfiI/NotI for restriction digestion and inserted into phagemid vector pCANTAB 5E digested by the same two enzymes. Ligation products were isolated and desalted using Wizard SV Gel and PCR Clean-up Kit for electrotransformation. For electrotransformation, a home-made competent E. coli ER2738 (available from NEB) was used with electroporation cuvette and electroporation instrument Gene Pulser II (from Bio-Rad). A library containing 8.9×10$^9$ mutants was finally confirmed.

4.3 Construction of Affinity Mature Library of L12

By sequence alignment and analysis of P7D4 single-chain antibody, part of amino acids in the first and second CDR regions of P7D4 light chain were selected and randomized mutations were introduced by primers to construct a light chain affinity mature mutant library.

To prepare a DNA fragment encoding the P7D4 mutant library, two DNA fragments were respectively obtained by PCR using plasmid pCantab P7D4 as a template, followed by splicing through bypass PCR method. Specifically, the following procedure was used: for synthesizing genes, PCR reactions were performed in a volume of 50 μl each using plasmid pCantab P7D4 as a template with a final concentration of 0.2 μM for each primer and 5 μl of 10×KOD Plus buffer, 4 μl dNTPs (dATP, dCTP, dGTP and dTTP, 2 mM each), 2 μl 25 mM MgSO$_4$ and 1 U KOD Plus were added and the PCR procedure was started in a thermal cycler after making up the volume with water. The reaction was firstly heated to 94° C. for 5 minutes and then incubated for 25 cycles of 94° C. for 30 seconds, 56° C. for 30 seconds and 68° C. for 30 seconds, and finally, at 68° C. for 10 minutes. The first fragment was amplified using primers S1 and 74L12F1r
(SEQ ID NO: 83,
GTTTGGGGGCTTTGCCTGGGTACTGTTGGTACCAGGAGACMNNAHNMNNA

HNACCAACGTCACTGCTG)

and the second fragment was amplified using primer

74L12F2f
(SEQ ID NO: 84, ACCCAGGCAAAGCCCCCAAACTCCTCATCTATNN

KNNKNNKNNKCGGCCCTCAGGGGTC)
and

S6.

Expected PCR products were identified by analytical agarose gel electrophoresis and purified from samples by Wizard SV Gel and PCR Clean-up Kit. The two fragments were added in equimolar ratio to a second round of bridge PCR as a template and the reaction system still used KOD Plus system mentioned above. In the absence of primers, the reaction was firstly heated to 94° C. for 5 minutes and then incubated for 10 cycles, each cycling reaction conditions were 94° C. for 30 seconds, 60° C. for 30 seconds and 68° C. for 30 seconds, and finally, at 68° C. for 10 minutes. Subsequently, primers S1 and S6 were directly added to the reaction system at a final concentration of 0.2 µM, and the PCR program was started. The reaction was firstly heated to 94° C. for 5 minutes and then incubated for 25 cycles of 94° C. for 30 seconds, 56° C. for 30 seconds and 68° C. for 30 seconds, and finally, at 68° C. for 10 minutes. The expected PCR products were separated by preparative agarose gel electrophoresis and purified by Wizard SV Gel and PCR Clean-up kits according to the manufacturer's instructions.

In the library, complete DNA fragments contained sfiI and NotI restriction enzyme recognition sites at each end, and was digested by restriction endonuclease sfiI/NotI for restriction digestion and inserted into phagemid vector pCANTAB 5E digested by the same two enzymes. Ligation products were isolated and desalted using Wizard SV Gel and PCR Clean-up Kit for electrotransformation. For electrotransformation, a home-made competent *E. coli* ER2738 was used with electroporation cuvette and electroporation instrument Gene Pulser II. A library containing $1.1 \times 10^{10}$ mutants was finally confirmed.

In addition, the inventors adopted the method of error prone PCR to randomly mutate the whole P7D4 fragment to construct a library T2 with a capacity of $7.9 \times 10^9$, in which the amplification primer pair is S1 and S6, and the manner for cloning and construction is the same as that for the above described H12 and L12.

The screening of the above three affinity mature libraries is consistent with the screening procedure in Example 1. The inventors identified six high-affinity P7D4 series of mutant clones, am4, am14, am20, am35, am42 and T2-23 by screening, sequence information of which is shown as follows:

am4 nucleotide sequence (SEQ ID NO: 24, wherein positions 76-105 is the heavy chain CDR1, positions 148-198 is the heavy chain CDR2, positions 295-330 is the heavy chain CDR3, and positions 475-516 is light chain CDR1; positions 562-582 is light chain CDR2 and positions 679-708 is light chain CDR3; wherein positions 1-363 is heavy chain nucleotide sequence and positions 409-741 is light chain nucleotide sequence, and positions 364-408 is (Gly$_4$Ser)$_3$ linker):

CAGGTGCAGCTGCAGGAGTCCGGGGGAGGCTTAGTTCAGCCTGGGAGGTC

CCTGAGACTCTCCTGTGCAGCCTCTGGATTCACCTTCAGTACGTATGCTA

TGACGTGGGTCCGCCAGGCTCCAGGCAAGGGGCTGGAGTGGGTCTCATCT

ATTAGTAGTAGTGGTGGAAGTACATACTACGCAGACTCCGTGAAGGGCCG

GTTCACCATCTCCAGAGACAATTCCAAGAACACGCTGTATCTGCAAATGA

ACAGCCTGAGAGCCGAGGACACGGCCGTATATTACTGTGCGAAAGATCGA

CGAGGGAGCCACGCTGATGCTTTTGATGTCTGGGGCCAAGGAACCCTGGT

CACCGTCTCGAGT*GGTGGAGGCGGTTCAGGCGGAGGTGGTTCTGG*

*CGGTGGCGGATCG*CAGTCTGCCCTGACTCAGCCTCCCTCCGCGTCCGGG

TCTCCTGGACAGTCAGTCACCATCTCCTGCACTGGAACCAGCAGTGACGT

TGGTGGTTATAACTATGTCTCCTGGTACCAACAGTACCCAGGCAAAGCCC

CCAAACTCCTCATCTATGGTAACAGCAATCGGCCCTCAGGGGTCCCTGAC

CGATTCTCTGGCTCCAAGTCTGGCACCTCAGCCTCCCTGGCCATCACTGG

GCTCCAGGCTGAGGATGGGGCTGATTATTACTGCCAGTCCTATGACAGCA

GCCTGCGTGTGGTATTCGGCGGAGGGACCAAGGTCACCGTCCTAGGT am4 amino acid sequence (SEQ ID NO: 25):
QVQLQESGGGLVQPGRSLRLSCAASGFTFSTYAMTWVRQAPGKGLEWVSS

ISSSGESTYYADSVKGRFTISRDNSKNTLYLQMNSLRAEDTAVYYCAKDR

RGSHADAFDVWGQGTLVTVSS*GGGGSGGGGSGGGGS*QSALTQPPSASGS

PGQSVTISCTGTSSDVGGYNYVSWYQQYPGKAPKLLIYGNSNRPSGVPDR

FSGSKSGTSASLAITGLQAEDGADYYCQSYDSSLRVVFGGGTKVTVLG

Heavy chain CDR1:
(SEQ ID NO: 60)
GFTFSTYAMT

Heavy chain CDR2:
(SEQ ID NO: 61)
SISSSGESTYYADSVKG

Heavy chain CDR3:
(SEQ ID NO: 14)
DRRGSHADAFDV

Light chain CDR1:
(SEQ ID NO: 16)
TGTSSDVGGYNYVS

Light chain CDR2:
(SEQ ID NO: 18)
GNSNRPS

Light chain CDR3:
(SEQ ID NO: 20)
QSYDSSLRVV

Wherein positions 1-121 is heavy chain amino acid sequence, positions 137-247 is light chain amino acid sequence, and positions 122-136 is (Gly$_4$Ser)$_3$ linker sequence.

am14 nucleotide sequence (SEQ ID NO: 26, wherein, positions 76-105 is heavy chain CDR1, positions 148-198th is heavy chain CDR2, positions 295-330 is heavy chain CDR3, positions 475-516 is light chain CDR1, positions 562-582 is light chain CDR2 and positions 679-708 is light chain CDR3; wherein positions 1-363 is heavy chain nucleotide sequence and positions 409-741 is light chain nucleotide sequence, positions 364-408 is (Gly₄Ser)₃ linker):

```
CAGGTGCAGCTGCAGGAGTCCGGGGGAGGCTTAGTTCAGCCTGGGAGGTC

CCTGAGACTCTCCTGTGCAGCCTCTGGATTCACCTTCAGTACTTATGCTA

TGGCTTGGGTCCGCCAGGCTCCAGGCAAGGGGCTGGAGTGGGTCTCAGAA

ATTAGTAGTTCTGGTAGTAGGACATACTACGCAGACTCCGTGAAGGGCCG

GTTCACCATCTCCAGAGACAATTCCAAGAACACGCTGTATCTGCAAATGA

ACAGCCTGAGAGCCGAGGACACGGCCGTATATTACTGTGCGAAAGATCGA

CGAGGGAGCCACGCTGATGCTTTTGATGTCTGGGGCCAAGGAACCCTGGT

CACCGTCTCGAGTGGTGGAGGCGGTTCAGGCGGAGGTGGTTCTGG

CGGTGGCGGATCGCAGTCTGCCCTGACTCAGCCTCCCTCCGCGTCCGGG

TCTCCTGGACAGTCAGTCACCATCTCCTGCACTGGAACCAGCAGTGACGT

TGGTGGTTATAACTATGTCTCCTGGTACCAACAGTACCCAGGCAAAGCCC

CCAAACTCCTCATCTATGGTAACAGCAATCGGCCCTCAGGGGTCCCTGAC

CGATTCTCTGGCTCCAAGTCTGGCACCTCAGCCTCCCTGGCCATCACTGG

GCTCCAGGCTGAGGATGGGGCTGATTATTACTGCCAGTCCTATGACAGCA

GCCTGCGTGTGGTATTCGGCGGAGGGACCAAGGTCACCGTCCTAGGT
``` am14 amino acid sequence (SEQ ID NO: 27):
QVQLQESGGGLVQPGRSLRLSCAASGFTFSTYAMAWVRQAPGKGLEWVSE
ISSSGSRTYYADSVKGRFTISRDNSKNTLYLQMNSLRAEDTAVYYCAKDR
RGSHADAFDVWGQGTLVTVSSGGGGSGGGGSGGGGSQSALTQPPSASGSP
GQSVTISCTGTSSDVGGYNYVSWYQQYPGKAPKLLIYGNSNRPSGVPDRF
SGSKSGTSASLAITGLQAEDGADYYCQSYDSSLRVVFGGGTKVTVLG Heavy chain CDR1:
                                        (SEQ ID NO: 62)
GFTFSTYAMA Heavy chain CDR2:
                                        (SEQ ID NO: 63)
EISSSGSRTYYADSVKG Heavy chain CDR3:
                                        (SEQ ID NO: 14)
DRRGSHADAFDV Light chain CDR1:
                                        (SEQ ID NO: 16)
TGTSSDVGGYNYVS Light chain CDR2:
                                        (SEQ ID NO: 18)
GNSNRPS Light chain CDR3:
                                        (SEQ ID NO: 20)
QSYDSSLRVV Wherein positions 1-121 is heavy chain amino acid sequence and positions 137-247 is light chain amino acid sequence, and positions 122-136 is (Gly₄Ser)₃ linking sequence.

am20 nucleotide sequence (SEQ ID NO: 28, positions 76-105 is heavy chain CDR1, positions 148-198 is heavy chain CDR2, positions 295-330 is heavy chain CDR3, positions 475-516 is light chain CDR1, positions 562-582 is light chain CDR2, positions 679-708 is light chain CDR3; wherein positions 1-363 is heavy chain nucleotide sequence, and positions 409-741 is light chain nucleotide sequence, positions 364-408 is (Gly₄Ser)₃ linking sequence):

```
CAGGTGCAGCTGCAGGAGTCCGGGGGAGGCTTAGTTCAGCCTGGGAGGTC

CCTGAGACTCTCCTGTGCAGCCTCTGGATTCACCTTCAGTACGTATGCTA

TGAATTGGGTCCGCCAGGCTCCAGGCAAGGGGCTGGAGTGGGTCTCAGCG

ATTAGTATGTCTGGTGAATCTACATACTACGCAGACTCCGTGAAGGGCCG

GTTCACCATCTCCAGAGACAATTCCAAGAACACGCTGTATCTGCAAATGA

ACAGCCTGAGAGCCGAGGACACGGCCGTATATTACTGTGCGAAAGATCGA

CGAGGGAGCCACGCTGATGCTTTTGATGTCTGGGGCCAAGGAACCCTGGT

CACCGTCTCGAGTGGTGGAGGCGGTTCAGGCGGAGGTGGTTCTGG

CGGTGGCGGATCGCAGTCTGCCCTGACTCAGCCTCCCTCCGCGTCCGGG

TCTCCTGGACAGTCAGTCACCATCTCCTGCACTGGAACCAGCAGTGACGT

TGGTGGTTATAACTATGTCTCCTGGTACCAACAGTACCCAGGCAAAGCCC

CCAAACTCCTCATCTATGGTAACAGCAATCGGCCCTCAGGGGTCCCTGAC

CGATTCTCTGGCTCCAAGTCTGGCACCTCAGCCTCCCTGGCCATCACTGG

GCTCCAGGCTGAGGATGGGGCTGATTATTACTGCCAGTCCTATGACAGCA

GCCTGCGTGTGGTATTCGGCGGAGGGACCAAGGTCACCGTCCTAGGT
``` am20 amino sequence (SEQ ID NO: 29):
QVQLQESGGGLVQPGRSLRLSCAASGFTFSTYAMNWVRQAPGKGLEWVSA
ISMSGESTYYADSVKGRFTISRDNSKNTLYLQMNSLRAEDTAVYYCAKDR
RGSHADAFDVWGQGTLVTVSSGGGGSGGGGSGGGGSQSALTQPPSASGSP
GQSVTISCTGTSSDVGGYNYVSWYQQYPGKAPKLLIYGNSNRPSGVPDRF
SGSKSGTSASLAITGLQAEDGADYYCQSYDSSLRVVFGGGTKVTVLG Heavy chain CDR1:
                                        (SEQ ID NO: 64)
GFTFSTYAMA Heavy chain CDR2:
                                        (SEQ ID NO: 65)
AISMSGESTYYADSVKG Heavy chain CDR3:
                                        (SEQ ID NO: 14)
DRRGSHADAFDV Light chain CDR1:
                                        (SEQ ID NO: 16)
TGTSSDVGGYNYVS Light chain CDR2:
                                        (SEQ ID NO: 18)
GNSNRPS Light chain CDR3:
                                        (SEQ ID NO: 20)
QSYDSSLRVV Wherein positions 1-121 is heavy chain amino acid sequence and positions 137-247 is light chain amino acid sequence, and positions 122-136 is (Gly₄Ser)₃ linking sequence.

am35 nucleotide sequence (SEQ ID NO: 30, positions 76-105 is heavy chain CDR1, positions 148-198 is heavy chain CDR2, positions 295-330 is heavy chain CDR3, positions 475-516 is light chain CDR1, positions 562-582 is light chain CDR2, positions 679-708 is light chain CDR3; wherein positions 1-363 is heavy chain nucleotide sequence, and positions 409-741 is light chain nucleotide sequence, positions 364-408 is (Gly$_4$Ser)$_3$ linking sequence):

```
CAGGTGCAGCTGCAGGAGTCCGGGGGAGGCTTAGTTCAGCCTGGGAGGTC

CCTGAGACTCTCCTGTGCAGCCTCTGGATTCACCTTCAGTAGCTATGCTA

TGCACTGGGTCCGCCAGGCTCCAGGCAAGGGGCTGGAGTGGGTCTCAGCT

ATTAGTAGTAGTGGTGGTAGCACATACTACGCAGACTCCGTGAAGGGCCG

GTTCACCATCTCCAGAGACAATTCCAAGAACACGCTGTATCTGCAAATGA

ACAGCCTGAGAGCCGAGGACACGGCCGTATATTACTGTGCGAAAGATCGA

CGAGGGAGCCACGCTGATGCTTTTGATGTCTGGGGCCAAGGAACCCTGGT

CACCGTCTCGAGTGGTGGAGGCGGTTCAGGCGGAGGTGGTTCTGG

CGGTGGCGGATCGCAGTCTGCCCTGACTCAGCCTCCCTCCGCGTCCGGG

TCTCCTGGACAGTCAGTCACCATCTCCTGCACTGGAACCAGCAGTGACGT

TGGTCATAAGTTTCCTGTCTCCTGGTACCAACAGTACCCAGGCAAAGCCC

CCAAACTCCTCATCTATAAGAATCTTTTGCGGCCCTCAGGGGTCCCTGAC

CGATTCTCTGGCTCCAAGTCTGGCACCTCAGCCTCCCTGGCCATCACTGG

GCTCCAGGCTGAGGATGGGGCTGATTATTACTGCCAGTCCTATGACAGCA

GCCTGCGTGTGGTATTCGGCGGAGGGACCAAGGTCACCGTCCTAGGT
``` am35 amino acid sequence (SEQ ID NO: 31):
QVQLQESGGGLVQPGRSLRLSCAASGFTFSSYAMHWVRQAPGKGLEWVSA

ISSSGGSTYYADSVKGRFTISRDNSKNTLYLQMNSLRAEDTAVYYCAKDR

RGSHADAFDVWGQGTLVTVSSGGGGSGGGGSGGGGSQSALTQPPSASGSP

GQSVTISCTGTSSDVGHKFPVSWYQQYPGKAPKLLIYKNLLRPSGVPDRF

SGSKSGTSASLAITGLQAEDGADYYCQSYDSSLRVVFGGGTKVTVLG

Heavy chain CDR1:
(SEQ ID NO: 10)
GFTFSSYAMH

Heavy chain CDR2:
(SEQ ID NO: 66)
AISSSGGSTYYADSVKG

Heavy chain CDR3:
(SEQ ID NO: 14)
DRRGSHADAFDV

Light chain CDR1:
(SEQ ID NO: 67)
TGTSSDVGHKFPVS

Light chain CDR2:
(SEQ ID NO: 68)
KNLLRPS

Light chain CDR3:
(SEQ ID NO: 20)
QSYDSSLRVV

Wherein positions 1-121 is the heavy chain amino acid sequence, positions 137-247 is the light chain amino acid sequence, and positions 122-136 is the (GlyGlyGlyGlySer (SEQ ID NO: 99))$_3$ linking sequence.

am42 nucleotide sequence (SEQ ID NO: 32, positions 76-105 is heavy chain CDR1, positions 148-198 is heavy chain CDR2, positions 295-330 is heavy chain CDR3, positions 475-516 is light chain CDR1, positions 562-582 is light chain CDR2, positions 679-708 is light chain CDR3; wherein positions 1-363 is heavy chain nucleotide sequence, and positions 409-741 is light chain nucleotide sequence, positions 364-408 is (Gly$_4$Ser)$_3$ linking sequence):

```
CAGGTGCAGCTGCAGGAGTCCGGGGGAGGCTTAGTTCAGCCTGGGAGGTC

CCTGAGACTCTCCTGTGCAGCCTCTGGATTCACCTTCAGTAGCTATGCTA

TGCACTGGGTCCGCCAGGCTCCAGGCAAGGGGCTGGAGTGGGTCTCAGCT

ATTAGTAGTAGTGGTGGTAGCACATACTACGCAGACTCCGTGAAGGGCCG

GTTCACCATCTCCAGAGACAATTCCAAGAACACGCTGTATCTGCAAATGA

ACAGCCTGAGAGCCGAGGACACGGCCGTATATTACTGTGCGAAAGATCGA

CGAGGGAGCCACGCTGATGCTTTTGATGTCTGGGGCCAAGGAACCCTGGT

CACCGTCTCGAGTGGTGGAGGCGGTTCAGGCGGAGGTGGTTCTGG

CGGTGGCGGATCGCAGTCTGCCCTGACTCAGCCTCCCTCCGCGTCCGGG

TCTCCTGGACAGTCAGTCACCATCTCCTGCACTGGAACCAGCAGTGACGT

TGGTCTTATGCATAATGTCTCCTGGTACCAACAGTACCCAGGCAAAGCCC

CCAAACTCCTCATCTATAAGTCTTCGTCTCGGCCCTCAGGGGTCCCTGAC

CGATTCTCTGGCTCCAAGTCTGGCACCTCAGCCTCCCTGGCCATCACTGG

GCTCCAGGCTGAGGATGGGGCTGATTATTACTGCCAGTCCTATGACAGCA

GCCTGCGTGTGGTATTCGGCGGAGGGACCAAGGTCACCGTCCTAGGT
``` am42 amino acid sequence (SEQ ID NO: 33):
QVQLQESGGGLVQPGRSLRLSCAASGFTFSSYAMHWVRQAPGKGLEWVSA

ISSSGGSTYYADSVKGRFTISRDNSKNTLYLQMNSLRAEDTAVYYCAKDR

RGSHADAFDVWGQGTLVTVSSGGGGSGGGGSGGGGSQSALTQPPSASGSP

GQSVTISCTGTSSDVGLMHNVSWYQQYPGKAPKLLIYKSSSRPSGVPDRF

SGSKSGTSASLAITGLQAEDGADYYCQSYDSSLRVVFGGGTKVTVLG

Heavy chain CDR1:
(SEQ ID NO: 10)
GFTFSSYAMH

Heavy chain CDR2:
(SEQ ID NO: 66)
AISSSGGSTYYADSVKG

Heavy chain CDR3:
(SEQ ID NO: 14)
DRRGSHADAFDV

Light chain CDR1:
(SEQ ID NO: 69)
TGTSSDVGLMHNVS

Light chain CDR2:
(SEQ ID NO: 70)
KSSSRPS

Light chain CDR3:
(SEQ ID NO: 20)
QSYDSSLRVV

Wherein positions 1-121 is heavy chain amino acid sequence and positions 137-247 is light chain amino acid sequence, and positions 122-136 is (Gly₄Ser)₃ linking sequence.

T2-23 nucleotide sequence (SEQ ID NO: 34, positions 76-105 is heavy chain CDR1, positions 148-198 is heavy chain CDR2, positions 295-330 is heavy chain CDR3, positions 475-516 is light chain CDR1, positions 562-582 is light chain CDR2, positions 679-708 is light chain CDR3; wherein positions 1-363 is heavy chain nucleotide sequence, and positions 409-741 is light chain nucleotide sequence, positions 364-408 is (Gly₄Ser)₃ linking sequence):

CAGGTGCAGCTGCAGGAGTCCGGGGGAGGCTTAGTTCAGCCTGGGAGGTC

CCTGAGACTCTCCTGTGCAGCCTCTGGATTCACCTTCAGTAGCTATGCTA

TGCAGTGGGTCCGCCAGGCTCCAGGCAAGGGGCTGGAGTGGGTCTCAGCT

ATTAGTAGTAGTGGTCGTAGCACATACTACGCAGACTCCGTGGAGGGCCG

GTTCACCATCTCCAGAGACAATTCCAAGAACACGCTGTATCTGCAAATGA

ACAGCCTGAGAGCCGAGGACACGGCCGTATATTACTGTGCGAAAGATCGA

CGAGGGAGCCACGCTGATGCTTTAAATGTCTGGGGCCAAGGAACCCTGGT

CACCGTCTCGAGTGGTGGAGGCGGTTCAGGCGGAGGTGGTTCTGG

CGGTGGCGGATCGCAGTCTGCCCTGACTCAGCCTCCCTCCGCGTCCGGG

TCTCCTGGACAGTCAGTCACCATCTCCTGCACTGGAACCAGCAGTGACGT

TGGTGGTTATAACTATGTCTCCTGGTACCAACAGTACCCAGGCAAGCCC

CCAAACTCCTCATCTATGGTAACAGCAATCGGCCCTCAGGGGTCCCTGAC

CGATTCTCTGGCTCCAAGTCTGGCACCTCAGCCTCCCTGGCCATCACTGG

GCTCCAGGCTGAGGATGGGGCTGATTATTACTGCCAGTCCTATGACAGCA

GCCTGCGTGTGGTATTCGGCGGAGGGACCAAGGTCACCGTCCTAGGT

T2-23 amino acid sequence (SEQ ID NO: 35):
QVQLQESGGGLVQPGRSLRLSCAASGFTFSSYAMHWVRQAPGKGLEWVSA

ISSSGRSTYYADSVEGRFTISRDNSKNTLYLQMNSLRAEDTAVYYCAKDR

RGSHADALNVWGQGTLVTVSSGGGGSGGGGSGGGGSQSALTQPPSASGSP

GQSVTISCTGTSSDVGGYNYVSWYQQYPGKAPKLLIYGNSNRPSGVPDRF

SGSKSGTSASLAITGLQAEDGADYYCQSYDSSLRVVFGGGTKVTVLG

Heavy chain CDR1:
(SEQ ID NO: 10)
GFTFSSYAMH

Heavy chain CDR2:
(SEQ ID NO: 71)
AISSSGRSTYYADSVEG

Heavy chain CDR3:
(SEQ ID NO: 72)
DRRGSHADALNV

Light chain CDR1:
(SEQ ID NO: 16)
TGTSSDVGGYNYVS

Light chain CDR2:
(SEQ ID NO: 70)
KSSSRPS

Light chain CDR3:
(SEQ ID NO: 20)
QSYDSSLRVV

Wherein positions 1-121 is heavy chain amino acid sequence and positions 137-247 is light chain amino acid sequence, and positions 122-136 is (Gly₄Ser)₃ linking sequence.

4.4 SPR Analysis of the Binding Ability of P7D4 Series Antibodies to GPC3

Figure 4:
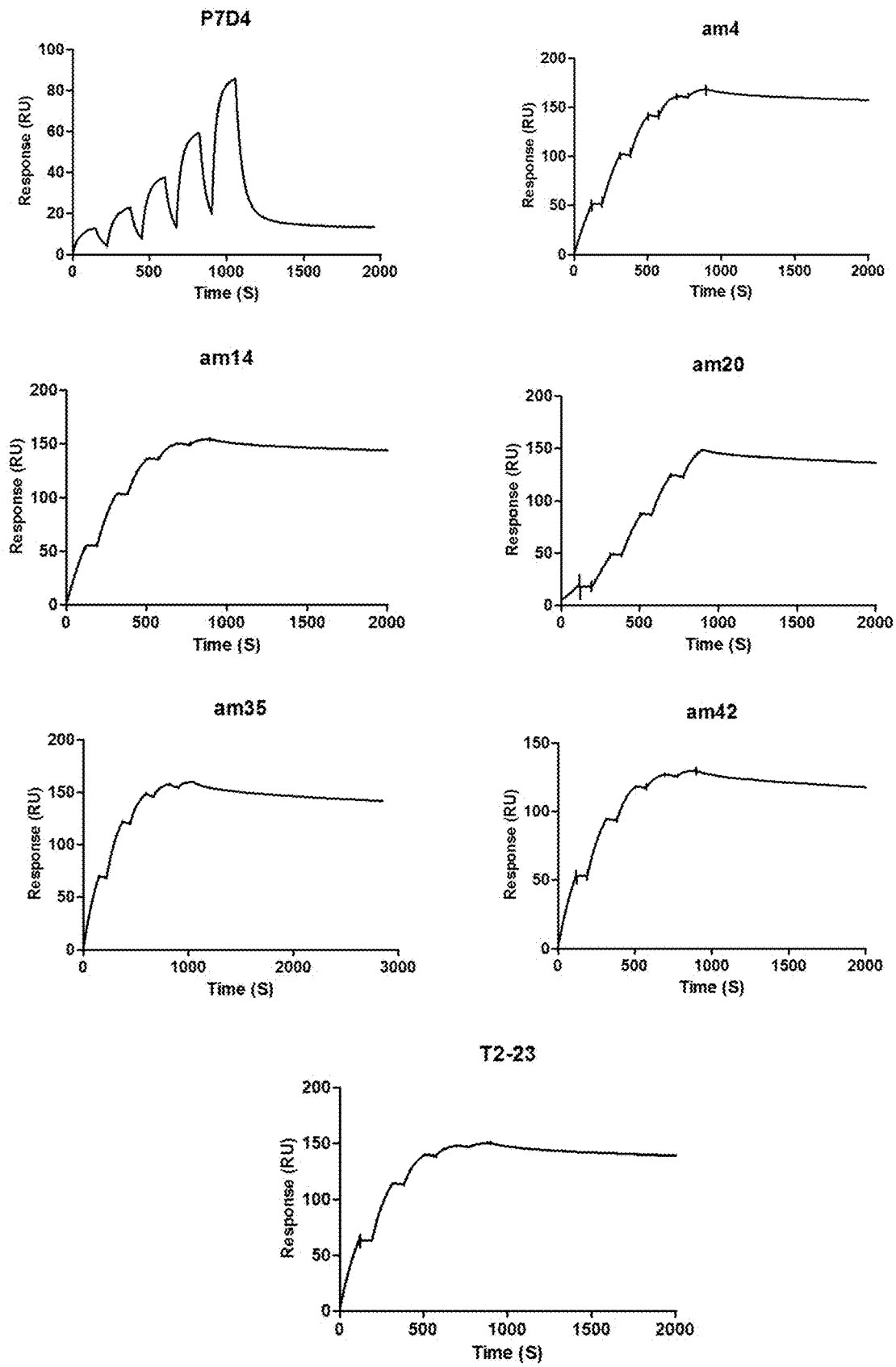
FIG. 4 shows SPR analysis of binding ability for P7D4 series antibodies to GPC3.

To quantitatively analyze the binding of P7D4 series antibodies to GPC3, the affinity and kinetic parameters of P7D4 series single-chain antibodies were measured by capture method using Biacore T200 system (from GE). An anti-human IgG (Fc) antibody (purchased from GE) was coupled to carboxymethyl dextran surface of sensor chip CM5 through primary amino with NHS/EDC coupling according to the manufacturer's instructions. Measurements were performed in 1×HBS-EP+working buffer at 25° C., 30 μl/min, and regeneration condition was 3 M MgCl₂, 10 μl/min for 30 seconds. In each round of the testing cycle, the antibody to be tested is firstly captured onto the chip. GPC3 of a certain concentration flowed over the chip surface. The interaction between human GPC3 and the captured antibody caused the change of the molecular concentration on the surface of the sensor chip which was measured according to changes in SPR Signal and expressed in resonance units (RU). Time vs resonance unit (RU) was plotted. The resulting sensorgram documents the entire reaction including the binding and dissociation processes (FIG. 4). In all single-cycle kinetics, GPC3 concentrations were 5 nM, 10 nM, 20 nM, 40 nM and 80 nM, respectively. The resulting curves were evaluated using Biacore T200 evaluation software and the affinity KD values were calculated. The binding data for all P7D4 single chain antibodies to GPC3 are summarized in Table 1 below.

TABLE 1

Binding data for P7D4 series single chain antibodies to GPC3

| Antibody sample | ka (1/Ms) | kd (1/s) | KD (M) |
| --- | --- | --- | --- |
| P7D4 | 9.31E+04 | 6.17E-03 | 6.64E-08 |
| am4 | 5.39E+05 | 4.08E-05 | 7.56E-11 |
| am14 | 6.73E+05 | 4.43E-05 | 6.46E-11 |
| am20 | 2.12E+05 | 6.47E-05 | 3.06E-10 |
| am35 | 7.38E+05 | 5.2E-05 | 7.14E-11 |
| am42 | 8.16E+05 | 6.70E-05 | 8.21E-11 |
| T2-23 | 8.86E+05 | 5.19E-05 | 5.85E-11 |

It can be seen from Table 1 that P7D4 series mutant single chain antibodies obtained by modification exhibited good and significant increased affinity relative to P7D4 single-chain antibody.

4.5 Analysis of Identification Specificity of P7D4 Series Antibodies

In order to analyze the binding specificity of P7D4 series antibody to GPC3 protein, binding activity of P7D4 series single chain antibody to human GPC family members, including recombinant human GPC1 (rhGPC1), GPC2 (rhGPC2), GPC3 (rhGPC3), GPC5 (rhGPC5) and GPC6 (rhGPC6) (purchased from Andy Biosciences (Shanghai) Co., Ltd.) was detected by ELISA, respectively.

For this purpose, the above 5 antigens were diluted with 0.1 M NaHCO₃ (pH 9.6) coating solution and each well was coated with 100 ng at 50 μl/well overnight at 4° C. and blocked with 2% (w/v) BSA in PBST for 2 hours at room temperature. The plate was then rinsed for three times with PBST and PBST was removed. Subsequently, 100 ng of each antibody protein in PBST was added to each well plate, and the assay for each sample was performed in duplicate wells. After incubated for 2 hours at 37° C., the plates were rinsed for three times with PBST followed by addition of 100 µl/well HRP-labeled rabbit anti-human Fc antibody (purchased from Shanghai Rui Jin Biotechnology Co., Ltd.) diluted at 1:20000 and incubated at 37° C. for 1 hour. For detection, wells were rinsed for three times with PBST followed by three times with PBS and finally with TMB for development for 10 min. The chromogenic reaction was stopped with 50 µl of 2 M $H_2SO_4$ per well, and extinction value was measured at 450 nm with enzyme-linked immunodetector (Bio-Rad).

Figures 5, 6:
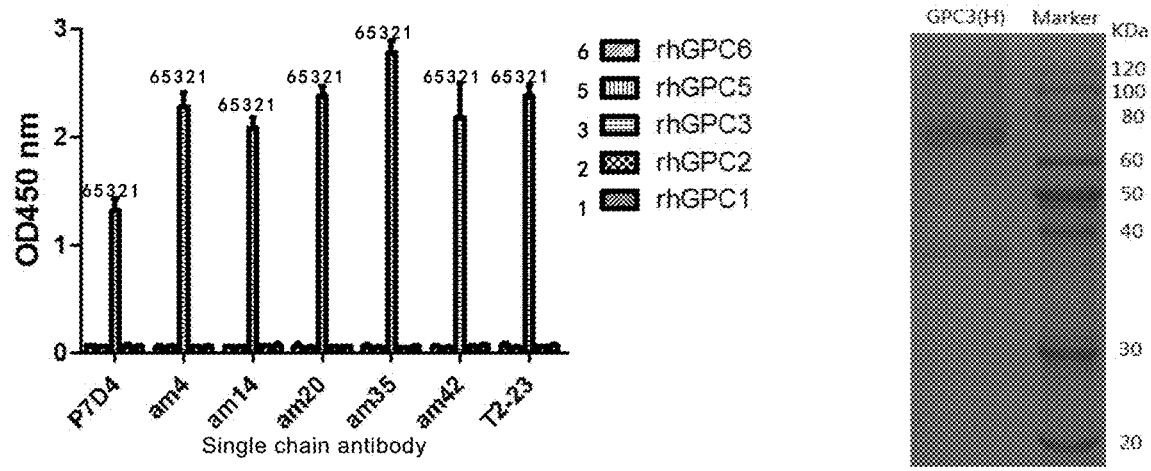
FIG. 5 shows P7D4 series antibodies specifically binding to recombinant human GPC3.
FIG. 6 shows SDS PAGE electrophoresis of expressed and purified GPC3 protein.

Results are shown in FIG. 5, and all P7D4 series single chain antibodies only specifically bind to human GPC3 and do not bind to human GPC1, GPC2, GPC5 and GPC6.

Example 5. Preparation of Human GPC3 Antigen and Humanized Monoclonal Antibodies Against the Antigen 5.1 Expression and Purification of Human GPC3 in Eukaryotic Expression System
5.1.1 Construction and Identification of GPC3 Vector PCR amplification was performed using human hepatoma cell line Huh-7 cDNA as a template with following primers GPC3-F: GATCGCTAGCACAGCCCCCGCCGCCGC (SEQ ID NO: 54), GPC3-R: GTACGGATCCTTCAGCGGGGAATGAACGTTC (SEQ ID NO: 55) to obtain GPC3 fragment (1.6 kb) with NheI/BamHI site at both ends. The obtained PCR fragment was double digested with endonuclease NheI/BamHI (purchased from Fermentas), and the plasmid vector V5H (purchased from Raygene) was double digested with endonuclease NheI/BamHI. The vector and inserted fragment were recovered by agarose gel electrophoresis and ligated by T4 DNA ligase (purchased from NEB) and transformed into host strain TOP10 (purchased from LIFE Co.). The host strains were screened by Ampicillin-resistance, clones were pick out, plasmids were extracted and double digested by NheI/BamHI (purchased from Fermentas), and positive clones containing the inserted fragment were identified and verified by sequencing to obtain eukaryotic expression plasmid V5H-GPC3 containing the correct human GPC3 gene sequence.

5.1.2 Expression and Purification of Human GPC3 Protein
5.1.2.1. Liposome Transfection and Culture of V5H-GPC3 Plasmid Well-grown HEK293F cells (HEK293F, purchased from LIFE Co., Ltd.) were seeded in a cell culture flask at a density of $1 \times 10^6$ cells/ml and incubated overnight at 37° C. and 120 rpm for future use. The plasmid V5H-GPC3 obtained in the above step and lipofectamine 293Fectin (purchased from LIFE) was diluted with DMEM and mixed gently, incubated at room temperature for 20 min. The incubated DNA-liposome complex was added to 293F cells and cultured at 37° C. and 120 rpm for 120 h. The cell culture was collected and centrifuged at 4500 g for 15 min. Cells were removed and the supernatant was kept.
5.1.2.2. Purification of GPC3 Protein 1 ml of Ni-NTA Agarose affinity filler was loaded and the Ni-NTA affinity column was equilibrated with 10 column volumes of equilibration buffer (50 mM PB, 0.3 M NaCl, 10 mM imidazole, pH 8.0). After centrifugation, the supernatant of cell culture was passed through a Ni-NTA affinity column at 1 ml/min and the flow-through was collected and stored at 4° C. 10 column volumes of wash buffer 1 (50 mM PB, 0.3 M NaCl, 20 mM imidazole, pH 8.0) was used for washing and the flow-through was collected at 4° C. 4-5 column volumes of elution buffer (50 mM PB, 0.3 M NaCl, 250 mM imidazole, pH 8.0) were used for elution and the eluate was collected and dialysed in dialysis fluid (50 mM PB, pH 7.8, 0.3 M NaCl, Glycerol) overnight at 4° C. to obtain GPC3(H) protein, and a small amount was used in SDS PAGE electrophoresis (FIG. 6).
5.2 Human GPC3 Antigen Immunization Recombinant protein immunization: 1 ml of the purified human GPC3 protein GPC3(H) (1.0 mg/mL) obtained in the above Example 5.1 as an antigen was sufficiently emulsified and mixed with 1 mL of complete Freund's adjuvant (Sigma-Aldrich Co., Ltd.) for subcutaneously immunizing BALB/c mice (6-8 weeks old, 100 µg of human GPC3(H) protein antigen per mouse). Four weeks later, the human GPC3 antigen was emulsified and mixed with incomplete Freund's adjuvant. The mice were immunized through intraperitoneal injection (50 µg for each mouse), followed by an interval of 2 weeks and then 50 µg of antigen was intraperitoneally administered for booster immunization. One week after the fourth booster immunization, GPC3(H) protein was used for coating. The mouse antiserum titer was detected by ELISA, and the booster immunization was continued until the antiserum titer reached $>10^5$ in mice.

Three weeks after the last booster immunization, 20 µg of human GPC3(H) protein was immunized in spleen for furture use.
5.3 Establishment of Anti-Human GPC3 Hybridoma Cell Lines Four days after boosting in the spleen of mouse, the spleens were taken aseptically and the lymphocytes were isolated by filtration through a 100-mesh filter, fused with myeloma cell line SP2/0, selectively cultured with hypoxathine, aminopterin and thymidine (HAT) for three days, and then HT medium was added and the culture was continued for one week.

GPC3(H) antigen was used for coating, and the positive clones were screened by ELISA and subcloned for three times by limiting dilution. The cells were cultured for another 2 months. Finally, stable hybridoma cell lines (clone numbers 5A5, 7C9 and 11D3) were obtained.
5.4 Production of Ascites and Purification of Antibody F1 mice of 8-10 weeks old were injected intraperitoneally with 100 µL of pristane (purchased from Sigma-Aldrich), and 1 week later, hybridoma cell clones of the above Example 5.4 were taken and intraperitoneally injected into the mice at $5 \times 10^5$ cells/mouse to prepare ascites. After 7 to 10 days, ascites was collected and centrifuged at 10000 g for 10 mins, and the supernatant was taken for future use. Protein G affinity column (purchased from GE) was returned to room temperature and 5 column volumes of PBS (0.01 M PB, 0.15 M NaCl, pH 7.4) was used for equilibration. The supernatant of ascites was mixed with an equal volume of PBS (0.01 M PB, 0.15 M NaCl, pH 7.4), filtered through a 0.22 µM filter and the filtered ascites supernatant was loaded on a Protein G affinity column and washed with 5 volumes of PBS. The column was eluted with elution buffer (0.1M Glycine HCl, pH 2.7) and the elution was neutralized with $\frac{1}{10}$ volume of neutralization buffer (1M $NaH_2PO_4$, pH 9.0). The solution was dialyzed against PBS (0.01 M PB, 0.15 M NaCl, pH 7.4), during which PBS was changed for two times and the interval between two changes was longer than 5 hours. The dialyzed solution was centrifuged at 10000 g for 10 min and the supernatant was filtered through a 0.22 um filter to obtain a solution of the purified anti-human GPC3 monoclonal antibody produced by each clone. According to analysis, 5A5 exhibited good antigen binding ability.

5.5 Humanization of GPC3 Clone 5A5

5.5.1 Sequence Analysis of 5A5 Antibody

5A5 exhibited good antigen binding ability. The variable region sequences of VL and VH of 5A5 antibody were determined. According to the naming scheme of CDRs of Kabat, Chothia and IMGT, the sequence of six CDRs of the light and heavy chain of the antibody were determined.

The nucleotide sequence of 5A5 heavy chain is shown as follows (SEQ ID NO: 56, where the three underlined segments are successively CDR1, CDR2, CDR3):

CAGGTTCAACTGCAGCAGTCTGGGACTGAGCTGGTGAGGCCTGGGGCTTC

AGTGAAGCTGTCCTGCAAGGCTTTGGGCTACACATTTACT<u>GACTATGAAA</u>

<u>TGCACTGGGT</u>GAAGCAGACACCTGTGCATGGCCTGGAGTGGATTGGA<u>GCT</u>

<u>ATTCATCCAGGAAGTGGTGATACTGCCTACAATCAGAGGTTCAAGGGCAA</u>

GGCCACACTGACTGCAGACAAATCTTCCAGCACAGCCTACATGGAGTACA

GCAGCCTGACATCTGAGGACTCTGCTGTCTATTACTGTACAAGA<u>TTTTAT</u>

<u>TCCTATGCTTAC</u>TGGGGCCAAGGGACTCTGGTCACTGTCTCTGCA

The nucleotide sequence of 5A5 light chain is shown as follows (SEQ ID NO: 57, where the three underlined segments are successively CDR1, CDR2, CDR3):

GATGTTGTGATGACCCAAACTCCACTCTCCCTGCCTGTCAGTCTTGGAG

ATCAAGCCTCCATCTCTTGC<u>AGATCTAGTCAGAGCCTTGTACACAGTAA</u>

<u>TGGAAACACCTATTTACAGTGGTACCTGCAGAAGCCAGGCCAGTCTCCA</u>

AAGCTCCTGATCTAC<u>AAAGTTTCCAATCGATTTTCTGGGGTCCCAGACA</u>

GGTTCAGTGGCAGAGGATCAGGGACAGATTTCACACTCAAGATCAGCAG

AGTGGAGGCTGAGGATCTGGGAGTTTATTTCTGC<u>TCTCAAAGTATATAT</u>

<u>GTTCCGTACACGTT</u>CGGAGGAGGGACCAAGCTGGAAATAAAACGG

Amino acid sequence of 5A5 heavy chain (SEQ ID NO: 81, where the three underlined segments are successively CDR1, CDR2, CDR3):

QVQLQQSGTELVRPGASVKLSCKALGYTFT<u>DYEMH</u>WVKQTPVHGLEWIGA

<u>IHPGSGDTAYNQRFKG</u>KATLTADKSSSTAYMEYSSLTSEDSAVYYCTR<u>FY</u>

<u>SYAY</u>WGQGTLVTVSA

Amino acid sequence of 5A5 light chain (SEQ ID NO: 82, where the three underlined segments are successively CDR1, CDR2, CDR3)

DVVMTQTPLSLPVSLGDQASISC<u>RSSQSLVHSNGNTYLQ</u>WYLQKPGQSPK

LLIY<u>KVSNRFS</u>GVPDRFSGRGSGTDFTLKISRVEAEDLGVYFC<u>SQSIYVP</u>

<u>YT</u>FGGGTKLEIKR 5.5.2 Selection of Antibody Template

There are four major factors in the selection of antibody template framework regions: immunogenicity, antigen binding properties, expression, and antibody stability.

(1) Determination of the amino acid residues supporting loop structure of an antibody in the light and heavy chain variable regions of the antibody and the amino acid residues of the light and heavy chain binding regions according to WO2008021156.

(2) Alignment of the full length of the 5A5 light chain or heavy chain variable region with antibodies from IMGT, V BASE or NCBI.

(3) Removing amino acid residues associated with supporting loop within CDR regions of 5A5 light or heavy chain variable region and then sequence alignment with antibodies from IMGT, V BASE or NCBI.

(4) Removing amino acid residues in CDR regions in the light chain or heavy chain variable region of 5A5 and then sequence alignment with antibodies from IMGT, V BASE or NCBI.

(5) Only keeping amino acid residues associated with supporting loop in the light or heavy chain sequence of 5A5, and then sequence similarity alignment with antibodies from IMGT, V BASE or NCBI.

(6) Only keeping amino acid residues associated with supporting loop in light chains or heavy chain frameworks of 5A5 are retained, and then sequence similarity alignment with antibodies from IMGT, V BASE or NCBI.

(7) Selecting the antibody with the highest similarity as the antibody template according to results from the alignment of sequence similarity.

(8) Results from alignment of sequence similarity of heavy chain: Based on the similarity, VH1_69*06 (IMGT, Accession numbers: L22583) was selected as the antibody template for 5A5 heavy chain.

(9) Results from alignment of sequence similarity of light chain: based on the similarity, VK2D_29*02 (IMGT, Accession numbers: U41644) was selected as the antibody template for 5A5 light chain.

5.5.3 CDR Transplantation

The light chain or heavy chain CDR regions of 5A5 antibody are substituted for the CDR regions of the antibody template. Humanized antibody (Y035) was finally identified. Its amino acid sequence is shown as follows:

Humanized Y035 heavy chain (SEQ ID NO: 58):
EVQLVQSGAEVKKPGASVKVSCKASGYTFS<u>DYEMH</u>WVRQAPGQGLEWMGA <u>IHPGSGDTAYNQRFKG</u>RVTITADKSTSTAYMELSSLRSEDTAVYYCAR<u>FY</u>

<u>SYAY</u>WGQGTLVTVSA

Heavy chain CDR1 amino acid sequence is:
(SEQ ID NO: 73)
Asp Tyr Glu Met His;

Heavy chain CDR2 amino acid sequence is:
(SEQ ID NO: 74)
Ala Ile His Pro Gly Ser Gly Asp Thr Ala Tyr Asn Gln Arg Phe Lys Gly;

Heavy chain CDR3 amino acid sequence is:
(SEQ ID NO: 75)
Phe Tyr Ser Tyr Ala Tyr.

-continued
Humanized Y035 light chain (SEQ ID NO: 59):
DIVMTQTPLSLPVITGEPASISCRSSQSLVHSNGNTYLQWYLQKPGQSPQ

LLIYKVSNRFSGVPDRFSGSGSGTDFTLKISRVEAEDVGVYYCSQSIYVP

YTFGQGTKLEIKR

```
Light chain CDR1 amino acid sequence is:
                                        (SEQ ID NO: 76)
Arg Ser Ser Gln Ser Leu Val His Ser Asn Gly Asn Thr Tyr Leu Gln;

Light chain CDR2 amino acid sequence is:
                                        (SEQ ID NO: 77)
Lys Val Ser Asn Arg Phe Ser;

Light chain CDR3 amino acid sequence is:
                                        (SEQ ID NO: 78)
Ser Gln Ser Ile Tyr Val Pro Tyr Thr.
```

5.5.4 Expression and Purification of Humanized Antibody (1) Based on the amino acid sequence of humanized antibody (Y035), the nucleotide sequence was designed and synthesized.

Synthesized light chain nucleotide sequence (SEQ ID NO: 79, including signal peptide encoding sequence):
GGATCGATATCCACCATGGACATGATGGTGCTGGCCCAGTTCCTGGCCT

TCCTGCTGCTGTGGTTCCCAGGCGCTAGATGCGACATCGTGATGACCCA

GACCCCCCTGAGCCTGCCCGTGACCCCCGGCGAGCCCGCCAGCATCAGC

TGCCGGAGCAGCCAGAGCCTGGTGCACAGCAACGGCAACACCTACCTGC

AGTGGTACCTGCAGAAGCCCGGCCAGAGCCCCCAGCTGCTGATCTACAA

GGTGAGCAACCGGTTCAGCGGCGTGCCCGACCGGTTCAGCGGCAGCGGC

AGCGGCACCGACTTCACCCTGAAGATCAGCCGGGTGGAGGCCGAGGACG

TGGGCGTGTACTACTGCAGCCAGAGCATCTACGTGCCCTACACCTTCGG

CCAGGGCACCAAGCTGGAGATCAAACGTACGGTGGCT

Synthesized heavy chain nucleotide sequence (SEQ ID NO: 80, including signal peptide encoding sequence):
GGATCGATATCTGCGGCCTATCTAGCCACCATGCGGGTGCTGATCCTGC

TGTGGCTGTTTACCGCCTTCCCCGGCTTCCTGAGCGAGGTGCAGCTGGT

GCAGAGCGGCGCCGAGGTGAAGAAGCCCGGCGCCAGCGTGAAGGTGAGC

TGCAAGGCCAGCGGCTACACCTTCAGCGACTACGAGATGCACTGGGTGC

GGCAGGCCCCCGGCCAGGGCCTGGAGTGGATGGGCGCCATCCACCCCGG

CAGCGGCGACACCGCCTACAACCAGCGGTTCAAGGGCCGGGTGACCATC

ACCGCCGACAAGAGCACCAGCACCGCCTACATGGAGCTGAGCAGCCTGC

GGAGCGAGGACACCGCCGTGTACTACTGCGCCCGGTTCTACAGCTACGC

CTACTGGGGCCAGGGCACCCTGGTGACCGTGAGCGCCGCTAGCACCAAA (2) The synthesized antibody nucleotide sequence (signal peptide: positions 16-81 (light chain), positions 31-84 (heavy chain)) was inserted into mammalian cell expression vector, so as to construct antibody expression vector containing heavy chain and light chain, respectively, and the sequence of the antibody was identified by sequencing. In particular:

The synthesized light chain and pIK-hu12L (purchased from Shanghai Rui Jin Biotechnology Co., Ltd.) were double digested with EcoRV and BsiWI, and the light chain was inserted into pIK-hu12L.

The synthesized heavy chain and the modified pIH-hu12H (purchased from Shanghai Rui-Jin Biotechnology Co., Ltd., an NheI restriction site was added by synonymous mutation on CH1) were double digested with EcoRV and NheI, and the heavy chain was inserted into pIH-hu12H.

The digested and linked vector was transformed into TOP10 competent cells, and the positive clones were identified by PCR. The correct clones were confirmed by sequencing. The vector was transiently transfected into 293F cells by 293Fectin and expressed. The 293F culture supernatant was collected by centrifugation, filtered through a 0.45 μm filter and passed through Protein A column for affinity chromatography. A280 was determined by spectrophotometer to determine the concentration of the purified antibody.

5.6 SPR Analysis of the Binding Ability of Humanized Antibody Y035 to Human GPC3

Figures 7, 8:
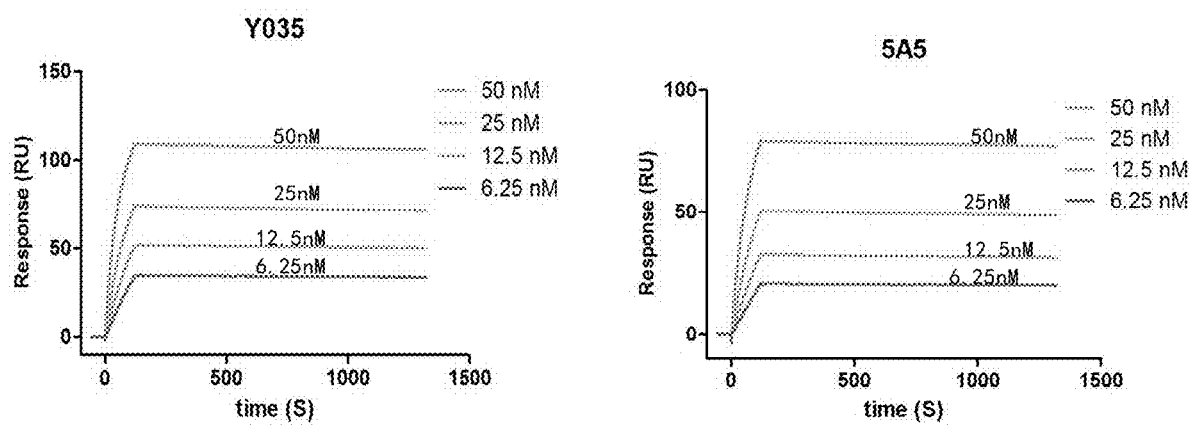
FIG. 7 shows kinetic analysis of binding of antibody Y035 to human GPC3.
FIG. 8 shows kinetic analysis of binding of antibody 5A5 to human GPC3.

To quantitatively analyze the binding of antibody Y035 to antigen human GPC3, the affinity and kinetic parameters of antibody Y035 were measured by multi-cycle kinetic assay using Biacore T200 system (from GE). Antigen human GPC3 (purchased from Shanghai Rui-Jin Biotechnology Co., Ltd.) was coupled to carboxymethyl dextran surface of sensor chip CM5 through primary amino with NHS/EDC coupling according to the manufacturer's instructions, and the final amount of the conjugated ligand was 305RU. Kinetic measurements were performed in 1×HBS-EP+working buffer at 25° C., 30 μl/min, and regeneration condition was 10 mM Glycine-HCl (pH2.5), 10 μl/min for 25 seconds. In each round of the testing cycle, antibody Y035 of a certain concentration flowed over the chip surface. The interaction between the antibody and the antigen protein human GPC3 fixed on the chip caused the change of the molecular concentration on the surface of the sensor chip which was measured according to changes in SPR Signal and expressed in resonance units (RU). Time vs resonance unit (RU) was plotted and after RU value of the reference channel without fixed antigen was subtracted, the resulting sensorgram documents the entire reaction including the binding and dissociation processes. Kinetic analysis of the binding of antibody Y035 and antibody 5A5 to human GPC3 are shown in FIG. 7-8. In different cycles of kinetic assay, the concentration of antibody Y035 was 6.25 nM, 12.5 nM, 25 nM, 50 nM and 100 nM, respectively. The resulting curves were evaluated using Biacore T200 evaluation software and the affinity KD values were calculated. Using the same method, the affinity and kinetic parameters of the parental murine monoclonal antibody 5A5 prior to humanization of Y035 were also assayed. The binding data of antibodies Y035 and 5A5 to human GPC3 proteins, respectively, are summarized in Table 2, and humanized antibody Y035 binds human GPC3 protein much better than mouse 5A5 after humanization.

TABLE 2

Binding kinetic parameter of antibody Y035 and 5A5 to human GPC3

| Antibody | ka (1/Ms) | kd (1/s) | KD (M) |
|---|---|---|---|
| Y035 | 3.96E+05 | 2.51E−05 | 6.34E−11 |
| 5A5 | 2.80E+05 | 2.30E−05 | 8.19E−11 |

5.7 FACS Analysis of Cell-Binding Activity of Antibody Y035

Antibody Y035 was analyzed for binding ability to GPC3-positive hepatocarcinoma HepG2 cell line (ATCC) by Fluorescence Activated Cell Sorter (FACS) using negative 293T (ATCC) cells expressing GPC3 as a negative control.

Specific method is as follows:

1) inoculating HepG2 cells and 297T in logarithmic growth phase into a 6 cm dish respectively at inoculation cell density of about 90%, and incubating overnight at 37° C. in an incubator.

2) digesting cells with 10 mM EDTA, collecting cells through centrifugation at 200 g×5 mins, and resuspending cells in 1% phosphate buffered saline (NBS PBS) containing calf serum at $1×10^6$ to $1×10^7$/mL into a flow-specific tube in an amount of 100 µl per tube.

3) centrifuging at 200 g×5 min, and discarding the supernatant.

4) adding antibodies Y035 to be tested into the experimental groups of both cell lines, respectively, while using PBS without antibody as a blank control. The final concentration of antibody is 20 µg/ml. 100 µl was added to each tube, and incubated in an ice bath for 45 minutes.

5). Adding 2 ml of 1% NBS PBS to each tube and centrifuging at 200 g×5 min for two times.

6) Discarding the supernatant and adding goat anti-human antibody-FITC (Shanghai Karrie Biotech Co., Ltd.) at a dilution of 1:100 with 100 ul being added to each tube, incubating in an ice bath for 45 minutes.

7). Adding 2 ml of 1% NBS PBS into each tube, centrifuging at 200 g×5 min for two times.

8) Discarding the supernatant, resuspending in 300 ul of 1% NBS PBS and detecting by flow cytometry.

Figure 9:
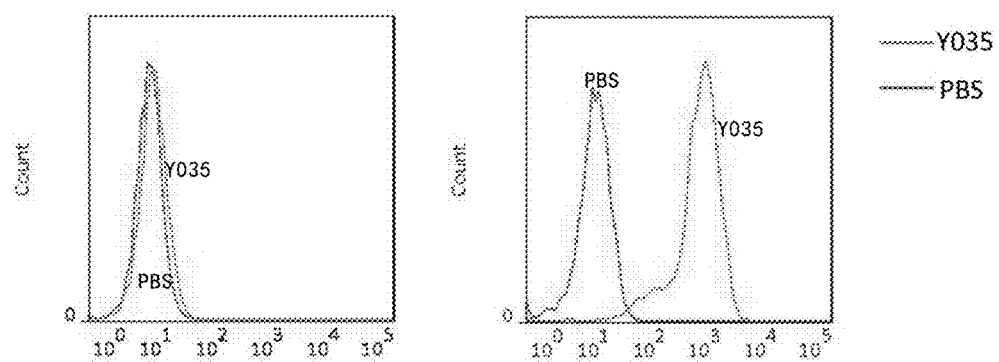
FIG. 9 shows antibody Y035 specifically binding to GPC3-expression positive HepG cells.

Data was analyzed by flow cytometry data analysis software Flowjo7.6, and the results are shown in FIG. 9. Results from flow cytometry show that antibody Y035 can specifically recognize HepG2 cells expressing GPC3, and not bind to GPC3-negative 293T cells.

Example 6. Construction of CAR Expression Vector Based on P7D4 Single Chain Antibody and Preparation of Lentivirus By way of example, the vector system used for the lentiviral plasmid vectors constructed below belongs to self-inactivating lentiviral vector system of the third generation, which has 4 plasmids, namely, packaging plasmid pMDLg RRE encoding protein Gag/Pol (from addgene), packaging plasmid pRSV-REV encoding Rev protein (from addgene); envelope plasmid pCMV-VSV-G encoding VSV-G protein (from addgene); and the recombinant expression vector encoding the gene of interest CAR based on empty vector pRRLSIN-cPPT.PGK-GFP.WPRE (from addgene), which can effectively reduce the risk of forming replicable lentivirus particles.

In the present system, the present inventor firstly modified the empty vector pRRLSIN-cPPT.PGK-GFP.WPRE by the conventional technique of molecular cloning, and replaced the original promoter in the vector with the promoter of elongation factor-1α (EF-1α) and added MluI restriction site between the promoter and CD8αsp signal peptide. Specifically, the vector pWPT-EGFP (purchased from Addgene) was double-digested with ClaI/SalI (purchased from NEB), and a 1.1 kb of DNA fragment was recovered and ligated with T4 DNA ligase into ClaI/SalI digested vector pRRLSIN-cPPT.PGK-GFP.WPRE and transformed into host strain TOP10. The positive clones were picked out by colony PCR and confirmed by sequencing. The recombinant plasmid pRRLSIN-cPPT.EF-1α-EGFP.WPRE was obtained.

Chimeric antigen receptors were prepared using the previously optimized P7D4 scFv. Table 3 explains the connection order of the parts of the chimeric antigen receptor exemplified in the present invention.

TABLE 3

| Chimeric antigen receptor | Extracellular binding region - transmembrane region - intracellular signal region 1 - intracellular signal region 2 and the like | Description |
|---|---|---|
| P7D4-δZ | P7D4 scFv-CD8-CD3δzeta | Negative control |
| P7D4-Z | P7D4 scFv-CD8-CD3 zeta | $1^{st}$ generation |
| P7D4-BBZ | P7D4 scFv-CD8-CD137-CD3 zeta | $2^{nd}$ generation |
| P7D4-28Z | P7D4 scFv-CD28a-CD28b-CD3 zeta | $2^{nd}$ generation |
| P7D4-28BBZ | P7D4 scFv-CD28a-CD28b-CD137-CD3 zeta | $3^{rd}$ generation |

Note:
CD28a represents the transmembrane region of CD28 molecule and CD28b represents the intracellular signaling region of CD28 molecule.

1. Amplification of Nucleic Acid Fragments
(1) Amplification of scFv Sequences

P7D4 scFv fragment was obtained by PCR using V5-scFv-P7D4-Fc plasmid as a template with a forward primer P7D4fd (SEQ ID NO: 36, ctccacgccgccag gccgcaggtgcagctgcaggag, comprising part of the sequence of CD8 signal peptide) and a reverse primer P7D4re (SEQ ID NO: 37, CGGCGCTGGCGTCGTGGT ACCTAGGACGGTGACCTTGG, comprising part of the sequence of CD8 hinge).

(2) Nucleic Acid Sequences of Other Parts of the Chimeric Antigen Receptor

The nucleic acid sequences of other parts of the anti-GPC3 chimeric antigen receptor protein except for P7D4 scFv were respectively obtained by PCR using the sequences SEQ ID NO: 26, 27, 28, 29 and 30 disclosed in Patent Application No. 201310164725.X as templates.

Specifically, the fragment F1 containing the CD8αsp sequence was obtained by PCR amplification with the primer pair PWXLF (SEQ ID NO: 38, gcaggggaaagaatagta-gaca) and PRRL-CD8SP-R1 (SEQ ID NO: 39, CGGCCTGCGGCGTGGAG) using the plasmid pRRLSIN-cPPT.EF-1α-EGFP.WPRE constructed in this example as a template.

Fragment F3-δZ containing CD8-CD3δ zeta (δZ) was obtained by PCR amplification with the primer pair PRRL-CD8hinge (SEQ ID NO: 40, accacgacgccagcgccg) and δZre (SEQ ID NO: 41, GAGGTCGACC-TACGCGGGGGCGTCTGCGCTCCTGCTGAACTT-CACTCT) using the plasmid SEQ ID NO: 26 in 201310164725.X as a template.

Fragment F3-Z comprising CD8-CD3 zeta(Z), fragment F3-BBZ comprising CD8-CD137-CD3 zeta(BBZ), fragment F3-28Z comprising CD28a-CD28b-CD3 zeta(28Z) and fragment F3-28BBZ comprising CD28a-CD28b-CD137-CD3 zeta(28BBZ) was obtained by PCR amplification with the primer pair PRRL-CD8hinge (SEQ ID NO: 42, accacgacgccagcgccg) and R3R (SEQ ID NO: 43, aatccagaggttgattgtcgacctagcgaggggggcagggcctgc) using the plasmids corresponding to SEQ ID NO: 27, SEQ ID NO: 28, SEQ ID NO: 29 and SEQ ID NO: 30 in the application No. 201310164725.X, respectively.

2. Splicing of Nucleic Acid Fragments

F1 nucleic acid fragment obtained as described above and equimolar P7D4 scFv nucleic acid fragment and equimolar F3-δZ or F3-Z or F3-BBZ or F3-28Z or F3-28BBZ nucleic acid fragments were subjected to three-segment splicing and PCR as shown in FIG. 9 under the following conditions: Pre-denaturation: 94° C. for 4 min; denaturation: 94° C. for 40 s; annealing: 60° C. for 40 s; extension: 68° C. for 140 s for 5 cycles and then total extension 68° C. for 10 min. DNA polymerase and forward primer PWXLF and reverse primer R3R (reverse primer corresponding to CD8-CD3δ zeta was δZ re, and other is R3R) were supplemented, and then PCR was performed for 30 cycles with the amplification conditions: Pre-denaturation: 94° C. for 4 min; denaturation: 94° C. for 40 s; annealing: 60° C. for 40 s; extension: 68° C. for 140 s for 30 cycles and then total extension 68° C. for 10 min. The fragment consisting of F1 fragment, P7D4 scFv or P7D4 mutant scFv, and various F3 fragments constructed in this Example may be simply referred to as CAR fragment, and the amplified fragments were referred to as:

| P7D4 scFv-δZ    | (SEQ ID NO: 44), |
| P7D4 scFv-Z     | (SEQ ID NO: 45), |
| P7D4 scFv-BBZ   | (SEQ ID NO: 46), |
| P7D4 scFv-28Z   | (SEQ ID NO: 47), |
| P7D4 scFv-28BBZ | (SEQ ID NO: 48). |

3. Construction of Lentiviral Plasmid Vector

In this example, target gene consisting of F1 fragment, P7D4 scFv and F3 fragment components (abbreviated as CAR) was double-digested by MluI and SalI restriction enzymes and ligated into the same double digested pRRLSIN-cPPT.EF-1α-EGFP.WPRE vector to construct a lentiviral vector expressing each chimeric antigen receptor. The constructed vector was identified by MluI and SalI digestion and sequenced correctly, which was ready for lentivirus packaging. As mentioned above, the relevant CAR gene was transcribed and translated into one peptide chain, where the anti-GPC3 chimeric antigen receptor will be localized under the guidance of CD8α signal peptide on the cell membrane.

5 CAR polypeptide sequences were respectively obtained through the above construction, which are named as:

P7D4-δZ (SEQ ID NO: 49);
P7D4-Z (SEQ ID NO: 50);
P7D4-BBZ (SEQ ID NO: 51);
P7D4-28Z (SEQ ID NO: 52);
P7D4-28BBZ (SEQ ID NO: 53).

4. Plasmid-Transfected 293T Packaging Lentivirus

HEK-293T cells (ATCC: CRL-11268) cultured at passage 6 to passage 10 were seeded at a density of $6 \times 10^6$ in 10 cm dishes and cultured overnight at 37° C. in 5% $CO_2$ for transfection. The medium was DMEM containing 10% fetal bovine serum (purchased from Life).

Transfection steps are as follows:

4.1 Preparation of liquid A: dissolving 5.2 µg of each of the desired gene plasmids pRRLSIN-cPPT.EF-1α-CAR with 6.2 µg of packaging plasmid pMDLg RRE and pRSV-REV and 2.4 µg of envelope plasmid pCMV-VSV-G into 800 µL of serum-free DMEM medium and mixing well.

4.2 Preparation of liquid B: dissolving 60 µg PEI (polyethylenimine 1 µg/µl, purchased from Polysciences) in 800 µL serum-free DMEM medium, mixing gently and incubating at room temperature for 5 min.

4.3 Formation of transfection complex: adding liquid A into liquid B and gently mixing, vortexing or gently mixing immediately after addition, incubating at room temperature for 20 min.

4.4 Adding 1.6 ml of the transfection complex into HEK-293T cells dropwise, and after 4-5 h, changing to DMEM with 2% FBS for transfected 293T cells.

After 72 h of transfection, the virus was collected by filtration using a 0.45 µm filter (available from Millipore Corporation) and centrifuged at 28,000 rpm using a Beckman Optima L-100XP ultracentrifuge for 2 hours at 4° C. The supernatant was discarded and the resulting pellet was centrifuged at $\frac{1}{10} \sim \frac{1}{50}$ stock solution of AIM-V (purchased from Life) and resuspend at 100 µL/tube in −80° C. for virus titration or infection of T lymphocytes.

Example 7. T Cells Infected by Recombinant Lentivirus

Human peripheral blood mononuclear cells were obtained from healthy human peripheral blood by density gradient centrifugation (supplied by Shanghai Blood Center) and added in AIM-V lymphocyte medium (purchased from Invitrogen) at a density of about $2 \times 10^6$/mL and added. The magnetic beads coated with anti-CD3 and CD28 antibodies (Invitrogen) were added in a 1:1 ratio of cells to magnetic beads, and recombinant human IL-2 (purchased from Shanghai Huaxin Biotechnology Co., Ltd.) at a final concentration of 300 U/mL was added for stimulation and culture for 48 h. And then T cells were infected with the above recombinant lentivirus (MOI≈10). The infected cells were passaged every other day at a density of $5 \times 10^5$/mL and recombinant human IL-2 at a final concentration of 300 U/mL was supplemented in the lymphocyte culture medium.

Infected CTL cells were detected by flow cytometry on day 8 of culture for the expression of different chimeric antigen receptors. FACS assays were performed using His-tagged human GPC3 recombinant protein (purchased from Shanghai Rui Jin Biotech Co., Ltd.); the cells were firstly incubated with the protein (50 ug/ml) for 1 hr, washed twice with D-PBS, and Anti-His-tag antibody (1:50 dilution, purchased from Shanghai Reagent Biotechnology Co., Ltd.) was added and incubated for 1 hr and then washed twice with D-PBS and then FITC labeled goat anti-mouse secondary antibody (Shanghai Kangcheng Biotechnology Co., Ltd.), incubated for 50 min, washed with D-PBS for three times, and tested by FACS. Uninfected T lymphocytes was used as a negative control, the positive rates of virus-infected T cells expressing different chimeric antigen receptors are shown in Table 4. The positive rate results show that a certain positive rate of $CAR^+T$ cells can be obtained by lentivirus infection.

TABLE 4

| T cells transfected by following CARs | Positive rate of T cells transfection |
|---|---|
| P7D4-δZ (negative control) | 59% |
| P7D4-Z | 65% |
| P7D4-BBZ | 53% |
| P7D4-28Z | 61% |
| P7D4-28BBZ | 54% |

T cells were infected with viruses that had different chimeric antigen receptors packaged, respectively, and then subcultured at a cell density of 5×10⁵/ml quaque die alterna, counted, and supplemented with IL-2 (final concentration of 300 U/ml). On the 11th day of culture, about 100~1000 times of amplification was obtained, indicating that the T cells expressing different chimeric antigen receptors can be expanded in a certain amount in vitro, which ensures subsequent in vitro toxicity tests and in vivo experiments.

Example 8. In Vitro Toxicity Test of T Lymphocytes Expressing Chimeric Antigen Receptors In vitro toxicity experiments used the following materials: GPC3-positive hepatoma cells (HepG2 and Huh-7) and GPC3-negative hepatoma cells (SK-HEP-1) as shown in Specifically, as shown in Table 5, the CAR of the P7D4 single chain antibody of the present invention exhibited significant killing activity on GPC3-positive hepatoma cells, and the second and third generations of P7D4 CAR T cells were slightly more potent than the antitumor activity of the first generation. In addition, all CAR T cells showed no cytotoxic activity on GPC3-negative SK-HEP-1 positive hepatoma cells. These results indicate that P7D4 can selectively target GPC3-positive hepatoma cells and kill them effectively. In addition, the first, second and third generation of CART expressing P7D4 of the present invention exhibited a effector target ratio gradient dependency, that is, the higher the effector target ratio, the stronger the cytotoxic effects.

TABLE 5

Cytotoxicity of CAR T cells expressing the single chain antibody P7D4

| Cytotoxicity | P7D4-28BBZ Different effector target ratio | | | P7D4-BBZ Different effector target ratio | | | P7D4-28Z Different effector target ratio | | | P7D4-Z Different effector target ratio | | | P7D4-δZ Different effector target ratio | | |
|---|---|---|---|---|---|---|---|---|---|---|---|---|---|---|---|
| (%) | 3:1 | 1:1 | 1:3 | 3:1 | 1:1 | 1:3 | 3:1 | 1:1 | 1:3 | 3:1 | 1:1 | 1:3 | 3:1 | 1:1 | 1:3 |
| HuH-7 | 75.3 | 48.4 | 17.2 | 69.2 | 32.2 | 10.2 | 62.4 | 31.3 | 7.8 | 42.9 | 20.2 | 5.6 | 3.2 | 1.3 | 5.3 |
| HepG2 | 85.8 | 59.1 | 21.9 | 71.3 | 38.6 | 13.9 | 68.2 | 35.6 | 6.5 | 48.5 | 25.9 | 7.2 | 4.8 | 2.5 | 3.2 |
| SK-HEP-1 | 2.5 | 3.2 | 3.9 | 4.5 | 2.1 | 3.8 | 1.9 | 2.4 | 3.6 | 2.3 | 3.7 | 4.8 | 3.1 | 2.3 | 1.2 |

Table 5 were used as target cells and effector cells were CTL cultured for 12 days in vitro, which were verified in Example 7 and detected chimeric antigen receptor-expression positive by FACS. Effective target ratios were 3:1, 1:1 and 1:3, respectively. The number of target cells was 10000/well, and effector cells corresponded to different effective target ratio. Each group had 5 replicate wells, average of 5 wells was calculated, and detection time was 18 h.

Each experimental group and each control group are listed as follows:

Each experimental group: each target cell+CTL expressing different chimeric antigen receptors;

Control group 1: target cells with maxium LDH release;
Control group 2: target cells with spontaneous LDH release;
Control group 3: effector cells with spontaneous LDH release.

Detection method: CytoTox 96® Non-Radioactive Cytotoxicity Assay (Promega) is used, which is a colorimetric based assay that can replace 51Cr release assay. CytoTox 96® Assay measures lactate dehydrogenase (LDH) quantitatively. LDH is a stable cytosolic enzyme that is released upon lysis of cells and is released in the same way as radioactive 51Cr is released. The supernatant with released LDH medium can be detected by a 30-minute coupled enzyme reaction in which LDH converts a tetrazolium salt (INT) to a red formazan. The amount of red product produced is proportional to the number of lysed cells. Details can be found in instructions of CytoTox 96 non-radioactive cytotoxicity detection kit.

Cytotoxicity is calculated as:

Cytotoxicity %=[(experiment group−control group 2−control group 3)/(control group 1−control group 2)]×100

Example 9. Preparation and Comparison of CAR-T Cells Based on Y035 and GC33

Two types of CAR-T cells, Y035-BBZ, Y035-28Z and Y035-28BBZ, were prepared based on the light chain variable region and the heavy chain variable region of Y035, respectively, according to the procedures of Examples 6 and 7; and two CAR-T cells, GC33-28Z and GC33-28BBZ, were prepared based on light chain variable region and heavy chain variable region of GC33, as a control. Parts of the chimeric antigen receptor are connected as shown in Table 6.

TABLE 6

| Chimeric antigen receptor | Extracellular binding region - transmembrane region - intracellular signal region 1 - intracellular signal region 2 and the like |
|---|---|
| Y035-BBZ | Y035 scFv-CD8-CD137-CD3 zeta |
| Y035-28Z | Y035 scFv-CD28a-CD28b-CD3 zeta |
| Y035-28BBZ | Y035 scFv-CD28a-CD28b-CD137-CD3 zeta |
| GC33-28Z | GC33 scFv-CD28a-CD28b-CD3 zeta |
| GC33-28BBZ | GC33 scFv-CD28a-CD28b-CD137-CD3 zeta |

```
Wherein nucleotide sequence of Y035-BBZ is show as
follows (SEQ ID NO: 85):
gaggtgcagctggtgcagagcggcgccgaggtgaagaagcccggcgccag cgtgaaggtgagctgcaaggccagcggctacaccttcagcgactacgaga tgcactgggtgcggcaggccccggccagggcctggagtggatgggcgcc atccacccggcagcggcgacaccgcctacaaccagcggttcaagggccg ggtgaccatcaccgccgacaagagcaccagcaccgcctacatggagctga
```

```
gcagcctgcggagcgaggacaccgccgtgtactactgcgcccggttctac agctacgcctactggggccagggcaccctggtgaccgtgagcgccggtgg aggcggttcaggcggaggtggttctggcggtggcggatcggacatcgtga tgacccagacccccctgagcctgcccgtgaccccggcgagcccgccagc atcagctgccggagcagccagagcctggtgcacagcaacggcaacaccta cctgcagtggtacctgcagaagcccggccagagccccagctgctgatct acaaggtgagcaaccggttcagcggcgtgcccgaccggttcagcggcagc ggcagcggcaccgacttcacccctgaagatcagccgggtggaggccgagga cgtgggcgtgtactactgcagccagagcatctacgtgccctacaccttcg gccagggcaccaagctggagatcaaacgtaccacgacgccagcgccgcga ccaccaacaccggcgccaccatcgcgtcgcagcccctgtccctgcgccc agaggcgtgccggccagcggcggggggcgcagtgcacacgagggggctgg acttcgcctgtgatatctacatctgggcgccttggccgggacttgtggg gtccttctcctgtcactggttatcaccctttactgcaaacggggcagaaa gaaactcctgtatatattcaaacaaccatttatgagaccagtacaaacta ctcaagaggaagatggctgtagctgccgatttccagaagaagaagaagga ggatgtgaactgagagtgaagttcagcaggagcgcagacgccccgcgta caagcagggccagaaccagctctataacgagctcaatctaggacgaagag aggagtacgatgtttttggacaagagacgtggccgggaccctgagatgggg ggaaagccgagaaggaagaaccctcaggaaggcctgtacaatgaactgca gaaagataagatggcggaggcctacagtgagattgggatgaaaggcgagc gccggaggggcaaggggcacgatggcctttaccagggtctcagtacagcc accaaggacacctacgacgcccttcacatgcaggccctgcccctcgc amino acid sequence of Y035-BBZ is shown as
follows (SEQ ID NO: 86)
EVQLVQSGAEVKKPGASVKVSCKASGYTFSDYEMHWVRQAPGQGLEWMGA

IHPGSGDTAYNQRFKGRVTITADKSTSTAYMELSSLRSEDTAVYYCARFY

SYAYWGQGTLVTVSAGGGGSGGGGSGGGGSDIVMTQTPLSLPVTPGEPAS

ISCRSSQSLVHSNGNTYLQWYLQKPGQSPQLLIYKVSNRFSGVPDRFSGS

GSGTDFTLKISRVEAEDVGVYYCSQSIYVPYTFGQGTKLEIKRTTTPAPR

PPTPAPTIASQPLSLRPEACRPAAGGAVHTRGLDFACDIYIWAPLAGTCG

VLLLSLVITLYCKRGRKKLLYIFKQPFMRPVQTTQEEDGCSCRFPEEEEG

GCELRVKFSRSADAPAYKQGQNQLYNELNLGRREEYDVLDKRRGRDPEMG

GKPRRKNPQEGLYNELQKDKMAEAYSEIGMKGERRRGKGHDGLYQGLSTA

TKDTYDALHMQALPPR nucleotide sequence of Y035-28Z is shown as
follows (SEQ ID NO: 87):
gaggtgcagctggtgcagagcggcgccgaggtgaagaagcccggcgccag cgtgaaggtgagctgcaaggccagcggctacaccttcagcgactacgaga tgcactgggtgcggcaggcccccggccagggcctggagtggatgggcgcc atccaccccggcagcggcgacaccgcctacaaccagcggttcaagggccg ggtgaccatcaccgccgacaagagcaccagcaccgcctacatggagctga gcagcctgcggagcgaggacaccgccgtgtactactgcgcccggttctac agctacgcctactggggccagggcaccctggtgaccgtgagcgccggtgg aggcggttcaggcggaggtggttctggcggtggcggatcggacatcgtga tgacccagacccccctgagcctgcccgtgaccccggcgagcccgccagc atcagctgccggagcagccagagcctggtgcacagcaacggcaacaccta cctgcagtggtacctgcagaagcccggccagagccccagctgctgatct acaaggtgagcaaccggttcagcggcgtgcccgaccggttcagcggcagc ggcagcggcaccgacttcacccctgaagatcagccgggtggaggccgagga cgtgggcgtgtactactgcagccagagcatctacgtgccctacaccttcg gccagggcaccaagctggagatcaaacgtaccacgacgccagcgccgcga ccaccaacaccggcgccaccatcgcgtcgcagcccctgtccctgcgccc agaggcgtgccggccagcggcggggggcgcagtgcacacgagggggctgg acttcgcctgtgattttggtgctggtggtggttggtggagtcctggct tgctatagcttgctagtaacagtggcctttattattttctgggtgaggag taagaggagcaggctcctgcacagtgactacatgaacatgactccccgcc gccccgggccaacccgcaagcattaccagccctatgccccaccacgcgac ttcgcagcctatcgctccagagtgaagttcagcaggagcgcagacgcccc cgcgtaccagcagggccagaaccagctctataacgagctcaatctaggac gaagagaggagtacgatgtttttggacaagagacgtggccgggaccctgag atggggggaaagccgcagagaaggaagaaccctcaggaaggcctgtacaa tgaactgcagaaagataagatggcggaggcctacagtgagattgggatga aaggcgagcgccggaggggcaaggggcacgatggcctttaccagggtctc agtacagccaccaaggacacctacgacgcccttcacatgcaggccctgcc ccctcgc amino acid sequence of Y035-28Z is shown as
follows (SEQ ID NO: 88):
EVQLVQSGAEVKKPGASVKVSCKASGYTFSDYEMHWVRQAPGQGLEWMGA

IHPGSGDTAYNQRFKGRVTITADKSTSTAYMELSSLRSEDTAVYYCARFY

SYAYWGQGTLVTVSAGGGGSGGGGSGGGGSDIVMTQTPLSLPVTPGEPAS

ISCRSSQSLVHSNGNTYLQWYLQKPGQSPQLLIYKVSNRFSGVPDRFSGS

GSGTDFTLKISRVEAEDVGVYYCSQSIYVPYTFGQGTKLEIKRTTTPAPR

PPTPAPTIASQPLSLRPEACRPAAGGAVHTRGLDFACDFWVLVVVGGVLA

CYSLLVTVAFIIFWVRSKRSRLLHSDYMNMTPRRPGPTRKHYQPYAPPRD

FAAYRSRVKFSRSADAPAYQQGQNQLYNELNLGRREEYDVLDKRRGRDPE

MGGKPQRRKNPQEGLYNELQKDKMAEAYSEIGMKGERRRGKGHDGLYQGL

STATKDTYDALHMQALPPR nucleotide sequence of Y035-28BBZ is shown as
follows (SEQ ID NO: 89):
gaggtgcagctggtgcagagcggcgccgaggtgaagaagcccggcgccag cgtgaaggtgagctgcaaggccagcggctacaccttcagcgactacgaga tgcactgggtgcggcaggcccccggccagggcctggagtggatgggcgcc atccaccccggcagcggcgacaccgcctacaaccagcggttcaagggccg ggtgaccatcaccgccgacaagagcaccagcaccgcctacatggagctga
```

-continued
```
gcagcctgcggagcgaggacaccgccgtgtactactgcgcccggttctac agctacgcctactggggccagggcaccctggtgaccgtgagcgccggtgg aggcggttcaggcggaggtggttctggcggtggcggatcggacatcgtga tgacccagacccccctgagcctgcccgtgaccccggcgagcccgccagc atcagctgccggagcagccagagcctggtgcacagcaacggcaaccta cctgcagtggtacctgcagaagcccggccagagccccagctgctgatct acaaggtgagcaaccggttcagcggcgtgcccgaccggttcagcggcagc ggcagcggcaccgacttcaccctgaagatcagccgggtggaggccgagga cgtgggcgtgtactactgcagccagagcatctacgtgccctacaccttcg gccagggcaccaagctggagatcaaacgtaccacgacgccagcgccgca ccaccaacaccggcgcccaccatcgcgtcgcagccctgtccctgcgcc agaggcgtgccggccagcggcggggggcgcagtgcacacgaggggctgg acttcgcctgtgattttgggtgctggtggtggttggtggagtcctggct tgctatagcttgctagtaacagtggcctttattattttctgggtgaggag taagaggagcaggctcctgcacagtgactacatgaacatgactccccgcc gccccgggccaacccgcaagcattaccagccctatgccccaccacgcgac ttcgcagcctatcgctccaaacggggcagaaagaaactcctgtatatatt caaacaaccatttatgagaccagtacaaactactcaagaggaagatggct gtagctgccgatttccagaagaagaagaaggaggatgtgaactgagagtg aagttcagcaggagcgcagacgccccgcgtaccagcagggccagaacca gctctataacgagctcaatctaggacgaagagaggagtacgatgttttgg acaagagacgtggccgggaccctgagatgggggaaagccgcagagaagg aagaaccctcaggaaggcctgtacaatgaactgcagaaagataagatggc ggaggcctacagtgagattgggatgaaaggcgagcgccggaggggcaagg ggcacgatggccttaccagggtctcagtacagccaccaaggacacctac gacgccttcacatgcaggccctgccccctcgc amino acid sequence of Y035-28BBZ is shown as
follows (SEQ ID NO: 90)
EVQLVQSGAEVKKPGASVKVSCKASGYTFSDYEMHWVRQAPGQGLEWMGA

IHPGSGDTAYNQRFKGRVTITADKSTSTAYMELSSLRSEDTAVYYCARFY

SYAYWGQGTLVTVSAGGGGSGGGGSGGGGSDIVMTQTPLSLPVTPGEPAS

ISCRSSQSLVHSNGNTYLQWYLQKPGQSPQLLIYKVSNRFSGVPDRFSGS

GSGTDFTLKISRVEAEDVGVYYCSQSIYVPYTFGQGTKLEIKRTTTPAPR

PPTPAPTIASQPLSLRPEACRPAAGGAVHTRGLDFACDFWVLVVVGGVLA

CYSLLVTVAFIIFWVRSKRSRLLHSDYMNMTPRRPGPTRKHYQPYAPPRD

FAAYRSKRGRKKLLYIFKQPFMRPVQTTQEEDGCSCRFPEEEEGGCELRV

KFSRSADAPAYQQGQNQLYNELNLGRREEYDVLDKRRGRDPEMGGKPQRR

KNPQEGLYNELQKDKMAEAYSEIGMKGERRRGKGHDGLYQGLSTATKDTY

DALHMQALPPR
```

GPC3-positive hepatoma Huh-7 cells were used as target cells and in vitro toxicity test was conducted according to the in vitro toxicity test method of Example 8. When the effector target ratio was 1:3, the killing rates Y035-28Z and Y035-28BBZ on Huh-7 can be over 35%, the killing rate of GC33-28Z was only 6%, and the killing rate of GC33-28BZZ was only 23%. When the effector target ratio was 1:1, the killing rate of Y035-28Z on Huh-7 can be over 60% %, While the killing rate of GC33-28Z was only 22%. The above results show that the cell-killing activity of Y035-CAR T cells of the present application was significantly better than that of GC33-CAR T cells.

Example 10. Preparation of Bispecific Antibody Called Bispecific T Cell Engager (BiTE)

(1) Preparation of the Nucleotide Sequence of Y035 Single-Chain Antibody

The hybridoma cell line secreting the monoclonal antibody was cultured to logarithmic growth phase, and cells were counted, and 1×10⁷ hybridoma cells were taken. Total RNA was extracted from the cell pellet according to instruction of TRIzol® Plus RNA Purification kit (Invitrogen, 12183-555).

a. cDNA Obtained by Reverse Transcription

Total RNAs of hybridoma cells were used as a template and cDNA was synthesized by reverse transcription using High capacity RNA to cDNA kit (Invitrogen, 4387406).

b. Amplification of Antibody Variable Region by 5'-RACE Method

The cDNA was used as a template and amplified with primers tgctttggtttccaggtgcaagatgtgaggtgcagctggtcgaga (SEQ ID NO: 91) and primer TATCGGATCCACCACCTC-CACGTTTGATCTCCAGCTTGGTG (SEQ ID NO: 92) using 5'-Full RACE kit (TAKARA, D315). The PCR product was separated by 1.5% agarose gel electrophoresis, and the obtained PCR product was Y035 single-chain antibody nucleic acid.

(2) Construction of CD3 Single Chain Antibody Nucleic Acid Sequence

PCR was performed with primer (SEQ ID NO: 93, gatatcaaactgcagcagtcag) and primer (SEQ ID NO: 94, GAGAGGGAGTACTCACCCCAAC) using the anti-Ep-CAM/CD3 bispecific antibody disclosed in 201310025302.X as a template with reference to KOD PLUS Enzyme Manual. The gel was recovered and purified, and the obtained PCR product was a nucleic acid of CD3 single-chain antibody.

(3) Introduction of NheI Restriction Sites

PCR was performed with primers (ggctaactagagaacc-cactgc, SEQ ID NO: 95) and PH-R (ACATCTTGCACCTG-GAAACCAAAGC, SEQ ID NO: 96) using vector PIH as a template, and specific reaction can refer to KOD PLUS Enzyme Manual. Gel was recovered and the PCR product was purified, thereby obtaining a short fragment with NheI restriction site.

(4) Construction of Coding Sequence Nucleic Acid of Y035/CD3 Bispecific Antibody Overlap PCR was performed using the PCR products obtained in steps (1), (2) and (3), and PCR was performed with primer (SEQ ID NO: 95) and primer (SEQ ID NO: 92). Gel was recovered and the PCR product was purified, thereby obtaining Y035/CD3 bispecific antibody coding sequence (SEQ ID NO: 97) with the following sequence:

```
gaggtgcagctggtgcagagcggcgccgaggtgaagaagcccggcgccag cgtgaaggtgagctgcaaggccagcggctacaccttcagcgactacgaga tgcactgggtgcggcaggcccccggccagggcctggagtggatgggcgcc
```

```
atccaccccggcagcggcgacaccgcctacaaccagcggttcaagggccg ggtgaccatcaccgccgacaagagcaccagcaccgcctacatggagctga gcagcctgcggagcgaggacaccgccgtgtactactgcgcccggttctac agctacgcctactggggccagggcaccctggtgaccgtgagcgccggtgg aggcggttcaggcggaggtggttctggcggtggcggatcggacatcgtga tgacccagacccccctgagcctgcccgtgaccccggcgagcccgccagc atcagctgccggagcagccagagcctggtgcacagcaacggcaacaccta cctgcagtggtacctgcagaagcccggccagagcccccagctgctgatct acaaggtgagcaaccggttcagcggcgtgcccgaccggttcagcggcagc ggcagcggcaccgacttcaccctgaagatcagccgggtggaggccgagga cgtgggcgtgtactactgcagccagagcatctacgtgccctacaccttcg gccagggcaccaagctggagatcaaacgtggaggtggtggatccgatatc aaactgcagcagtcagggggctgaactggcaagacctgggcctcagtgaa gatgtcctgcaagacttctggctacacctttactaggtacacgatgcact gggtaaaacagaggcctggacagggtctggaatggattggatacattaat cctagccgtggttatactaattacaatcagaagttcaaggacaaggccac attgactacagacaaatcctccagcacagcctacatgcaactgagcagcc tgacatctgaggactctgcagtctattactgtgcaagatattatgatgat cattactgccttgactactggggccaaggcaccactctcacagtctcctc agtcgaaggtggaagtggaggttctggtggaagtggaggttcaggtggag tcgacgacattcagctgacccagtctccagcaatcatgtctgcatctcca ggggagaaggtcaccatgacctgcagagccagttcaagtgtaagttacat gaactggtaccagcagaagtcaggcacctcccccaaaagatggatttatg acacatccaaagtggcttctggagtcccttatcgcttcagtggcagtggg tctgggacctcatactctctcacaatcagcagcatggaggctgaagatgc tgccacttattactgccaacagtggagtagtaaccccgctcacgttcggtg ctgggaccaagctggagctgaaa
```

(5) Expression and Purification of Bispecific Antibodies Targeting Y035/CD3

Plasmids of Y035/CD3 BiTE were transiently transfected into eukaryotic cells 293F and cell transfection was performed with reference to 293 fectin instruction. The culture supernatant was purified by NiSepharose™ 6 Fast Flow (purchased from GE Healthcare Bio-Science), a metal affinity chromatography column, to give the bispecific antibody of Y035/CD3 (SEQ ID NO: 98) with the following sequence:

EVQLVQSGAEVKKPGASVKVSCKASGYTFSDYEMHWVRQAPGQGLEWMGA

IHPGSGDTAYNQRFKGRVTITADKSTSTAYMELSSLRSEDTAVYYCARFY

SYAYWGQGTLVTVSAGGGGSGGGGSGGGGSDIVMTQTPLSLPVTPGEPAS

ISCRSSQSLVHSNGNTYLQWYLQKPGQSPQLLIYKVSNRFSGVPDRFSGS

GSGTDFTLKISRVEAEDVGVYYCSQSIYVPYTFGQGTKLEIKRGGGGSDI

KLQQSGAELARPGASVKMSCKTSGYTFTRYTMHWVKQRPGQGLEWIGYIN

PSRGYTNYNQKFKDKATLTTDKSSSTAYMQLSSLTSEDSAVYYCARYYDD

HYCLDYWGQGTTLTVSSVEGGSGGSGGSGGSGGVDDIQLTQSPAIMSASP

GEKVTMTCRASSSVSYMNWYQQKSGTSPKRWIYDTSKVASGVPYRFSGSG

SGTSYSLTISSMEAEDAATYYCQQWSSNPLTFGAGTKLELK

GPC3-positive HepG2 and SK-Hep-1 GPC3 cells were selected for studying in vitro cytotoxicity of Y035/CD3 BiTE. Results shows that the cytotoxicity of Y035/CD3 BiTE at a concentration of 0.1 ng/ml on HepG2 cells can reach about 60% and the cytotoxicity on SK-Hep-1 GPC3 can reach about 40%. Compared with GPC3/CD3 BiTE described in CN103833852A, cytotoxicity of Y035/CD3 BiTE is significantly increased.

All references mentioned in the present application are incorporated herein by reference, as if each reference was individually incorporated by reference. In addition, it should be understood that after reading the above teachings of the present invention, those skilled in the art can make various modifications or changes to the present invention, and such equivalent forms also fall within the scope of the appended claims of the present application.

The invention claimed is:

1. An antibody that specifically recognizes glypican-3, comprising within an antibody molecule:
a light chain variable region comprising $V_L$ CDR1 having the sequence of SEQ ID NO: 16, $V_L$ CDR2 having the sequence of SEQ ID NO: 18, and $V_L$ CDR3 having the sequence of SEQ ID NO: 20; and a heavy chain variable region comprising $V_H$ CDR1 having the sequence of SEQ ID NO: 10, $V_H$ CDR2 having the sequence of SEQ ID NO: 12, and $V_H$ CDR3 having the sequence of SEQ ID NO: 14.

2. The antibody of claim 1, wherein the heavy chain variable region of the antibody has the sequence shown in positions 1-121 of SEQ ID NO: 4, and the light chain variable region of the antibody has the sequence shown in positions 137-247 of SEQ ID NO: 4.

3. A multifunctional immunoconjugate, comprising:
the antibody of claim 1; and
a functional molecule linked thereto,
wherein the functional molecule includes at least one selected from the group consisting of a molecule targeting a tumor surface marker, a tumor-suppressing molecule, a molecule targeting a surface marker of an immune cell, and a detectable label, and
wherein the immune cell comprises a T lymphocyte, an NK cell or an NKT cell.

4. The multifunctional immunoconjugate of claim 3, wherein the molecule targeting the tumor surface marker is an antibody or ligand that binds to the tumor surface marker; or
the tumor-suppressing molecule is an anti-tumor cytokine or anti-tumor toxin, and the anti-tumor cytokine includes at least one selected from the group consisting of IL-12, IL-15, IFN-beta, and TNF-alpha.

5. The multifunctional immunoconjugate of claim 3, wherein the detectable label includes a fluorescent label or a chromogenic label.

6. The multifunctional immunoconjugate of claim 4, wherein the antibody that binds to the tumor surface marker is an antibody that recognizes an antigen other than glypican-3, wherein the antigen includes EGFR, EGFRvIII, mesothelin, HER2, EphA2, Her3, EpCAM, MUC1, MUC16, CEA, Claudin 18.2, folate receptor, Claudin 6, WT1, NY-ESO-1, MAGE 3, ASGPR1, or CDH16.

7. The multifunctional immunoconjugate of claim 3, wherein the immune cell comprises a T lymphocyte, an NK cell or an NKT cell, and
wherein the molecule targeting the surface marker of the immune cell is an antibody that binds to a T cell surface marker, thereby forming a T-cell-engaging bifunctional antibody with the antibody of claim 1.

8. The multifunctional immunoconjugate of claim 7, wherein the antibody that binds to the immune cell surface marker is an anti-CD3 antibody.

9. The multifunctional immunoconjugate of claim 3, wherein the multifunctional immunoconjugate is a fusion peptide, and further comprises a linker peptide between the antibody and the functional molecule linked thereto.

10. A chimeric antigen receptor, comprising
the antibody of claim 1, a transmembrane region, and an intracellular signal region.

11. The chimeric antigen receptor of claim 10, wherein the transmembrane region comprises a transmembrane region of CD8 or CD28.

12. The chimeric antigen receptor of claim 11, comprising:
a) the antibody of claim 2, the transmembrane region of CD8, and the intracellular signal region of CD3ζ; or
b) the antibody of claim 2, the transmembrane region of CD8, the intracellular signal region of CD137, and the intracellular signal region of CD3ζ; or
c) the antibody of claim 2, the transmembrane region of CD28 molecule, the intracellular signaling region of CD28 molecule, and the intracellular signal region of CD3ζ; or
d) the antibody of claim 2, the transmembrane region of CD28 molecule, the intracellular signaling region of CD28 molecule, the intracellular signal region of CD137, and the intracellular signal region of CD3ζ.

13. The chimeric antigen receptor of claim 10, wherein the antibody is a single chain antibody.

14. The chimeric antigen receptor of claim 10, wherein the chimeric antigen receptor comprises:
SEQ ID NO: 49 or the amino acid sequence shown in positions 22-346 thereof;
SEQ ID NO: 50 or the amino acid sequence shown in positions 22-447 thereof;
SEQ ID NO: 51 or the amino acid sequence shown in positions 22-491 thereof;

SEQ ID NO: 52 or the amino acid sequence shown in positions 22-494 thereof; or

SEQ ID NO: 53 or the amino acid sequence shown in positions 22-536 thereof.

15. An isolated genetically modified immune cell, comprising the chimeric antigen receptor of claim 10.

16. The isolated genetically modified immune cell of claim 15, further comprising an exogenous encoding sequence for a cytokine.

17. The isolated genetically modified immune cell of claim 15, further comprising another chimeric antigen receptor which does not contain CD3ζ but contains the intracellular signaling domain of CD28, or the intracellular signaling domain of CD137, or a combination of both.

18. The isolated genetically modified immune cell of claim 15, further comprising a chemokine receptor.

19. The isolated genetically modified immune cell of claim 15, wherein the genetically modified immune cell is a modified T lymphocyte, NK cell or NKT cell.

20. A method for preparing a drug inhibiting a tumor expressing glypican-3, comprising a step of:
mixing the genetically modified immune cell of claim 15 with a pharmaceutically acceptable carrier.

21. A pharmaceutical composition comprising:
an antibody that specifically recognizes glypican-3; or
an immunoconjugate;
and a pharmaceutically acceptable carrier;
wherein the immunoconjugate comprises the antibody and a functional molecule linked thereto, and the antibody comprises within an antibody molecule:

a light chain variable region comprising $V_L$ CDR1 having the sequence of SEQ ID NO: 16, $V_L$ CDR2 having the sequence of SEQ ID NO: 18, and $V_L$ CDR3 having the sequence of SEQ ID NO: 20; and a heavy chain variable region comprising $V_H$ CDR1 having the sequence of SEQ ID NO: 10, $V_H$ CDR2 having the sequence of SEQ ID NO: 12, and $V_H$ CDR3 having the sequence of SEQ ID NO: 14.

22. The isolated genetically modified immune cell of claim 18, wherein the chemokine receptor includes CCR2.

23. The chimeric antigen receptor of claim 10, wherein the intracellular signal region includes at least one intracellular signal region sequence selected from the group consisting of CD3ζ, FcεRIγ, CD27, CD28, CD137, CD134, MyD88, and CD40.

24. The antibody of claim 2, wherein the antibody is a single chain antibody.

25. The antibody of claim 24, wherein the single chain antibody is an scFv.

26. The antibody of claim 25, wherein the scFv comprises SEQ ID NO: 4.

* * * * *

SEQUENCE LISTING

<160> NUMBER OF SEQ ID NOS: 99

<210> SEQ ID NO 1
<211> LENGTH: 729
<212> TYPE: DNA
<213> ORGANISM: Artificial sequence
<220> FEATURE:
<223> OTHER INFORMATION: Nucleotide sequence of single chain antibody P1B12E

<400> SEQUENCE: 1

```
caggtgcagc tggtggaatc tgggggctgag gtgaagaagc ctggggcctc agtgaaggtc      60
tcctgcaagg cttctggagg caccttcagc agctatgcta tcagctgggt gcgacaggcc     120
cctggacaag gcttgagtg gatgggaggg atcatcccta tctttggtac agcaaactac     180
gcacagaagt tccagggcag agtcacgatt accgcggacg aatccacgag cacagcctac     240
atggagctga gcagcctgag atctgaggac acggccgtgt attactgtgc gaagtcccca     300
```

```
tttagtggga ccccggggga gtactggggc agaggaaccc tggtcaccgt ctcgagtggt    360
ggaggcggtt caggcggagg tggttctggc ggtggcggat cggaaattgt gttgacacag    420
tctccaggca ccctgtcttt atctccaggg gaaagagcca ccctctcctg cagggccagt    480
cagagtgtta gcagcaacta cttagcctgg tatcagcaga aacctggcca ggctcccaga    540
ctcctcatct atggtgcatc ccgcagggcc actggcatcc cagacaggtt cagtggcagt    600
gggtctggga cagacttcac tctcaccatc agcagagtgg agcctgaaga ctttgcagtg    660
tatcactgtc agcagtatgg tgcctcacct aagactttcg gccaaggga caagctggag    720 atcaaacgt                                                            729
```

<210> SEQ ID NO 2
<211> LENGTH: 243
<212> TYPE: PRT
<213> ORGANISM: Artificial sequence
<220> FEATURE:
<223> OTHER INFORMATION: amino acid sequence of single chain antibody P1B12E

<400> SEQUENCE: 2

```
Gln Val Gln Leu Val Glu Ser Gly Ala Glu Val Lys Lys Pro Gly Ala
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Ser Pro Phe Ser Gly Thr Pro Gly Glu Tyr Trp Gly Arg Gly
            100                 105                 110

Thr Leu Val Thr Val Ser Gly Gly Gly Gly Ser Gly Gly Gly Gly
        115                 120                 125

Ser Gly Gly Gly Gly Ser Glu Ile Val Leu Thr Gln Ser Pro Gly Thr
    130                 135                 140

Leu Ser Leu Ser Pro Gly Glu Arg Ala Thr Leu Ser Cys Arg Ala Ser
145                 150                 155                 160

Gln Ser Val Ser Ser Asn Tyr Leu Ala Trp Tyr Gln Gln Lys Pro Gly
                165                 170                 175

Gln Ala Pro Arg Leu Leu Ile Tyr Gly Ala Ser Arg Arg Ala Thr Gly
            180                 185                 190

Ile Pro Asp Arg Phe Ser Gly Ser Gly Thr Asp Phe Thr Leu
        195                 200                 205

Thr Ile Ser Arg Val Glu Pro Glu Asp Phe Ala Val Tyr His Cys Gln
    210                 215                 220

Gln Tyr Gly Ala Ser Pro Lys Thr Phe Gly Gln Gly Thr Lys Leu Glu
225                 230                 235                 240

Ile Lys Arg
```

<210> SEQ ID NO 3
<211> LENGTH: 741
<212> TYPE: DNA

<213> ORGANISM: Artificial sequence
<220> FEATURE:
<223> OTHER INFORMATION: Nucleotide sequence of single chain antibody P7D4

<400> SEQUENCE: 3

```
caggtgcagc tgcaggagtc cggggggaggc ttagttcagc ctggggaggtc cctgagactc    60
tcctgtgcag cctctggatt caccttcagt agctatgcta tgcactgggt ccgccaggct   120
ccaggcaagg ggctggagtg ggtctcagct attagtggta gtggtggtag cacatactac   180
gcagactccg tgaagggccg gttcaccatc tccagagaca attccaagaa cacgctgtat   240
ctgcaaatga acagcctgag agccgaggac acggccgtat attactgtgc gaaagatcga   300
cgagggagcc acgctgatgc ttttgatgtc tggggccaag aaccctggt caccgtctcg   360
agtggtggag gcggttcagg cggaggtggt tctggcggtg gcggatcgca gtctgccctg   420
actcagcctc cctccgcgtc cgggtctcct ggacagtcag tcaccatctc ctgcactgga   480
accagcagtg acgttggtgg ttataactat gtctcctggt accaacagta cccaggcaaa   540
gcccccaaac tcctcatcta tggtaacagc aatcggccct cagggggtccc tgaccgattc   600
tctggctcca agtctggcac ctcagcctcc ctggccatca ctgggctcca ggctgaggat   660
ggggctgatt attactgcca gtcctatgac agcagcctgc gtgtggtatt cggcggaggg   720
accaaggtca ccgtcctagg t                                              741
```

<210> SEQ ID NO 4
<211> LENGTH: 247
<212> TYPE: PRT
<213> ORGANISM: Artificial sequence
<220> FEATURE:
<223> OTHER INFORMATION: amino acid sequence of single chain antibody P7D4

<400> SEQUENCE: 4

```
Gln Val Gln Leu Gln Glu Ser Gly Gly Gly Leu Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Arg Gly Ser His Ala Asp Ala Phe Asp Val Trp Gly
            100                 105                 110

Gln Gly Thr Leu Val Thr Val Ser Ser Gly Gly Gly Ser Gly Gly
        115                 120                 125

Gly Gly Ser Gly Gly Gly Ser Gln Ser Ala Leu Thr Gln Pro Pro
    130                 135                 140

Ser Ala Ser Gly Ser Pro Gly Gln Ser Val Thr Ile Ser Cys Thr Gly
145                 150                 155                 160

Thr Ser Ser Asp Val Gly Gly Tyr Asn Tyr Val Ser Trp Tyr Gln Gln
                165                 170                 175

Tyr Pro Gly Lys Ala Pro Lys Leu Leu Ile Tyr Gly Asn Ser Asn Arg
            180                 185                 190
```

```
Pro Ser Gly Val Pro Asp Arg Phe Ser Gly Ser Lys Ser Gly Thr Ser
        195                 200                 205
Ala Ser Leu Ala Ile Thr Gly Leu Gln Ala Glu Asp Gly Ala Asp Tyr
        210                 215                 220
Tyr Cys Gln Ser Tyr Asp Ser Ser Leu Arg Val Val Phe Gly Gly Gly
225                 230                 235                 240
Thr Lys Val Thr Val Leu Gly
                245

<210> SEQ ID NO 5
<211> LENGTH: 28
<212> TYPE: DNA
<213> ORGANISM: Artificial sequence
<220> FEATURE:
<223> OTHER INFORMATION: Primer

<400> SEQUENCE: 5
acagtgctag cacaggtgca gctggtgg                                    28

<210> SEQ ID NO 6
<211> LENGTH: 27
<212> TYPE: DNA
<213> ORGANISM: Artificial sequence
<220> FEATURE:
<223> OTHER INFORMATION: Primer

<400> SEQUENCE: 6
ttgtcggatc cacgtttgat ctccagc                                     27

<210> SEQ ID NO 7
<211> LENGTH: 28
<212> TYPE: DNA
<213> ORGANISM: Artificial sequence
<220> FEATURE:
<223> OTHER INFORMATION: Primer

<400> SEQUENCE: 7
acagtgctag cacaggtgca gctgcagg                                    28

<210> SEQ ID NO 8
<211> LENGTH: 27
<212> TYPE: DNA
<213> ORGANISM: Artificial sequence
<220> FEATURE:
<223> OTHER INFORMATION: Primer

<400> SEQUENCE: 8
ttgtcggatc cacctaggac ggtgacc                                     27

<210> SEQ ID NO 9
<211> LENGTH: 30
<212> TYPE: DNA
<213> ORGANISM: Artificial sequence
<220> FEATURE:
<223> OTHER INFORMATION: Nucleotide sequence of P7D4 VH CDR1

<400> SEQUENCE: 9
ggattcacct tcagtagcta tgctatgcac                                  30

<210> SEQ ID NO 10
<211> LENGTH: 10
<212> TYPE: PRT
<213> ORGANISM: Artificial sequence
<220> FEATURE:
```

<223> OTHER INFORMATION: amino acid sequence of P7D4 VH CDR1

<400> SEQUENCE: 10

Gly Phe Thr Phe Ser Ser Tyr Ala Met His
1               5                   10

<210> SEQ ID NO 11
<211> LENGTH: 51
<212> TYPE: DNA
<213> ORGANISM: Artificial sequence
<220> FEATURE:
<223> OTHER INFORMATION: Nucleotide sequence of P7D4 VH CDR2

<400> SEQUENCE: 11
gctattagtg gtagtggtgg tagcacatac tacgcagact ccgtgaaggg c         51

<210> SEQ ID NO 12
<211> LENGTH: 17
<212> TYPE: PRT
<213> ORGANISM: Artificial sequence
<220> FEATURE:
<223> OTHER INFORMATION: amino acid sequence of P7D4 VH CDR2

<400> SEQUENCE: 12

Ala Ile Ser Gly Ser Gly Gly Ser Thr Tyr Tyr Ala Asp Ser Val Lys
1               5                   10                  15

Gly

<210> SEQ ID NO 13
<211> LENGTH: 36
<212> TYPE: DNA
<213> ORGANISM: Artificial sequence
<220> FEATURE:
<223> OTHER INFORMATION: Nucleotide sequence of P7D4 VH CDR3

<400> SEQUENCE: 13
gatcgacgag ggagccacgc tgatgctttt gatgtc                          36

<210> SEQ ID NO 14
<211> LENGTH: 12
<212> TYPE: PRT
<213> ORGANISM: Artificial sequence
<220> FEATURE:
<223> OTHER INFORMATION: amino acid sequence of P7D4 VH CDR3

<400> SEQUENCE: 14

Asp Arg Arg Gly Ser His Ala Asp Ala Phe Asp Val
1               5                   10

<210> SEQ ID NO 15
<211> LENGTH: 42
<212> TYPE: DNA
<213> ORGANISM: Artificial sequence
<220> FEATURE:
<223> OTHER INFORMATION: Nucleotide sequence of P7D4 VL CDR1

<400> SEQUENCE: 15
actggaacca gcagtgacgt tggtggttat aactatgtct cc                   42

<210> SEQ ID NO 16
<211> LENGTH: 14
<212> TYPE: PRT
<213> ORGANISM: Artificial sequence
<220> FEATURE:
<223> OTHER INFORMATION: amino acid sequence of P7D4 VL CDR1

<400> SEQUENCE: 16

Thr Gly Thr Ser Ser Asp Val Gly Gly Tyr Asn Tyr Val Ser
1               5                   10

<210> SEQ ID NO 17
<211> LENGTH: 21
<212> TYPE: DNA
<213> ORGANISM: Artificial sequence
<220> FEATURE:
<223> OTHER INFORMATION: Nucleotide sequence of P7D4 VL CDR2

<400> SEQUENCE: 17
ggtaacagca atcggccctc a                                                  21

<210> SEQ ID NO 18
<211> LENGTH: 7
<212> TYPE: PRT
<213> ORGANISM: Artificial sequence
<220> FEATURE:
<223> OTHER INFORMATION: amino acid sequence of P7D4 VL CDR2

<400> SEQUENCE: 18

Gly Asn Ser Asn Arg Pro Ser
1               5

<210> SEQ ID NO 19
<211> LENGTH: 30
<212> TYPE: DNA
<213> ORGANISM: Artificial sequence
<220> FEATURE:
<223> OTHER INFORMATION: Nucleotide sequence of P7D4 VL CDR3

<400> SEQUENCE: 19
cagtcctatg acagcagcct gcgtgtggta                                         30

<210> SEQ ID NO 20
<211> LENGTH: 10
<212> TYPE: PRT
<213> ORGANISM: Artificial sequence
<220> FEATURE:
<223> OTHER INFORMATION: amino acid sequence of P7D4 VL CDR3

<400> SEQUENCE: 20

Gln Ser Tyr Asp Ser Ser Leu Arg Val Val
1               5                   10

<210> SEQ ID NO 21
<211> LENGTH: 24
<212> TYPE: DNA
<213> ORGANISM: Artificial sequence
<220> FEATURE:
<223> OTHER INFORMATION: Primer

<400> SEQUENCE: 21
caacgtgaaa aaattattat tcgc                                               24

<210> SEQ ID NO 22
<211> LENGTH: 63
<212> TYPE: DNA
<213> ORGANISM: Artificial sequence
<220> FEATURE:
<221> NAME/KEY: misc_feature
<223> OTHER INFORMATION: Primer
<220> FEATURE:
<222> LOCATION: (33)..(34)
<223> OTHER INFORMATION: n is a, c, g, or t
<220> FEATURE:

```
<222> LOCATION: (45)..(46)
<223> OTHER INFORMATION: n is a, c, g, or t

<400> SEQUENCE: 22
ccagcccctt gcctggagcc tggcggaccc amnncatagc atamnnactg aaggtgaatc      60
cag                                                                   63

<210> SEQ ID NO 23
<211> LENGTH: 72
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t

<400> SEQUENCE: 23
gctccaggca aggggctgga gtgggtctca nnkattagtn nknnkgntnn knnkacatac      60
tacgcagact cc                                                         72

<210> SEQ ID NO 24
<211> LENGTH: 741
<212> TYPE: DNA
<213> ORGANISM: Artificial sequence
<220> FEATURE:
<223> OTHER INFORMATION: Nucleotide sequence of am4

<400> SEQUENCE: 24
caggtgcagc tgcaggagtc cggggggaggc ttagttcagc ctggggaggtc cctgagactc    60 tcctgtgcag cctctggatt caccttcagt acgtatgcta tgacgtgggt ccgccaggct    120
ccaggcaagg ggctggagtg gtctcatct attagtagta gtggtgaaag tacatactac    180
gcagactccg tgaagggccg gttcaccatc tccagagaca attccaagaa cacgctgtat    240
ctgcaaatga acagcctgag agccgaggac acggccgtat attactgtgc gaaagatcga    300
cgagggagcc acgctgatgc ttttgatgtc tggggccaag aaccctggt caccgtctcg    360 agtggtggag gcggttcagg cggaggtggt tctggcggtg gcggatcgca gtctgccctg    420
actcagcctc cctccgcgtc cgggtctcct ggacagtcag tcaccatctc ctgcactgga    480
accagcagtg acgttggtgg ttataactat gtctcctggt accaacagta cccaggcaaa    540 gccccccaaac tcctcatcta tggtaacagc aatcggccct caggggtccc tgaccgattc    600
tctggctcca agtctggcac ctcagcctcc ctggccatca ctgggctcca ggctgaggat    660
```

```
ggggctgatt attactgcca gtcctatgac agcagcctgc gtgtggtatt cggcggaggg    720
accaaggtca ccgtcctagg t                                              741
```

<210> SEQ ID NO 25
<211> LENGTH: 247
<212> TYPE: PRT
<213> ORGANISM: Artificial sequence
<220> FEATURE:
<223> OTHER INFORMATION: amino acid sequence of am4

<400> SEQUENCE: 25

```
Gln Val Gln Leu Gln Glu Ser Gly Gly Gly Leu Val Gln Pro Gly Arg
1               5                   10                  15

Ser Leu Arg Leu Ser Cys Ala Ala Ser Gly Phe Thr Phe Ser Thr Tyr
            20                  25                  30

Ala Met Thr Trp Val Arg Gln Ala Pro Gly Lys Gly Leu Glu Trp Val
        35                  40                  45

Ser Ser Ile Ser Ser Ser Gly Glu Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Arg Gly Ser His Ala Asp Ala Phe Asp Val Trp Gly
            100                 105                 110

Gln Gly Thr Leu Val Thr Val Ser Ser Gly Gly Gly Ser Gly Gly
        115                 120                 125

Gly Gly Ser Gly Gly Gly Ser Gln Ser Ala Leu Thr Gln Pro Pro
    130                 135                 140

Ser Ala Ser Gly Ser Pro Gly Gln Ser Val Thr Ile Ser Cys Thr Gly
145                 150                 155                 160

Thr Ser Ser Asp Val Gly Gly Tyr Asn Tyr Val Ser Trp Tyr Gln Gln
                165                 170                 175

Tyr Pro Gly Lys Ala Pro Lys Leu Leu Ile Tyr Gly Asn Ser Asn Arg
            180                 185                 190

Pro Ser Gly Val Pro Asp Arg Phe Ser Gly Ser Lys Ser Gly Thr Ser
        195                 200                 205

Ala Ser Leu Ala Ile Thr Gly Leu Gln Ala Glu Asp Gly Ala Asp Tyr
    210                 215                 220

Tyr Cys Gln Ser Tyr Asp Ser Ser Leu Arg Val Val Phe Gly Gly Gly
225                 230                 235                 240

Thr Lys Val Thr Val Leu Gly
                245
```

<210> SEQ ID NO 26
<211> LENGTH: 741
<212> TYPE: DNA
<213> ORGANISM: Artificial sequence
<220> FEATURE:
<223> OTHER INFORMATION: Nucleotide sequence of am14

<400> SEQUENCE: 26

```
caggtgcagc tgcaggagtc cggggggaggc ttagttcagc tggggaggtc cctgagactc    60
tcctgtgcag cctctggatt caccttcagt acttatgcta tggcttgggt ccgccaggct   120
ccaggcaagg ggctggagtg ggtctcagaa attagtagtt ctggtagtag gacatactac   180
gcagactccg tgaagggccg gttcaccatc tccagagaca attccaagaa cacgctgtat   240
```

```
ctgcaaatga acagcctgag agccgaggac acggccgtat attactgtgc gaaagatcga    300
cgagggagcc acgctgatgc ttttgatgtc tggggccaag aaccctggt  caccgtctcg    360 agtggtggag gcggttcagg cggaggtggt tctggcggtg gcggatcgca gtctgccctg    420
actcagcctc cctccgcgtc cgggtctcct ggacagtcag tcaccatctc ctgcactgga    480
accagcagtg acgttggtgg ttataactat gtctcctggt accaacagta cccaggcaaa    540 gccccaaac tcctcatcta tggtaacagc aatcggccct cagggtccc  tgaccgattc    600 tctggctcca agtctggcac ctcagcctcc ctggccatca ctgggctcca ggctgaggat    660
ggggctgatt attactgcca gtcctatgac agcagcctgc gtgtggtatt cggcggaggg    720
accaaggtca ccgtcctagg t                                              741
```

<210> SEQ ID NO 27
<211> LENGTH: 247
<212> TYPE: PRT
<213> ORGANISM: Artificial sequence
<220> FEATURE:
<223> OTHER INFORMATION: amino acid sequence of am14

<400> SEQUENCE: 27

```
Gln Val Gln Leu Gln Glu Ser Gly Gly Gly Leu Val Gln Pro Gly Arg
1               5                   10                  15

Ser Leu Arg Leu Ser Cys Ala Ala Ser Gly Phe Thr Phe Ser Thr Tyr
            20                  25                  30

Ala Met Ala Trp Val Arg Gln Ala Pro Gly Lys Gly Leu Glu Trp Val
        35                  40                  45

Ser Glu Ile Ser Ser Ser Gly Ser Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Arg Gly Ser His Ala Asp Ala Phe Asp Val Trp Gly
            100                 105                 110

Gln Gly Thr Leu Val Thr Val Ser Ser Gly Gly Gly Ser Gly Gly
        115                 120                 125

Gly Gly Ser Gly Gly Gly Ser Gln Ser Ala Leu Thr Gln Pro Pro
    130                 135                 140

Ser Ala Ser Gly Ser Pro Gly Gln Ser Val Thr Ile Ser Cys Thr Gly
145                 150                 155                 160

Thr Ser Ser Asp Val Gly Gly Tyr Asn Tyr Val Ser Trp Tyr Gln Gln
                165                 170                 175

Tyr Pro Gly Lys Ala Pro Lys Leu Leu Ile Tyr Gly Asn Ser Asn Arg
            180                 185                 190

Pro Ser Gly Val Pro Asp Arg Phe Ser Gly Ser Lys Ser Gly Thr Ser
        195                 200                 205

Ala Ser Leu Ala Ile Thr Gly Leu Gln Ala Glu Asp Gly Ala Asp Tyr
    210                 215                 220

Tyr Cys Gln Ser Tyr Asp Ser Ser Leu Arg Val Val Phe Gly Gly Gly
225                 230                 235                 240

Thr Lys Val Thr Val Leu Gly
                245
```

<210> SEQ ID NO 28

<211> LENGTH: 741
<212> TYPE: DNA
<213> ORGANISM: Artificial sequence
<220> FEATURE:
<223> OTHER INFORMATION: Nucleotide sequence of am20

<400> SEQUENCE: 28

```
caggtgcagc tgcaggagtc cggggggaggc ttagttcagc ctgggaggtc cctgagactc      60
tcctgtgcag cctctggatt caccttcagt acgtatgcta tgaattgggt ccgccaggct     120
ccaggcaagg ggctggagtg ggtctcagcg attagtatgt ctggtgaatc tacatactac     180
gcagactccg tgaagggccg gttcaccatc tccagagaca attccaagaa cacgctgtat     240
ctgcaaatga acagcctgag agccgaggac acggccgtat attactgtgc gaaagatcga     300
cgagggagcc acgctgatgc ttttgatgtc tggggccaag gaaccctggt caccgtctcg     360
agtggtggag gcggttcagg cggaggtggt tctggcggtg cggatcgca gtctgccctg     420
actcagcctc cctccgcgtc cgggtctcct ggacagtcag tcaccatctc ctgcactgga     480
accagcagtg acgttggtgg ttataactat gtctcctggt accaacagta cccaggcaaa     540
gcccccaaac tcctcatcta tggtaacagc aatcggccct caggggtccc tgaccgattc     600
tctggctcca agtctggcac ctcagcctcc ctggccatca ctgggctcca ggctgaggat     660
ggggctgatt attactgcca gtcctatgac agcagcctgc gtgtggtatt cggcggaggg     720
accaaggtca ccgtcctagg t                                                741
```

<210> SEQ ID NO 29
<211> LENGTH: 247
<212> TYPE: PRT
<213> ORGANISM: Artificial sequence
<220> FEATURE:
<223> OTHER INFORMATION: amino acid sequence of am20

<400> SEQUENCE: 29

```
Gln Val Gln Leu Gln Glu Ser Gly Gly Gly Leu Val Gln Pro Gly Arg
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Ala Ile Ser Met Ser Gly Glu Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Arg Gly Ser His Ala Asp Ala Phe Asp Val Trp Gly
            100                 105                 110

Gln Gly Thr Leu Val Thr Val Ser Ser Gly Gly Gly Ser Gly Gly
        115                 120                 125

Gly Gly Ser Gly Gly Gly Ser Gln Ser Ala Leu Thr Gln Pro Pro
    130                 135                 140

Ser Ala Ser Gly Ser Pro Gly Gln Ser Val Thr Ile Ser Cys Thr Gly
145                 150                 155                 160

Thr Ser Ser Asp Val Gly Gly Tyr Asn Tyr Val Ser Trp Tyr Gln Gln
                165                 170                 175

Tyr Pro Gly Lys Ala Pro Lys Leu Leu Ile Tyr Gly Asn Ser Asn Arg
            180                 185                 190
```

Pro Ser Gly Val Pro Asp Arg Phe Ser Gly Ser Lys Ser Gly Thr Ser
        195                 200                 205

Ala Ser Leu Ala Ile Thr Gly Leu Gln Ala Glu Asp Gly Ala Asp Tyr
        210                 215                 220

Tyr Cys Gln Ser Tyr Asp Ser Ser Leu Arg Val Val Phe Gly Gly Gly
225                 230                 235                 240

Thr Lys Val Thr Val Leu Gly
                245

<210> SEQ ID NO 30
<211> LENGTH: 741
<212> TYPE: DNA
<213> ORGANISM: Artificial sequence
<220> FEATURE:
<223> OTHER INFORMATION: Nucleotide sequence of am35

<400> SEQUENCE: 30
caggtgcagc tgcaggagtc cggggggaggc ttagttcagc ctgggaggtc cctgagactc      60
tcctgtgcag cctctggatt caccttcagt agctatgcta tgcactgggt ccgccaggct     120
ccaggcaagg ggctggagtg gtctcagct attagtagta gtggtggtag cacatactac      180
gcagactccg tgaagggccg gttcaccatc tccagagaca attccaagaa cacgctgtat     240
ctgcaaatga acagcctgag agccgaggac acggccgtat attactgtgc gaaagatcga     300
cgagggagcc acgctgatgc tttgatgtc tggggccaag aaccctggt caccgtctcg      360 agtggtggag gcggttcagg cggaggtggt tctggcggtg gcggatcgca gtctgccctg     420
actcagcctc cctccgcgtc cgggtctcct ggacagtcag tcaccatctc ctgcactgga     480
accagcagtg acgttggtca taagtttcct gtctcctggt accaacagta cccaggcaaa     540
gcccccaaac tcctcatcta taagaatctt ttgcggccct caggggtccc tgaccgattc     600
tctggctcca agtctggcac ctcagcctcc ctggccatca ctgggctcca ggctgaggat     660
ggggctgatt attactgcca gtcctatgac agcagcctgc gtgtggtatt cggcggaggg     720
accaaggtca ccgtcctagg t                                               741

<210> SEQ ID NO 31
<211> LENGTH: 247
<212> TYPE: PRT
<213> ORGANISM: Artificial sequence
<220> FEATURE:
<223> OTHER INFORMATION: amino acid sequence of am35

<400> SEQUENCE: 31

Gln Val Gln Leu Gln Glu Ser Gly Gly Gly Leu Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Ala Ile Ser Ser Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Arg Gly Ser His Ala Asp Ala Phe Asp Val Trp Gly
            100                 105                 110

Gln Gly Thr Leu Val Thr Val Ser Ser Gly Gly Gly Ser Gly Gly
        115                 120                 125

Gly Gly Ser Gly Gly Gly Ser Gln Ser Ala Leu Thr Gln Pro Pro
        130                 135                 140

Ser Ala Ser Gly Ser Pro Gly Gln Ser Val Thr Ile Ser Cys Thr Gly
145                 150                 155                 160

Thr Ser Ser Asp Val Gly His Lys Phe Pro Val Ser Trp Tyr Gln Gln
                165                 170                 175

Tyr Pro Gly Lys Ala Pro Lys Leu Leu Ile Tyr Lys Asn Leu Leu Arg
                180                 185                 190

Pro Ser Gly Val Pro Asp Arg Phe Ser Gly Ser Lys Ser Gly Thr Ser
                195                 200                 205

Ala Ser Leu Ala Ile Thr Gly Leu Gln Ala Glu Asp Gly Ala Asp Tyr
210                 215                 220

Tyr Cys Gln Ser Tyr Asp Ser Ser Leu Arg Val Val Phe Gly Gly
225                 230                 235                 240

Thr Lys Val Thr Val Leu Gly
                245

<210> SEQ ID NO 32
<211> LENGTH: 741
<212> TYPE: DNA
<213> ORGANISM: Artificial sequence
<220> FEATURE:
<223> OTHER INFORMATION: Nucleotide sequence of am42

<400> SEQUENCE: 32
caggtgcagc tgcaggagtc cggggaggc ttagttcagc tgggaggtc cctgagactc      60
tcctgtgcag cctctggatt caccttcagt agctatgcta tgcactgggt ccgccaggct     120
ccaggcaagg ggctggagtg gtctcagct attagtagta gtggtggtag cacatactac     180
gcagactccg tgaagggccg gttcaccatc tccagagaca attccaagaa cacgctgtat     240
ctgcaaatga acagcctgag agccgaggac acggccgtat attactgtgc gaaagatcga     300
cgagggagcc acgctgatgc ttttgatgtc tggggccaag aaccctggt caccgtctcg     360
agtggtggag gcggttcagg cggaggtggt tctggcggtg gcggatcgca gtctgccctg     420
actcagcctc cctccgcgtc cgggtctcct ggacagtcag tcaccatctc ctgcactgga     480
accagcagtg acgttggtct tatgcataat gtctcctggt accaacagta cccaggcaaa     540
gcccccaaac tcctcatcta taagtcttcg tctcggccct caggggtccc tgaccgattc     600
tctggctcca agtctggcac ctcagcctcc ctggccatca ctgggctcca ggctgaggat     660
ggggctgatt attactgcca gtcctatgac agcagcctgc gtgtggtatt cggcggaggg     720
accaaggtca ccgtcctagg t                                               741

<210> SEQ ID NO 33
<211> LENGTH: 247
<212> TYPE: PRT
<213> ORGANISM: Artificial sequence
<220> FEATURE:
<223> OTHER INFORMATION: amino acid sequence of am42

<400> SEQUENCE: 33

Gln Val Gln Leu Gln Glu Ser Gly Gly Gly Leu Val Gln Pro Gly Arg
1               5                   10                  15

Ser Leu Arg Leu Ser Cys Ala Ala Ser Gly Phe Thr Phe Ser Ser Tyr
            20                  25                  30

```
Ala Met His Trp Val Arg Gln Ala Pro Gly Lys Gly Leu Glu Trp Val
        35                  40                  45
Ser Ala Ile Ser Ser Gly Gly Ser Thr Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Lys Asp Arg Arg Gly Ser His Ala Asp Ala Phe Asp Val Trp Gly
                100                 105                 110
Gln Gly Thr Leu Val Thr Val Ser Ser Gly Gly Gly Ser Gly Gly
            115                 120                 125
Gly Gly Ser Gly Gly Gly Ser Gln Ser Ala Leu Thr Gln Pro Pro
        130                 135                 140
Ser Ala Ser Gly Ser Pro Gly Gln Ser Val Thr Ile Ser Cys Thr Gly
145                 150                 155                 160
Thr Ser Ser Asp Val Gly Leu Met His Asn Val Ser Trp Tyr Gln Gln
                165                 170                 175
Tyr Pro Gly Lys Ala Pro Lys Leu Leu Ile Tyr Lys Ser Ser Arg
            180                 185                 190
Pro Ser Gly Val Pro Asp Arg Phe Ser Gly Ser Lys Ser Gly Thr Ser
        195                 200                 205
Ala Ser Leu Ala Ile Thr Gly Leu Gln Ala Glu Asp Gly Ala Asp Tyr
210                 215                 220
Tyr Cys Gln Ser Tyr Asp Ser Ser Leu Arg Val Val Phe Gly Gly Gly
225                 230                 235                 240
Thr Lys Val Thr Val Leu Gly
            245

<210> SEQ ID NO 34
<211> LENGTH: 741
<212> TYPE: DNA
<213> ORGANISM: Artificial sequence
<220> FEATURE:
<223> OTHER INFORMATION: Nucleotide sequence of T2-23

<400> SEQUENCE: 34
caggtgcagc tgcaggagtc cggggggaggc ttagttcagc ctgggaggtc cctgagactc      60
tcctgtgcag cctctggatt caccttcagt agctatgcta tgcactgggt ccgccaggct     120
ccaggcaagg ggctggagtg ggtctcagct attagtagta gtggtcgtag cacatactac     180
gcagactccg tggagggccg gttcaccatc tccagagaca attccaagaa cacgctgtat     240
ctgcaaatga acagcctgag agccgaggac acggccgtat attactgtgc gaaagatcga     300
cgagggagcc acgctgatgc tttaaatgtc tggggccaag aaccctggt caccgtctcg     360 agtggtggag gcggttcagg cggaggtggt tctggcggtg gcggatcgca gtctgccctg     420
actcagcctc cctccgcgtc cgggtctcct ggacagtcag tcaccatctc ctgcactgga     480
accagcagtg acgttggtgg ttataactat gtctcctggt accaacagta cccaggcaaa     540
gcccccaaac tcctcatcta tgtaacagc atcggccct caggggtccc tgaccgattc     600
tctggctcca agtctggcac ctcagcctcc ctggccatca ctgggctcca ggctgaggat     660
ggggctgatt attactgcca gtcctatgac agcagcctgc gtgtggtatt cggcggaggg     720
accaaggtca ccgtcctagg t                                                741
```

<210> SEQ ID NO 35
<211> LENGTH: 247
<212> TYPE: PRT
<213> ORGANISM: Artificial sequence
<220> FEATURE:
<223> OTHER INFORMATION: amino acid sequence of T2-23

<400> SEQUENCE: 35

```
Gln Val Gln Leu Gln Glu Ser Gly Gly Gly Leu Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Ala Ile Ser Ser Ser Gly Arg Ser Thr Tyr Tyr Ala Asp Ser Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Arg Gly Ser His Ala Asp Ala Leu Asn Val Trp Gly
            100                 105                 110

Gln Gly Thr Leu Val Thr Val Ser Ser Gly Gly Gly Ser Gly Gly
        115                 120                 125

Gly Gly Ser Gly Gly Gly Gly Ser Gln Ser Ala Leu Thr Gln Pro Pro
    130                 135                 140

Ser Ala Ser Gly Ser Pro Gly Gln Ser Val Thr Ile Ser Cys Thr Gly
145                 150                 155                 160

Thr Ser Ser Asp Val Gly Gly Tyr Asn Tyr Val Ser Trp Tyr Gln Gln
                165                 170                 175

Tyr Pro Gly Lys Ala Pro Lys Leu Leu Ile Tyr Gly Asn Ser Asn Arg
            180                 185                 190

Pro Ser Gly Val Pro Asp Arg Phe Ser Gly Ser Lys Ser Gly Thr Ser
        195                 200                 205

Ala Ser Leu Ala Ile Thr Gly Leu Gln Ala Glu Asp Gly Ala Asp Tyr
    210                 215                 220

Tyr Cys Gln Ser Tyr Asp Ser Ser Leu Arg Val Val Phe Gly Gly Gly
225                 230                 235                 240

Thr Lys Val Thr Val Leu Gly
                245
```

<210> SEQ ID NO 36
<211> LENGTH: 36
<212> TYPE: DNA
<213> ORGANISM: Artificial sequence
<220> FEATURE:
<223> OTHER INFORMATION: Primer

<400> SEQUENCE: 36
ctccacgccg ccaggccgca ggtgcagctg caggag          36

<210> SEQ ID NO 37
<211> LENGTH: 38
<212> TYPE: DNA
<213> ORGANISM: Artificial sequence
<220> FEATURE:
<223> OTHER INFORMATION: Primer

<400> SEQUENCE: 37
cggcgctggc gtcgtggtac ctaggacggt gaccttgg                                    38

<210> SEQ ID NO 38
<211> LENGTH: 22
<212> TYPE: DNA
<213> ORGANISM: Artificial sequence
<220> FEATURE:
<223> OTHER INFORMATION: Primer

<400> SEQUENCE: 38 gcagggggaaa gaatagtaga ca                                                    22

<210> SEQ ID NO 39
<211> LENGTH: 18
<212> TYPE: DNA
<213> ORGANISM: Artificial sequence
<220> FEATURE:
<223> OTHER INFORMATION: Primer

<400> SEQUENCE: 39
cggcctggcg gcgtggag                                                          18

<210> SEQ ID NO 40
<211> LENGTH: 18
<212> TYPE: DNA
<213> ORGANISM: Artificial sequence
<220> FEATURE:
<223> OTHER INFORMATION: Primer

<400> SEQUENCE: 40
accacgacgc cagcgccg                                                          18

<210> SEQ ID NO 41
<211> LENGTH: 48
<212> TYPE: DNA
<213> ORGANISM: Artificial sequence
<220> FEATURE:
<223> OTHER INFORMATION: Primer

<400> SEQUENCE: 41
gaggtcgacc tacgcggggg cgtctgcgct cctgctgaac ttcactct                          48

<210> SEQ ID NO 42
<211> LENGTH: 18
<212> TYPE: DNA
<213> ORGANISM: Artificial sequence
<220> FEATURE:
<223> OTHER INFORMATION: Primer

<400> SEQUENCE: 42
accacgacgc cagcgccg                                                          18

<210> SEQ ID NO 43
<211> LENGTH: 44
<212> TYPE: DNA
<213> ORGANISM: Artificial sequence
<220> FEATURE:
<223> OTHER INFORMATION: Primer

<400> SEQUENCE: 43
aatccagagg ttgattgtcg acctagcgag ggggcagggc ctgc                              44

<210> SEQ ID NO 44
<211> LENGTH: 1442
<212> TYPE: DNA

<213> ORGANISM: Artificial sequence
<220> FEATURE:
<223> OTHER INFORMATION: Nucleotide sequence of P7D4 scFv-Z

<400> SEQUENCE: 44

| | | | | | |
|---|---|---|---|---|---|
| gcaggggaaa | gaatagtaga | cataatagca | acagacatac | aaactaaaga | attacaaaaa | 60 |
| caaattacaa | aaattcaaaa | ttttatcgat | ggctccggtg | cccgtcagtg | gcagagcgc | 120 |
| acatcgccca | cagtccccga | gaagttgggg | gaggggtcg | gcaattgaac | cggtgcctag | 180 |
| agaaggtggc | gcggggtaaa | ctgggaaagt | gatgtcgtgt | actggctccg | ccttttttccc | 240 |
| gagggtgggg | gagaaccgta | tataagtgca | gtagtcgccg | tgaacgttct | ttttcgcaac | 300 |
| gggtttgccg | ccagaacaca | ggtgtcgtga | cgcggatcca | ggcctaagct | tacgcgtcct | 360 |
| agcgctaccg | gtcgccacca | tggccttacc | agtgaccgcc | ttgctcctgc | cgctggcctt | 420 |
| gctgctccac | gccgccaggc | cgcaggtgca | gctgcaggag | tccggggggag | cttagttca | 480 |
| gcctgggagg | tccctgagac | tctcctgtgc | agcctctgga | ttcaccttca | gtagctatgc | 540 |
| tatgcactgg | gtccgccagg | ctccaggcaa | ggggctggag | tgggtctcag | ctattagtgg | 600 |
| tagtggtggt | agcacatact | acgcagactc | cgtgaagggc | cggttcacca | tctccagaga | 660 |
| caattccaag | aacacgctgt | atctgcaaat | gaacagcctg | agagccgagg | acacggccgt | 720 |
| atattactgt | gcgaaagatc | gacgagggag | ccacgctgat | gcttttgatg | tctggggcca | 780 |
| aggaaccctg | gtcaccgtct | cgagtggtgg | aggcggttca | ggcggaggtg | gttctggcgg | 840 |
| tggcggatcg | cagtctgccc | tgactcagcc | tccctccgcg | tccgggtctc | ctggacagtc | 900 |
| agtcaccatc | tcctgcactg | gaaccagcag | tgacgttggt | ggttataact | atgtctcctg | 960 |
| gtaccaacag | tacccaggca | agccccccaa | actcctcatc | tatggtaaca | gcaatcggcc | 1020 |
| ctcaggggtc | cctgaccgat | tctctggctc | caagtctggc | acctcagcct | ccctggccat | 1080 |
| cactgggctc | caggctgagg | atggggctga | ttattactgc | cagtcctatg | acagcagcct | 1140 |
| gcgtgtggta | ttcggcggag | ggaccaaggt | caccgtccta | ggtaccacga | cgccagcgcc | 1200 |
| gcgaccacca | acaccggcgc | ccaccatcgc | gtcgcagccc | ctgtccctgc | gcccagaggc | 1260 |
| gtgccggcca | gcggcggggg | gcgcagtgca | cacgaggggg | ctggacttcg | cctgtgatat | 1320 |
| ctacatctgg | gcgcccttgg | ccgggacttg | tggggtcctt | ctcctgtcac | tggttatcac | 1380 |
| cagagtgaag | ttcagcagga | gcgcagacgc | ccccgcgtag | gtcgacaatc | aacctctgga | 1440 |
| tt | | | | | | 1442 |

<210> SEQ ID NO 45
<211> LENGTH: 1745
<212> TYPE: DNA
<213> ORGANISM: Artificial sequence
<220> FEATURE:
<223> OTHER INFORMATION: Nucleotide sequence of P7D4 scFv-Z

<400> SEQUENCE: 45

| | | | | | |
|---|---|---|---|---|---|
| gcaggggaaa | gaatagtaga | cataatagca | acagacatac | aaactaaaga | attacaaaaa | 60 |
| caaattacaa | aaattcaaaa | ttttatcgat | ggctccggtg | cccgtcagtg | gcagagcgc | 120 |
| acatcgccca | cagtccccga | gaagttgggg | gaggggtcg | gcaattgaac | cggtgcctag | 180 |
| agaaggtggc | gcggggtaaa | ctgggaaagt | gatgtcgtgt | actggctccg | ccttttttccc | 240 |
| gagggtgggg | gagaaccgta | tataagtgca | gtagtcgccg | tgaacgttct | ttttcgcaac | 300 |
| gggtttgccg | ccagaacaca | ggtgtcgtga | cgcggatcca | ggcctaagct | tacgcgtcct | 360 |
| agcgctaccg | gtcgccacca | tggccttacc | agtgaccgcc | ttgctcctgc | cgctggcctt | 420 |

```
gctgctccac gccgccaggc cgcaggtgca gctgcaggag tccggggggag gcttagttca    480 gcctgggagg tccctgagac tctcctgtgc agcctctgga ttcaccttca gtagctatgc    540
tatgcactgg gtccgccagg ctccaggcaa ggggctggag tgggtctcag ctattagtgg    600
tagtggtggt agcacatact acgcagactc cgtgaagggc cggttcacca tctccagaga    660
caattccaag aacacgctgt atctgcaaat gaacagcctg agagccgagg acacggccgt    720
atattactgt gcgaaagatc gacgagggag ccacgctgat gcttttgatg tctgggccca    780
aggaaccctg gtcaccgtct cgagtggtgg aggcggttca ggcggaggtg gttctggcgg    840
tggcggatcg cagtctgccc tgactcagcc tccctccgcg tccgggtctc ctggacagtc    900
agtcaccatc tcctgcactg gaaccagcag tgacgttggt ggttataact atgtctcctg    960
gtaccaacag tacccaggca aagcccccaa actcctcatc tatggtaaca gcaatcggcc   1020
ctcaggggtc cctgaccgat tctctggctc caagtctggc acctcagcct ccctggccat   1080
cactgggctc caggctgagg atggggctga ttattactgc cagtcctatg acagcagcct   1140
gcgtgtggta ttcggcggag ggaccaaggt caccgtccta ggtaccacga cgccagcgcc   1200
gcgaccacca caccggcgc ccaccatcgc gtcgcagccc ctgtccctgc gcccagaggc   1260
gtgccggcca gcggcgggg gcgcagtgca cacgagggg ctggacttcg cctgtgatat   1320
ctacatctgg gcgcccttgg ccgggacttg tggggtcctt ctcctgtcac tggttatcac   1380
cagagtgaag ttcagcagga gcgcagacgc ccccgcgtac cagcagggcc agaaccagct   1440
ctataacgag ctcaatctag gacgaagaga ggagtacgat gttttggaca gagacgtgg   1500 ccgggaccct gagatgggg gaaagccgca gagaaggaag aaccctcagg aaggcctgta   1560
caatgaactg cagaaagata agatggcgga ggcctacagt gagattggga tgaaaggcga   1620
gcgccggagg ggcaaggggc acgatggcct ttaccagggt ctcagtacag ccaccaagga   1680
cacctacgac gcccttcaca tgcaggcccct gccccctcgc taggtcgaca atcaacctct   1740
ggatt                                                               1745

<210> SEQ ID NO 46
<211> LENGTH: 1877
<212> TYPE: DNA
<213> ORGANISM: Artificial sequence
<220> FEATURE:
<223> OTHER INFORMATION: Nucleotide sequence of P7D4 scFv-BBZ

<400> SEQUENCE: 46 gcagggaaa gaatagtaga cataatagca acagacatac aaactaaaga attacaaaaa     60
caaattacaa aaattcaaaa ttttatcgat ggctccggtg cccgtcagtg ggcagagcgc    120
acatcgccca cagtccccga gaagttgggg ggaggggtcg gcaattgaac cggtgcctag    180
agaaggtggc gcggggtaaa ctgggaaagt gatgtcgtgt actggctccg cctttttccc    240
gagggtgggg gagaaccgta tataagtgca gtagtcgccg tgaacgttct ttttcgcaac    300
gggtttgccg ccagaacaca ggtgtcgtga cgcggatcca ggcctaagct tacgcgtcct    360
agcgctaccg gtcgccacca tggcttacc agtgaccgcc ttgctcctgc cgctggcctt    420
gctgctccac gccgccaggc cgcaggtgca gctgcaggag tccggggggag cttagttca    480 gcctgggagg tccctgagac tctcctgtgc agcctctgga ttcaccttca gtagctatgc    540
tatgcactgg gtccgccagg ctccaggcaa ggggctggag tgggtctcag ctattagtgg    600
tagtggtggt agcacatact acgcagactc cgtgaagggc cggttcacca tctccagaga    660
```

```
caattccaag aacacgctgt atctgcaaat gaacagcctg agagccgagg acacggccgt      720
atattactgt gcgaaagatc gacgagggag ccacgctgat gcttttgatg tctggggcca      780
aggaaccctg gtcaccgtct cgagtggtgg aggcggttca ggcggaggtg gttctggcgg      840
tggcggatcg cagtctgccc tgactcagcc tccctccgcg tccgggtctc ctggacagtc      900
agtcaccatc tcctgcactg gaaccagcag tgacgttggt ggttataact atgtctcctg      960
gtaccaacag tacccaggca aagcccccaa actcctcatc tatggtaaca gcaatcggcc     1020
ctcaggggtc cctgaccgat tctctggctc caagtctggc acctcagcct ccctggccat     1080
cactgggctc caggctgagg atggggctga ttattactgc cagtcctatg acagcagcct     1140
gcgtgtggta ttcggcggag ggaccaaggt caccgtccta ggtaccacga cgccagcgcc     1200
gcgaccacca caccggcgc ccaccatcgc gtcgcagccc ctgtccctgc gcccagaggc     1260
gtgccggcca gcggcggggg gcgcagtgca cacgagggg ctggacttcg cctgtgatat     1320
ctacatctgg gcgcccttgg ccgggacttg tggggtcctt ctcctgtcac tggttatcac     1380
cctttactgc aaacggggca gaaagaaact cctgtatata ttcaaacaac catttatgag     1440
accagtacaa actactcaag aggaagatgg ctgtagctgc cgatttccag aagaagaaga     1500
aggaggatgt gaactgagag tgaagttcag caggagcgca gacgccccg cgtacaagca     1560 gggccagaac cagctctata cgagctcaa tctaggacga agagaggagt acgatgtttt     1620
ggacaagaga cgtggccggg accctgagat gggggaaag ccgagaagga agaaccctca     1680
ggaaggcctg tacaatgaac tgcagaaaga taagatggcg gaggcctaca gtgagattgg     1740
gatgaaaggc gagcgccgga ggggcaaggg gcacgatgcc ctttaccagg gtctcagtac     1800
agccaccaag gacacctacg acgcccttca catgcaggcc ctgcccctc gctaggtcga     1860 caatcaacct ctggatt                                                    1877

<210> SEQ ID NO 47
<211> LENGTH: 1886
<212> TYPE: DNA
<213> ORGANISM: Artificial sequence
<220> FEATURE:
<223> OTHER INFORMATION: Nucleotide sequence of P7D4 scFv-28Z

<400> SEQUENCE: 47
gcaggggaaa gaatagtaga cataatagca acagacatac aaactaaaga attacaaaaa       60
caaattacaa aaattcaaaa ttttatcgat ggctccggtg cccgtcagtg gcagagcgc      120 acatcgccca cagtccccga gaagttgggg ggaggggtcg gcaattgaac cggtgcctag      180
agaaggtggc gcggggtaaa ctgggaaagt gatgtcgtgt actggctccg ccttttttccc     240 gagggtgggg gagaaccgta tataagtgca gtagtcgccg tgaacgttct ttttcgcaac     300
gggtttgccg ccagaacaca ggtgtcgtga cgcggatcca ggcctaagct tacgcgtcct     360
agcgctaccg gtcgccacca tggccttacc agtgaccgcc ttgctcctgc cgctggcctt     420
gctgctccac gccgccaggc cgcaggtgca gctgcaggag tccggggag cttagttca     480 gcctgggagg tccctgagac tctcctgtgc agcctctgga ttcaccttca gtagctatgc     540
tatgcactgg gtccgccagg ctccaggcaa ggggctggag tgggtctcag ctattagtgg     600
tagtggtggt agcacatact acgcagactc cgtgaagggc cggttcacca tctccagaga     660
caattccaag aacacgctgt atctgcaaat gaacagcctg agagccgagg acacggccgt      720
atattactgt gcgaaagatc gacgagggag ccacgctgat gcttttgatg tctggggcca      780
aggaaccctg gtcaccgtct cgagtggtgg aggcggttca ggcggaggtg gttctggcgg      840
```

```
tggcggatcg cagtctgccc tgactcagcc tccctccgcg tccgggtctc ctggacagtc      900
agtcaccatc tcctgcactg gaaccagcag tgacgttggt ggttataact atgtctcctg      960
gtaccaacag tacccaggca aagcccccaa actcctcatc tatggtaaca gcaatcggcc     1020
ctcaggggtc cctgaccgat tctctggctc caagtctggc acctcagcct ccctggccat     1080
cactgggctc caggctgagg atggggctga ttattactgc cagtcctatg acagcagcct     1140
gcgtgtggta ttcggcggag ggaccaaggt caccgtccta ggtaccacga cgccagcgcc     1200
gcgaccacca caccggcgc caccatcgc gtcgcagccc ctgtccctgc gcccagaggc     1260
gtgccggcca gcggcggggg cgcagtgca cacgaggggg ctggacttcg cctgtgattt     1320
ttgggtgctg gtggtggttg gtggagtcct ggcttgctat agcttgctag taacagtggc     1380
ctttattatt ttctgggtga ggagtaagag gagcaggctc ctgcacagtg actacatgaa     1440
catgactccc cgccgcccg gccaacccg caagcattac cagccctatg ccccaccacg     1500
cgacttcgca gcctatcgct ccagagtgaa gttcagcagg agcgcagacg ccccgcgta     1560 ccagcagggc cagaaccagc tctataacga gctcaatcta ggacgaagag aggagtacga     1620
tgttttggac aagagacgtg gccgggaccc tgagatgggg ggaaagccgc agagaaggaa     1680
gaaccctcag gaaggcctgt acaatgaact gcagaaagat aagatggcgg aggcctacag     1740
tgagattggg atgaaaggcg agcgccggag gggcaagggg cacgatggcc tttaccaggg     1800
tctcagtaca gccaccaagg acacctacga cgcccttcac atgcaggccc tgccccctcg     1860
ctaggtcgac aatcaacctc tggatt                                          1886

<210> SEQ ID NO 48
<211> LENGTH: 2012
<212> TYPE: DNA
<213> ORGANISM: Artificial sequence
<220> FEATURE:
<223> OTHER INFORMATION: Nucleotide sequence of P7D4 scFv-28BBZ

<400> SEQUENCE: 48 gcagggaaa gaatagtaga cataatagca acagacatac aaactaaaga attacaaaaa       60
caaattacaa aaattcaaaa ttttatcgat ggctccggtg cccgtcagtg ggcagagcgc     120
acatcgccca cagtccccga gaagttgggg ggaggggtcg gcaattgaac cggtgcctag     180
agaaggtggc gcggggtaaa ctgggaaagt gatgtcgtgt actggctccg cctttttccc     240
gagggtgggg gagaaccgta tataagtgca gtagtcgccg tgaacgttct ttttcgcaac     300
gggtttgccc ccagaacaca ggtgtcgtga cgcggatcca ggcctaagct tacgcgtcct     360
agcgctaccg gtcgccacca tggccttacc agtgaccgcc ttgctcctgc cgctggcctt     420
gctgctccac gccgccaggc cgcaggtgca gctgcaggag tccggggag cttagttca      480 gcctgggagg tccctgagac tctcctgtgc agcctctgga ttcaccttca gtagctatgc     540
tatgcactgg gtccgccagg ctccaggcaa ggggctggag tgggtctcag ctattagtgg     600
tagtggtggt agcacatact acgcagactc cgtgaagggc cggttcacca tctccagaga     660
caattccaag aacacgctgt atctgcaaat gaacagcctg agagccgagg acacggccgt     720
atattactgt gcgaaagatc gacgaggag ccacgctgat gcttttgatg tctggggcca     780
aggaaccctg gtcaccgtct cgagtggtgg aggcggttca ggcggaggtg gttctggcgg     840
tggcggatcg cagtctgccc tgactcagcc tccctccgcg tccgggtctc ctggacagtc     900
agtcaccatc tcctgcactg gaaccagcag tgacgttggt ggttataact atgtctcctg     960
```

|  |  |  |
|---|---|---|
| gtaccaacag tacccaggca aagcccccaa actcctcatc tatggtaaca gcaatcggcc | 1020 |
| ctcaggggtc cctgaccgat tctctggctc caagtctggc acctcagcct ccctggccat | 1080 |
| cactgggctc caggctgagg atggggctga ttattactgc cagtcctatg acagcagcct | 1140 |
| gcgtgtggta ttcggcggag ggaccaaggt caccgtccta ggtaccacga cgccagcgcc | 1200 |
| gcgaccacca acaccggcgc ccaccatcgc gtcgcagccc ctgtccctgc gcccagaggc | 1260 |
| gtgccggcca gcggcggggg gcgcagtgca cacgaggggg ctggacttcg cctgtgattt | 1320 |
| ttgggtgctg gtggtggttg gtggagtcct ggcttgctat agcttgctag taacagtggc | 1380 |
| ctttattatt ttctgggtga ggagtaagag gagcaggctc ctgcacagtg actacatgaa | 1440 |
| catgactccc cgccgccccg ggccaacccg caagcattac cagccctatg ccccaccacg | 1500 |
| cgacttcgca gcctatcgct ccaaacgggg cagaaagaaa ctcctgtata tattcaaaca | 1560 |
| accatttatg agaccagtac aaactactca agaggaagat ggctgtagct gccgatttcc | 1620 |
| agaagaagaa gaaggaggat gtgaactgag agtgaagttc agcaggagcg cagacgcccc | 1680 |
| cgcgtaccag cagggccaga accagctcta taacgagctc aatctaggac gaagagagga | 1740 |
| gtacgatgtt ttggacaaga cgtggccg ggaccctgag atgggggga agccgcagag | 1800 |
| aaggaagaac cctcaggaag gcctgtacaa tgaactgcag aaagataaga tggcggaggc | 1860 |
| ctacagtgag attgggatga aaggcgagcg ccggagggc aaggggcacg atggcctta | 1920 |
| ccagggtctc agtacagcca ccaaggacac ctacgacgcc cttcacatgc aggccctgcc | 1980 |
| ccctcgctag gtcgacaatc aacctctgga tt | 2012 |

<210> SEQ ID NO 49
<211> LENGTH: 346
<212> TYPE: PRT
<213> ORGANISM: Artificial sequence
<220> FEATURE:
<223> OTHER INFORMATION: amino acid sequence of P7D4-Z

<400> SEQUENCE: 49

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Gly Gly Leu
            20                  25                  30

Val Gln Pro Gly Arg Ser Leu Arg Leu Ser Cys Ala Ala Ser Gly Phe
        35                  40                  45

Thr Phe Ser Ser Tyr Ala Met His Trp Val Arg Gln Ala Pro Gly Lys
    50                  55                  60

Gly Leu Glu Trp Val Ser Ala Ile Ser Gly Ser Gly Gly Ser Thr Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Lys Asp Arg Arg Gly Ser His Ala Asp Ala
        115                 120                 125

Phe Asp Val Trp Gly Gln Gly Thr Leu Val Thr Val Ser Ser Gly Gly
    130                 135                 140

Gly Gly Ser Gly Gly Gly Gly Ser Gly Gly Gly Gly Ser Gln Ser Ala
145                 150                 155                 160

Leu Thr Gln Pro Pro Ser Ala Ser Gly Ser Pro Gly Gln Ser Val Thr
                165                 170                 175

```
Ile Ser Cys Thr Gly Thr Ser Ser Asp Val Gly Gly Tyr Asn Tyr Val
            180                 185                 190

Ser Trp Tyr Gln Gln Tyr Pro Gly Lys Ala Pro Lys Leu Leu Ile Tyr
        195                 200                 205

Gly Asn Ser Asn Arg Pro Ser Gly Val Pro Asp Arg Phe Ser Gly Ser
        210                 215                 220

Lys Ser Gly Thr Ser Ala Ser Leu Ala Ile Thr Gly Leu Gln Ala Glu
225                 230                 235                 240

Asp Gly Ala Asp Tyr Tyr Cys Gln Ser Tyr Asp Ser Ser Leu Arg Val
                245                 250                 255

Val Phe Gly Gly Gly Thr Lys Val Thr Val Leu Gly Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
        290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Arg Val
                325                 330                 335

Lys Phe Ser Arg Ser Ala Asp Ala Pro Ala
            340                 345

<210> SEQ ID NO 50
<211> LENGTH: 447
<212> TYPE: PRT
<213> ORGANISM: Artificial sequence
<220> FEATURE:
<223> OTHER INFORMATION: amino acid sequence of P7D4-Z

<400> SEQUENCE: 50

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Gly Gly Leu
            20                  25                  30

Val Gln Pro Gly Arg Ser Leu Arg Leu Ser Cys Ala Ala Ser Gly Phe
        35                  40                  45

Thr Phe Ser Ser Tyr Ala Met His Trp Val Arg Gln Ala Pro Gly Lys
    50                  55                  60

Gly Leu Glu Trp Val Ser Ala Ile Ser Gly Ser Gly Gly Ser Thr Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Lys Asp Arg Arg Gly Ser His Ala Asp Ala
        115                 120                 125

Phe Asp Val Trp Gly Gln Gly Thr Leu Val Thr Val Ser Ser Gly Gly
    130                 135                 140

Gly Gly Ser Gly Gly Gly Gly Ser Gly Gly Gly Gly Ser Gln Ser Ala
145                 150                 155                 160

Leu Thr Gln Pro Pro Ser Ala Ser Gly Ser Pro Gly Gln Ser Val Thr
                165                 170                 175

Ile Ser Cys Thr Gly Thr Ser Ser Asp Val Gly Gly Tyr Asn Tyr Val
            180                 185                 190
```

```
Ser Trp Tyr Gln Gln Tyr Pro Gly Lys Ala Pro Lys Leu Leu Ile Tyr
            195                 200                 205

Gly Asn Ser Asn Arg Pro Ser Gly Val Pro Asp Arg Phe Ser Gly Ser
210                 215                 220

Lys Ser Gly Thr Ser Ala Ser Leu Ala Ile Thr Gly Leu Gln Ala Glu
225                 230                 235                 240

Asp Gly Ala Asp Tyr Tyr Cys Gln Ser Tyr Asp Ser Ser Leu Arg Val
                245                 250                 255

Val Phe Gly Gly Gly Thr Lys Val Thr Val Leu Gly Thr Thr Thr Pro
            260                 265                 270

Ala Pro Arg Pro Pro Thr Pro Ala Pro Thr Ile Ala Ser Gln Pro Leu
            275                 280                 285

Ser Leu Arg Pro Glu Ala Cys Arg Pro Ala Ala Gly Gly Ala Val His
        290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Arg Val
                325                 330                 335

Lys Phe Ser Arg Ser Ala Asp Ala Pro Ala Tyr Gln Gln Gly Gln Asn
            340                 345                 350

Gln Leu Tyr Asn Glu Leu Asn Leu Gly Arg Arg Glu Glu Tyr Asp Val
        355                 360                 365

Leu Asp Lys Arg Arg Gly Arg Asp Pro Glu Met Gly Gly Lys Pro Gln
370                 375                 380

Arg Arg Lys Asn Pro Gln Glu Gly Leu Tyr Asn Glu Leu Gln Lys Asp
385                 390                 395                 400

Lys Met Ala Glu Ala Tyr Ser Glu Ile Gly Met Lys Gly Glu Arg Arg
                405                 410                 415

Arg Gly Lys Gly His Asp Gly Leu Tyr Gln Gly Leu Ser Thr Ala Thr
            420                 425                 430

Lys Asp Thr Tyr Asp Ala Leu His Met Gln Ala Leu Pro Pro Arg
            435                 440                 445
```

<210> SEQ ID NO 51
<211> LENGTH: 491
<212> TYPE: PRT
<213> ORGANISM: Artificial sequence
<220> FEATURE:
<223> OTHER INFORMATION: amino acid sequence of P7D4-BBZ

<400> SEQUENCE: 51

```
Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Gly Gly Leu
            20                  25                  30

Val Gln Pro Gly Arg Ser Leu Arg Leu Ser Cys Ala Ala Ser Gly Phe
        35                  40                  45

Thr Phe Ser Ser Tyr Ala Met His Trp Val Arg Gln Ala Pro Gly Lys
    50                  55                  60

Gly Leu Glu Trp Val Ser Ala Ile Ser Gly Ser Gly Gly Ser Thr Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110
```

```
Ala Val Tyr Tyr Cys Ala Lys Asp Arg Arg Gly Ser His Ala Asp Ala
            115                 120                 125

Phe Asp Val Trp Gly Gln Gly Thr Leu Val Thr Val Ser Ser Gly Gly
130                 135                 140

Gly Gly Ser Gly Gly Gly Ser Gly Gly Gly Ser Gln Ser Ala
145                 150                 155                 160

Leu Thr Gln Pro Pro Ser Ala Ser Gly Ser Pro Gly Gln Ser Val Thr
            165                 170                 175

Ile Ser Cys Thr Gly Thr Ser Ser Asp Val Gly Gly Tyr Asn Tyr Val
            180                 185                 190

Ser Trp Tyr Gln Gln Tyr Pro Gly Lys Ala Pro Lys Leu Leu Ile Tyr
            195                 200                 205

Gly Asn Ser Asn Arg Pro Ser Gly Val Pro Asp Arg Phe Ser Gly Ser
            210                 215                 220

Lys Ser Gly Thr Ser Ala Ser Leu Ala Ile Thr Gly Leu Gln Ala Glu
225                 230                 235                 240

Asp Gly Ala Asp Tyr Tyr Cys Gln Ser Tyr Asp Ser Ser Leu Arg Val
            245                 250                 255

Val Phe Gly Gly Gly Thr Lys Val Thr Val Leu Gly Thr Thr Thr Pro
            260                 265                 270

Ala Pro Arg Pro Pro Thr Pro Ala Pro Thr Ile Ala Ser Gln Pro Leu
            275                 280                 285

Ser Leu Arg Pro Glu Ala Cys Arg Pro Ala Ala Gly Gly Ala Val His
            290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
            325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
            355                 360                 365

Phe Pro Glu Glu Glu Glu Gly Gly Cys Glu Leu Arg Val Lys Phe Ser
370                 375                 380

Arg Ser Ala Asp Ala Pro Ala Tyr Lys Gln Gly Gln Asn Gln Leu Tyr
385                 390                 395                 400

Asn Glu Leu Asn Leu Gly Arg Arg Glu Glu Tyr Asp Val Leu Asp Lys
            405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
            435                 440                 445

Ala Tyr Ser Glu Ile Gly Met Lys Gly Glu Arg Arg Arg Gly Lys Gly
            450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
            485                 490

<210> SEQ ID NO 52
<211> LENGTH: 494
<212> TYPE: PRT
<213> ORGANISM: Artificial sequence
<220> FEATURE:
<223> OTHER INFORMATION: amino acid sequence of P7D4-28Z
```

<400> SEQUENCE: 52

```
Met Ala Leu Pro Val Thr Ala Leu Leu Pro Leu Ala Leu Leu Leu
1               5                   10                  15

His Ala Ala Arg Pro Gln Val Gln Leu Gln Glu Ser Gly Gly Gly Leu
            20                  25                  30

Val Gln Pro Gly Arg Ser Leu Arg Leu Ser Cys Ala Ala Ser Gly Phe
        35                  40                  45

Thr Phe Ser Ser Tyr Ala Met His Trp Val Arg Gln Ala Pro Gly Lys
    50                  55                  60

Gly Leu Glu Trp Val Ser Ala Ile Ser Gly Ser Gly Gly Ser Thr Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Lys Asp Arg Arg Gly Ser His Ala Asp Ala
        115                 120                 125

Phe Asp Val Trp Gly Gln Gly Thr Leu Val Thr Val Ser Ser Gly Gly
    130                 135                 140

Gly Gly Ser Gly Gly Gly Ser Gly Gly Gly Ser Gln Ser Ala
145                 150                 155                 160

Leu Thr Gln Pro Pro Ser Ala Ser Gly Ser Pro Gly Gln Ser Val Thr
                165                 170                 175

Ile Ser Cys Thr Gly Thr Ser Ser Asp Val Gly Gly Tyr Asn Tyr Val
            180                 185                 190

Ser Trp Tyr Gln Gln Tyr Pro Gly Lys Ala Pro Lys Leu Leu Ile Tyr
        195                 200                 205

Gly Asn Ser Asn Arg Pro Ser Gly Val Pro Asp Arg Phe Ser Gly Ser
    210                 215                 220

Lys Ser Gly Thr Ser Ala Ser Leu Ala Ile Thr Gly Leu Gln Ala Glu
225                 230                 235                 240

Asp Gly Ala Asp Tyr Tyr Cys Gln Ser Tyr Asp Ser Ser Leu Arg Val
                245                 250                 255

Val Phe Gly Gly Gly Thr Lys Val Thr Val Leu Gly Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Phe Trp Val Leu Val Val Val
305                 310                 315                 320

Gly Gly Val Leu Ala Cys Tyr Ser Leu Leu Val Thr Val Ala Phe Ile
                325                 330                 335

Ile Phe Trp Val Arg Ser Lys Arg Ser Arg Leu Leu His Ser Asp Tyr
            340                 345                 350

Met Asn Met Thr Pro Arg Arg Pro Gly Pro Thr Arg Lys His Tyr Gln
        355                 360                 365

Pro Tyr Ala Pro Pro Arg Asp Phe Ala Ala Tyr Arg Ser Arg Val Lys
    370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
```

405                 410                 415
Asp Lys Arg Arg Gly Arg Asp Pro Glu Met Gly Gly Lys Pro Gln Arg
            420                 425                 430

Arg Lys Asn Pro Gln Glu Gly Leu Tyr Asn Glu Leu Gln Lys Asp Lys
            435                 440                 445

Met Ala Glu Ala Tyr Ser Glu Ile Gly Met Lys Gly Glu Arg Arg Arg
        450                 455                 460

Gly Lys Gly His Asp Gly Leu Tyr Gln Gly Leu Ser Thr Ala Thr Lys
465                 470                 475                 480

Asp Thr Tyr Asp Ala Leu His Met Gln Ala Leu Pro Pro Arg
                485                 490

<210> SEQ ID NO 53
<211> LENGTH: 536
<212> TYPE: PRT
<213> ORGANISM: Artificial sequence
<220> FEATURE:
<223> OTHER INFORMATION: amino acid sequence of P7D4-28BBZ

<400> SEQUENCE: 53

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Gly Gly Leu
            20                  25                  30

Val Gln Pro Gly Arg Ser Leu Arg Leu Ser Cys Ala Ala Ser Gly Phe
        35                  40                  45

Thr Phe Ser Ser Tyr Ala Met His Trp Val Arg Gln Ala Pro Gly Lys
    50                  55                  60

Gly Leu Glu Trp Val Ser Ala Ile Ser Gly Ser Gly Gly Ser Thr Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Lys Asp Arg Arg Gly Ser His Ala Asp Ala
        115                 120                 125

Phe Asp Val Trp Gly Gln Gly Thr Leu Val Thr Val Ser Ser Gly Gly
    130                 135                 140

Gly Gly Ser Gly Gly Gly Gly Ser Gly Gly Gly Gly Ser Gln Ser Ala
145                 150                 155                 160

Leu Thr Gln Pro Pro Ser Ala Ser Gly Ser Pro Gly Gln Ser Val Thr
                165                 170                 175

Ile Ser Cys Thr Gly Thr Ser Ser Asp Val Gly Gly Tyr Asn Tyr Val
            180                 185                 190

Ser Trp Tyr Gln Gln Tyr Pro Gly Lys Ala Pro Lys Leu Leu Ile Tyr
        195                 200                 205

Gly Asn Ser Asn Arg Pro Ser Gly Val Pro Asp Arg Phe Ser Gly Ser
    210                 215                 220

Lys Ser Gly Thr Ser Ala Ser Leu Ala Ile Thr Gly Leu Gln Ala Glu
225                 230                 235                 240

Asp Gly Ala Asp Tyr Tyr Cys Gln Ser Tyr Asp Ser Ser Leu Arg Val
                245                 250                 255

Val Phe Gly Gly Gly Thr Lys Val Thr Val Leu Gly Thr Thr Thr Pro
            260                 265                 270

Ala Pro Arg Pro Pro Thr Pro Ala Pro Thr Ile Ala Ser Gln Pro Leu

```
                  275                 280                 285
        Ser Leu Arg Pro Glu Ala Cys Arg Pro Ala Gly Gly Ala Val His
            290                 295                 300

Thr Arg Gly Leu Asp Phe Ala Cys Asp Phe Trp Val Leu Val Val
        305                 310                 315                 320

Gly Gly Val Leu Ala Cys Tyr Ser Leu Leu Val Thr Val Ala Phe Ile
                            325                 330                 335

Ile Phe Trp Val Arg Ser Lys Arg Ser Arg Leu Leu His Ser Asp Tyr
                        340                 345                 350

Met Asn Met Thr Pro Arg Arg Pro Gly Pro Thr Arg Lys His Tyr Gln
                    355                 360                 365

Pro Tyr Ala Pro Pro Arg Asp Phe Ala Ala Tyr Arg Ser Lys Arg Gly
                370                 375                 380

Arg Lys Lys Leu Leu Tyr Ile Phe Lys Gln Pro Phe Met Arg Pro Val
        385                 390                 395                 400

Gln Thr Thr Gln Glu Glu Asp Gly Cys Ser Cys Arg Phe Pro Glu Glu
                            405                 410                 415

Glu Glu Gly Gly Cys Glu Leu Arg Val Lys Phe Ser Arg Ser Ala Asp
                            420                 425                 430

Ala Pro Ala Tyr Gln Gln Gly Gln Asn Gln Leu Tyr Asn Glu Leu Asn
                        435                 440                 445

Leu Gly Arg Arg Glu Glu Tyr Asp Val Leu Asp Lys Arg Arg Gly Arg
            450                 455                 460

Asp Pro Glu Met Gly Gly Lys Pro Gln Arg Arg Lys Asn Pro Gln Glu
        465                 470                 475                 480

Gly Leu Tyr Asn Glu Leu Gln Lys Asp Lys Met Ala Glu Ala Tyr Ser
                            485                 490                 495

Glu Ile Gly Met Lys Gly Glu Arg Arg Arg Gly Lys Gly His Asp Gly
                        500                 505                 510

Leu Tyr Gln Gly Leu Ser Thr Ala Thr Lys Asp Thr Tyr Asp Ala Leu
                    515                 520                 525

His Met Gln Ala Leu Pro Pro Arg
            530                 535

<210> SEQ ID NO 54
<211> LENGTH: 27
<212> TYPE: DNA
<213> ORGANISM: Artificial sequence
<220> FEATURE:
<223> OTHER INFORMATION: Primer

<400> SEQUENCE: 54
gatcgctagc acagccccg ccgccgc                                         27

<210> SEQ ID NO 55
<211> LENGTH: 31
<212> TYPE: DNA
<213> ORGANISM: Artificial sequence
<220> FEATURE:
<223> OTHER INFORMATION: Primer

<400> SEQUENCE: 55
gtacggatcc ttcagcgggg aatgaacgtt c                                   31

<210> SEQ ID NO 56
<211> LENGTH: 345
<212> TYPE: DNA
<213> ORGANISM: Artificial sequence
```

```
<220> FEATURE:
<223> OTHER INFORMATION: Nucleotide sequence of 5A5 heavy chain

<400> SEQUENCE: 56
caggttcaac tgcagcagtc tgggactgag ctggtgaggc ctggggcttc agtgaagctg      60
tcctgcaagg ctttgggcta cacatttact gactatgaaa tgcactgggt gaagcagaca     120
cctgtgcatg gcctggagtg gattggagct attcatccag gaagtggtga tactgcctac     180
aatcagaggt tcaagggcaa ggccacactg actgcagaca atcttccag cacagcctac      240 atggagtaca gcagcctgac atctgaggac tctgctgtct attactgtac aagattttat     300
tcctatgctt actggggcca aggactctg gtcactgtct ctgca                      345

<210> SEQ ID NO 57
<211> LENGTH: 339
<212> TYPE: DNA
<213> ORGANISM: Artificial sequence
<220> FEATURE:
<223> OTHER INFORMATION: Nucleotide sequence of 5A5 light chain

<400> SEQUENCE: 57
gatgttgtga tgacccaaac tccactctcc ctgcctgtca gtcttggaga tcaagcctcc      60
atctcttgca gatctagtca gagccttgta cacagtaatg gaaacaccta tttacagtgg     120
tacctgcaga agccaggcca gtctccaaag ctcctgatct acaaagtttc caatcgattt     180
tctggggtcc cagacaggtt cagtggcaga ggatcaggga cagatttcac actcaagatc     240
agcagagtgg aggctgagga tctgggagtt tatttctgct ctcaaagtat atatgttccg     300
tacacgttcg gaggagggac caagctggaa ataaaacgg                            339

<210> SEQ ID NO 58
<211> LENGTH: 115
<212> TYPE: PRT
<213> ORGANISM: Artificial sequence
<220> FEATURE:
<223> OTHER INFORMATION: Nucleotide sequence of humanized Y035 heavy
      chain

<400> SEQUENCE: 58

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asp Tyr
            20                  25                  30

Glu Met His Trp Val Arg Gln Ala Pro Gly Gln Gly Leu Glu Trp Met
        35                  40                  45

Gly Ala Ile His Pro Gly Ser Gly Asp Thr Ala Tyr Asn Gln Arg Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Phe Tyr Ser Tyr Ala Tyr Trp Gly Gln Gly Thr Leu Val Thr
            100                 105                 110

Val Ser Ala
        115

<210> SEQ ID NO 59
<211> LENGTH: 113
<212> TYPE: PRT
<213> ORGANISM: Artificial sequence
```

<220> FEATURE:
<223> OTHER INFORMATION: amino acid sequence of humanized Y035 light
      chain

<400> SEQUENCE: 59

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asn Thr Tyr Leu Gln Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Ile Tyr Val Pro Tyr Thr Phe Gly Gln Gly Thr Lys Leu Glu Ile Lys
            100                 105                 110

Arg

<210> SEQ ID NO 60
<211> LENGTH: 10
<212> TYPE: PRT
<213> ORGANISM: Artificial sequence
<220> FEATURE:
<223> OTHER INFORMATION: amino acid sequence of am4 heavy chain CDR1

<400> SEQUENCE: 60

Gly Phe Thr Phe Ser Thr Tyr Ala Met Thr
1               5                   10

<210> SEQ ID NO 61
<211> LENGTH: 17
<212> TYPE: PRT
<213> ORGANISM: Artificial sequence
<220> FEATURE:
<223> OTHER INFORMATION: amino acid sequence of am4 heavy chain CDR2

<400> SEQUENCE: 61

Ser Ile Ser Ser Ser Gly Glu Ser Thr Tyr Tyr Ala Asp Ser Val Lys
1               5                   10                  15

Gly

<210> SEQ ID NO 62
<211> LENGTH: 10
<212> TYPE: PRT
<213> ORGANISM: Artificial sequence
<220> FEATURE:
<223> OTHER INFORMATION: amino acid sequence of am14 heavy chain CDR1

<400> SEQUENCE: 62

Gly Phe Thr Phe Ser Thr Tyr Ala Met Ala
1               5                   10

<210> SEQ ID NO 63
<211> LENGTH: 17
<212> TYPE: PRT
<213> ORGANISM: Artificial sequence
<220> FEATURE:
<223> OTHER INFORMATION: amino acid sequence of am14 heavy chain CDR2

<400> SEQUENCE: 63

```
Glu Ile Ser Ser Ser Gly Ser Arg Thr Tyr Tyr Ala Asp Ser Val Lys
1               5                   10                  15

Gly

<210> SEQ ID NO 64
<211> LENGTH: 10
<212> TYPE: PRT
<213> ORGANISM: Artificial sequence
<220> FEATURE:
<223> OTHER INFORMATION: amino acid sequence of am20 heavy chain CDR1

<400> SEQUENCE: 64

Gly Phe Thr Phe Ser Thr Tyr Ala Met Ala
1               5                   10

<210> SEQ ID NO 65
<211> LENGTH: 17
<212> TYPE: PRT
<213> ORGANISM: Artificial sequence
<220> FEATURE:
<223> OTHER INFORMATION: amino acid sequence of am20 heavy chain CDR2

<400> SEQUENCE: 65

Ala Ile Ser Met Ser Gly Glu Ser Thr Tyr Tyr Ala Asp Ser Val Lys
1               5                   10                  15

Gly

<210> SEQ ID NO 66
<211> LENGTH: 17
<212> TYPE: PRT
<213> ORGANISM: Artificial sequence
<220> FEATURE:
<223> OTHER INFORMATION: amino acid sequence of am35 heavy chain CDR2

<400> SEQUENCE: 66

Ala Ile Ser Ser Ser Gly Gly Ser Thr Tyr Tyr Ala Asp Ser Val Lys
1               5                   10                  15

Gly

<210> SEQ ID NO 67
<211> LENGTH: 14
<212> TYPE: PRT
<213> ORGANISM: Artificial sequence
<220> FEATURE:
<223> OTHER INFORMATION: amino acid sequence of am35 light chain CDR1

<400> SEQUENCE: 67

Thr Gly Thr Ser Ser Asp Val Gly His Lys Phe Pro Val Ser
1               5                   10

<210> SEQ ID NO 68
<211> LENGTH: 7
<212> TYPE: PRT
<213> ORGANISM: Artificial sequence
<220> FEATURE:
<223> OTHER INFORMATION: amino acid sequence of am35 light chain CDR2

<400> SEQUENCE: 68

Lys Asn Leu Leu Arg Pro Ser
1               5

<210> SEQ ID NO 69
<211> LENGTH: 14
<212> TYPE: PRT
```

```
<213> ORGANISM: Artificial sequence
<220> FEATURE:
<223> OTHER INFORMATION: amino acid sequence of am42 light chain CDR1

<400> SEQUENCE: 69

Thr Gly Thr Ser Ser Asp Val Gly Leu Met His Asn Val Ser
1               5                   10

<210> SEQ ID NO 70
<211> LENGTH: 7
<212> TYPE: PRT
<213> ORGANISM: Artificial sequence
<220> FEATURE:
<223> OTHER INFORMATION: amino acid sequence of am42 light chain CDR2

<400> SEQUENCE: 70

Lys Ser Ser Arg Pro Ser
1               5

<210> SEQ ID NO 71
<211> LENGTH: 17
<212> TYPE: PRT
<213> ORGANISM: Artificial sequence
<220> FEATURE:
<223> OTHER INFORMATION: amino acid sequence of T2-23 heavy chain CDR2

<400> SEQUENCE: 71

Ala Ile Ser Ser Ser Gly Arg Ser Thr Tyr Tyr Ala Asp Ser Val Glu
1               5                   10                  15

Gly

<210> SEQ ID NO 72
<211> LENGTH: 12
<212> TYPE: PRT
<213> ORGANISM: Artificial sequence
<220> FEATURE:
<223> OTHER INFORMATION: amino acid sequence of T2-23 heavy chain CDR3

<400> SEQUENCE: 72

Asp Arg Arg Gly Ser His Ala Asp Ala Leu Asn Val
1               5                   10

<210> SEQ ID NO 73
<211> LENGTH: 5
<212> TYPE: PRT
<213> ORGANISM: Artificial sequence
<220> FEATURE:
<223> OTHER INFORMATION: amino acid sequence of humanized Y035 heavy
      chain CDR1

<400> SEQUENCE: 73

Asp Tyr Glu Met His
1               5

<210> SEQ ID NO 74
<211> LENGTH: 17
<212> TYPE: PRT
<213> ORGANISM: Artificial sequence
<220> FEATURE:
<223> OTHER INFORMATION: amino acid sequence of humanized Y035 heavy
      chain CDR2

<400> SEQUENCE: 74

Ala Ile His Pro Gly Ser Gly Asp Thr Ala Tyr Asn Gln Arg Phe Lys
1               5                   10                  15

Gly
```

<210> SEQ ID NO 75
<211> LENGTH: 6
<212> TYPE: PRT
<213> ORGANISM: Artificial sequence
<220> FEATURE:
<223> OTHER INFORMATION: amino acid sequence of humanized Y035 heavy
      chain CDR3

<400> SEQUENCE: 75

Phe Tyr Ser Tyr Ala Tyr
1               5

<210> SEQ ID NO 76
<211> LENGTH: 16
<212> TYPE: PRT
<213> ORGANISM: Artificial sequence
<220> FEATURE:
<223> OTHER INFORMATION: amino acid sequence of humanized Y035 light
      chain CDR1

<400> SEQUENCE: 76

Arg Ser Ser Gln Ser Leu Val His Ser Asn Gly Asn Thr Tyr Leu Gln
1               5                   10                  15

<210> SEQ ID NO 77
<211> LENGTH: 7
<212> TYPE: PRT
<213> ORGANISM: Artificial sequence
<220> FEATURE:
<223> OTHER INFORMATION: amino acid sequence of humanized Y035 light
      chain CDR2

<400> SEQUENCE: 77

Lys Val Ser Asn Arg Phe Ser
1               5

<210> SEQ ID NO 78
<211> LENGTH: 9
<212> TYPE: PRT
<213> ORGANISM: Artificial sequence
<220> FEATURE:
<223> OTHER INFORMATION: amino acid sequence of humanized Y035 light
      chain CDR3

<400> SEQUENCE: 78

Ser Gln Ser Ile Tyr Val Pro Tyr Thr
1               5

<210> SEQ ID NO 79
<211> LENGTH: 429
<212> TYPE: DNA
<213> ORGANISM: Artificial sequence
<220> FEATURE:
<223> OTHER INFORMATION: Nucleotide sequence of humanized antibody Y035
      light chain

<400> SEQUENCE: 79
ggatcgatat ccaccatgga catgatggtg ctggcccagt tcctggcctt cctgctgctg      60
tggttcccag gcgctagatg cgacatcgtg atgacccaga cccccctgag cctgcccgtg     120 accccggcg agcccgccag catcagctgc cggagcagcc agagcctggt gcacagcaac     180
ggcaacacct acctgcagtg gtacctgcag aagcccggcc agagccccca gctgctgatc     240
tacaaggtga gcaaccggtt cagcggcgtg cccgaccggt tcagcggcag cggcagcggc     300
accgacttca ccctgaagat cagccgggtg gaggccgagg acgtgggcgt gtactactgc     360

```
agccagagca tctacgtgcc ctacaccttc ggccagggca ccaagctgga gatcaaacgt      420
acggtggct                                                             429

<210> SEQ ID NO 80
<211> LENGTH: 441
<212> TYPE: DNA
<213> ORGANISM: Artificial sequence
<220> FEATURE:
<223> OTHER INFORMATION: Nucleotide sequence of humanized antibody Y035
      heavy chain

<400> SEQUENCE: 80
ggatcgatat ctgcggccta tctagccacc atgcgggtgc tgatcctgct gtggctgttt      60
accgccttcc ccggcttcct gagcgaggtg cagctggtgc agagcggcgc cgaggtgaag     120
aagcccggcg ccagcgtgaa ggtgagctgc aaggccagcg gctacacctt cagcgactac     180
gagatgcact gggtgcggca ggcccccggc cagggcctgg agtggatggg cgccatccac     240
cccggcagcg gcgacaccgc ctacaaccag cggttcaagg gccgggtgac catcaccgcc     300
gacaagagca ccagcaccgc ctacatggag ctgagcagcc tgcggagcga ggacaccgcc     360
gtgtactact gcgcccggtt ctacagctac gcctactggg gccagggcac cctggtgacc     420
gtgagcgccg ctagcaccaa a                                               441

<210> SEQ ID NO 81
<211> LENGTH: 115
<212> TYPE: PRT
<213> ORGANISM: Artificial sequence
<220> FEATURE:
<223> OTHER INFORMATION: amino acid sequence of 5A5 heavy chain

<400> SEQUENCE: 81

Gln Val Gln Leu Gln Gln Ser Gly Thr Glu Leu Val Arg Pro Gly Ala
1               5                  10                  15

Ser Val Lys Leu Ser Cys Lys Ala Leu Gly Tyr Thr Phe Thr Asp Tyr
            20                  25                  30

Glu Met His Trp Val Lys Gln Thr Pro Val His Gly Leu Glu Trp Ile
        35                  40                  45

Gly Ala Ile His Pro Gly Ser Gly Asp Thr Ala Tyr Asn Gln Arg Phe
    50                  55                  60

Lys Gly Lys Ala Thr Leu Thr Ala Asp Lys Ser Ser Thr Ala Tyr
65                  70                  75                  80

Met Glu Tyr Ser Ser Leu Thr Ser Glu Asp Ser Ala Val Tyr Tyr Cys
                85                  90                  95

Thr Arg Phe Tyr Ser Tyr Ala Tyr Trp Gly Gln Gly Thr Leu Val Thr
            100                 105                 110

Val Ser Ala
        115

<210> SEQ ID NO 82
<211> LENGTH: 113
<212> TYPE: PRT
<213> ORGANISM: Artificial sequence
<220> FEATURE:
<223> OTHER INFORMATION: amino acid sequence of 5A5 light chain

<400> SEQUENCE: 82

Asp Val Val Met Thr Gln Thr Pro Leu Ser Leu Pro Val Ser Leu Gly
1               5                  10                  15
```

```
Asp Gln Ala Ser Ile Ser Cys Arg Ser Ser Gln Ser Leu Val His Ser
            20                  25                  30

Asn Gly Asn Thr Tyr Leu Gln Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Arg Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Ile Tyr Val Pro Tyr Thr Phe Gly Gly Gly Thr Lys Leu Glu Ile Lys
            100                 105                 110

Arg

<210> SEQ ID NO 83
<211> LENGTH: 68
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (42)..(43)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (48)..(49)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t

<400> SEQUENCE: 83
gtttgggggc tttgcctggg tactgttggt accaggagac mnnahmnna hnaccaacgt    60 cactgctg                                                            68

<210> SEQ ID NO 84
<211> LENGTH: 59
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (33)..(34)
<223> OTHER INFORMATION: n is a, c, g, or t
<220> FEATURE:
<221> NAME/KEY: misc_feature
<222> LOCATION: (36)..(37)
<223> OTHER INFORMATION: n is a, c, g, or t
<220> FEATURE:
<221> NAME/KEY: misc_feature
<222> LOCATION: (39)..(40)
<223> OTHER INFORMATION: n is a, c, g, or t
<220> FEATURE:
<221> NAME/KEY: misc_feature
<222> LOCATION: (42)..(43)
<223> OTHER INFORMATION: n is a, c, g, or t

<400> SEQUENCE: 84
acccaggcaa agcccccaaa ctcctcatct atnnknnknn knnkcggccc tcagggtc     59
```

<210> SEQ ID NO 85
<211> LENGTH: 1398
<212> TYPE: DNA
<213> ORGANISM: Artificial sequence
<220> FEATURE:
<223> OTHER INFORMATION: Nucleotide sequence of Y035-BBZ

<400> SEQUENCE: 85

| | |
|---|---|
| gaggtgcagc tggtgcagag cggcgccgag gtgaagaagc ccggcgccag cgtgaaggtg | 60 |
| agctgcaagg ccagcggcta caccttcagc gactacgaga tgcactgggt gcggcaggcc | 120 |
| cccggccagg gcctggagtg gatgggcgcc atccaccccg gcagcggcga caccgcctac | 180 |
| aaccagcggt tcaagggccg ggtgaccatc accgccgaca gagcaccag caccgcctac | 240 |
| atggagctga gcagcctgcg gagcgaggac accgccgtgt actactgcgc ccggttctac | 300 |
| agctacgcct actggggcca gggcaccctg gtgaccgtga gcgccggtgg aggcggttca | 360 |
| ggcggaggtg gttctggcgg tggcggatcg gacatcgtga tgacccagac ccccctgagc | 420 |
| ctgcccgtga cccccggcga gcccgccagc atcagctgcc ggagcagcca gagcctggtg | 480 |
| cacagcaacg gcaacaccta cctgcagtgg tacctgcaga gcccggcca gagcccccag | 540 |
| ctgctgatct acaaggtgag caaccggttc agcggcgtgc ccgaccggtt cagcggcagc | 600 |
| ggcagcggca ccgacttcac cctgaagatc agcccgggtgg aggccgagga cgtgggcgtg | 660 |
| tactactgca gccagagcat ctacgtgccc tacaccttcg gccagggcac caagctggag | 720 |
| atcaaacgta ccacgacgcc agcgccgcga ccaccaacac cggcgccac catcgcgtcg | 780 |
| cagccctgt cctgcgccc agaggcgtgc cggccagcgg cggggggcgc agtgcacacg | 840 |
| agggggctgg acttcgcctg tgatatctac atctgggcgc ccttggccgg acttgtggg | 900 |
| gtccttctcc tgtcactggt tatcaccctt tactgcaaac ggggcagaaa gaaactcctg | 960 |
| tatatattca acaaccatt tatgagacca gtacaaacta ctcaagagga agatggctgt | 1020 |
| agctgccgat ttccagaaga agaagaagga ggatgtgaac tgagagtgaa gttcagcagg | 1080 |
| agcgcagacg ccccgcgta caagcagggc cagaaccagc tctataacga gctcaatcta | 1140 |
| ggacgaagag aggagtacga tgttttggac aagagacgtg gccgggaccc tgagatgggg | 1200 |
| ggaaagccga aaggaagaa ccctcaggaa ggcctgtaca tgaactgca gaaagataag | 1260 |
| atggcggagg cctacagtga gattgggatg aaaggcgagc gccggagggg caaggggcac | 1320 |
| gatggccttt accagggtct cagtacagcc accaaggaca cctacgacgc ccttcacatg | 1380 |
| caggccctgc cccctcgc | 1398 |

<210> SEQ ID NO 86
<211> LENGTH: 466
<212> TYPE: PRT
<213> ORGANISM: Artificial sequence
<220> FEATURE:
<223> OTHER INFORMATION: amino acid sequence of Y035-BBZ

<400> SEQUENCE: 86

Glu Val Gln Leu Val Gln Ser Gly Ala Glu Val Lys Lys Pro Gly Ala
1               5                  10                  15

Ser Val Lys Val Ser Cys Lys Ala Ser Gly Tyr Thr Phe Ser Asp Tyr
            20                  25                  30

Glu Met His Trp Val Arg Gln Ala Pro Gly Gln Gly Leu Glu Trp Met
        35                  40                  45

Gly Ala Ile His Pro Gly Ser Gly Asp Thr Ala Tyr Asn Gln Arg Phe
    50                  55                  60

-continued

```
Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Phe Tyr Ser Tyr Ala Tyr Trp Gly Gln Gly Thr Leu Val Thr
            100                 105                 110

Val Ser Ala Gly Gly Gly Ser Gly Gly Gly Ser Gly Gly Gly
        115                 120                 125

Gly Ser Asp Ile Val Met Thr Gln Thr Pro Leu Ser Leu Pro Val Thr
    130                 135                 140

Pro Gly Glu Pro Ala Ser Ile Ser Cys Arg Ser Ser Gln Ser Leu Val
145                 150                 155                 160

His Ser Asn Gly Asn Thr Tyr Leu Gln Trp Tyr Leu Gln Lys Pro Gly
                165                 170                 175

Gln Ser Pro Gln Leu Leu Ile Tyr Lys Val Ser Asn Arg Phe Ser Gly
            180                 185                 190

Val Pro Asp Arg Phe Ser Gly Ser Gly Thr Asp Phe Thr Leu
            195                 200                 205

Lys Ile Ser Arg Val Glu Ala Glu Asp Val Gly Val Tyr Tyr Cys Ser
    210                 215                 220

Gln Ser Ile Tyr Val Pro Tyr Thr Phe Gly Gln Gly Thr Lys Leu Glu
225                 230                 235                 240

Ile Lys Arg Thr Thr Thr Pro Ala Pro Arg Pro Pro Thr Pro Ala Pro
                245                 250                 255

Thr Ile Ala Ser Gln Pro Leu Ser Leu Arg Pro Glu Ala Cys Arg Pro
            260                 265                 270

Ala Ala Gly Gly Ala Val His Thr Arg Gly Leu Asp Phe Ala Cys Asp
            275                 280                 285

Ile Tyr Ile Trp Ala Pro Leu Ala Gly Thr Cys Gly Val Leu Leu Leu
    290                 295                 300

Ser Leu Val Ile Thr Leu Tyr Cys Lys Arg Gly Arg Lys Lys Leu Leu
305                 310                 315                 320

Tyr Ile Phe Lys Gln Pro Phe Met Arg Pro Val Gln Thr Thr Gln Glu
                325                 330                 335

Glu Asp Gly Cys Ser Cys Arg Phe Pro Glu Glu Glu Gly Gly Cys
            340                 345                 350

Glu Leu Arg Val Lys Phe Ser Arg Ser Ala Asp Ala Pro Ala Tyr Lys
            355                 360                 365

Gln Gly Gln Asn Gln Leu Tyr Asn Glu Leu Asn Leu Gly Arg Arg Glu
    370                 375                 380

Glu Tyr Asp Val Leu Asp Lys Arg Arg Gly Arg Asp Pro Glu Met Gly
385                 390                 395                 400

Gly Lys Pro Arg Arg Lys Asn Pro Gln Glu Gly Leu Tyr Asn Glu Leu
                405                 410                 415

Gln Lys Asp Lys Met Ala Glu Ala Tyr Ser Glu Ile Gly Met Lys Gly
            420                 425                 430

Glu Arg Arg Arg Gly Lys Gly His Asp Gly Leu Tyr Gln Gly Leu Ser
            435                 440                 445

Thr Ala Thr Lys Asp Thr Tyr Asp Ala Leu His Met Gln Ala Leu Pro
    450                 455                 460

Pro Arg
465
```

<210> SEQ ID NO 87
<211> LENGTH: 1407
<212> TYPE: DNA
<213> ORGANISM: Artificial sequence
<220> FEATURE:
<223> OTHER INFORMATION: Nucleotide sequence of Y035-28Z

<400> SEQUENCE: 87

```
gaggtgcagc tggtgcagag cggcgccgag gtgaagaagc ccggcgccag cgtgaaggtg      60
agctgcaagg ccagcggcta caccttcagc gactacgaga tgcactgggt gcggcaggcc     120
cccggccagg gcctggagtg gatgggcgcc atccaccccg gcagcggcga caccgcctac     180
aaccagcggt tcaagggccg ggtgaccatc accgccgaca gagcaccag caccgcctac     240
atggagctga gcagcctgcg gagcgaggac accgccgtgt actactgcgc ccggttctac     300
agctacgcct actggggcca gggcaccctg gtgaccgtga gcgccggtgg aggcggttca     360
ggcggaggtg gttctggcgg tggcggatcg gacatcgtga tgacccagac ccccctgagc     420
ctgcccgtga ccccggcga gcccgccagc atcagctgcc ggagcagcca gagcctggtg     480
cacagcaacg gcaacaccta cctgcagtgg tacctgcaga agcccggcca gagcccccag     540
ctgctgatct acaaggtgag caaccggttc agcggcgtgc ccgaccggtt cagcggcagc     600
ggcagcggca ccgacttcac cctgaagatc agccgggtgg aggccgagga cgtgggcgtg     660
tactactgca gccagagcat ctacgtgccc tacaccttcg gccagggcac caagctggag     720
atcaaacgta ccacgacgcc agcgccgcga ccaccaacac cggcgcccac catcgcgtcg     780
cagccctgt ccctgcgccc agaggcgtgc cggccagcgg cggggggcgc agtgcacacg     840
aggggctgg acttcgcctg tgattttgg gtgctggtgg tggttggtgg agtcctggct     900
tgctatagct tgctagtaac agtggccttt attattttct gggtgaggag taagaggagc     960
aggctcctgc acagtgacta catgaacatg actccccgcc gccccgggcc aacccgcaag    1020
cattaccagc cctatgcccc accacgcgac ttcgcagcct atcgctccag agtgaagttc    1080
agcaggagcg cagacgcccc cgcgtaccag cagggccaga accagctcta taacgagctc    1140
aatctaggac gaagagagga gtacgatgtt ttggacaaga cgtggccg ggaccctgag     1200
atgggggaa agccgcagag aaggaagaac cctcaggaag gcctgtacaa tgaactgcag    1260
aaagataaga tggcggaggc ctacagtgag attgggatga aggcgagcg ccggaggggc    1320
aagggcacg atggccttta ccagggtctc agtacagcca ccaaggacac ctacgacgcc    1380
cttcacatgc aggccctgcc ccctcgc                                        1407
```

<210> SEQ ID NO 88
<211> LENGTH: 469
<212> TYPE: PRT
<213> ORGANISM: Artificial sequence
<220> FEATURE:
<223> OTHER INFORMATION: amino acid sequence of Y035-28Z

<400> SEQUENCE: 88

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asp Tyr
            20                  25                  30

Glu Met His Trp Val Arg Gln Ala Pro Gly Gln Gly Leu Glu Trp Met
        35                  40                  45

Gly Ala Ile His Pro Gly Ser Gly Asp Thr Ala Tyr Asn Gln Arg Phe
    50                  55                  60
```

-continued

```
Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Phe Tyr Ser Tyr Ala Tyr Trp Gly Gln Gly Thr Leu Val Thr
            100                 105                 110

Val Ser Ala Gly Gly Gly Gly Ser Gly Gly Gly Gly Ser Gly Gly Gly
        115                 120                 125

Gly Ser Asp Ile Val Met Thr Gln Thr Pro Leu Ser Leu Pro Val Thr
    130                 135                 140

Pro Gly Glu Pro Ala Ser Ile Ser Cys Arg Ser Ser Gln Ser Leu Val
145                 150                 155                 160

His Ser Asn Gly Asn Thr Tyr Leu Gln Trp Tyr Leu Gln Lys Pro Gly
                165                 170                 175

Gln Ser Pro Gln Leu Leu Ile Tyr Lys Val Ser Asn Arg Phe Ser Gly
            180                 185                 190

Val Pro Asp Arg Phe Ser Gly Ser Gly Ser Gly Thr Asp Phe Thr Leu
        195                 200                 205

Lys Ile Ser Arg Val Glu Ala Glu Asp Val Gly Val Tyr Tyr Cys Ser
    210                 215                 220

Gln Ser Ile Tyr Val Pro Tyr Thr Phe Gly Gln Gly Thr Lys Leu Glu
225                 230                 235                 240

Ile Lys Arg Thr Thr Thr Pro Ala Pro Arg Pro Pro Thr Pro Ala Pro
                245                 250                 255

Thr Ile Ala Ser Gln Pro Leu Ser Leu Arg Pro Glu Ala Cys Arg Pro
            260                 265                 270

Ala Ala Gly Gly Ala Val His Thr Arg Gly Leu Asp Phe Ala Cys Asp
        275                 280                 285

Phe Trp Val Leu Val Val Gly Gly Val Leu Ala Cys Tyr Ser Leu Leu
    290                 295                 300

Leu Val Thr Val Ala Phe Ile Ile Phe Trp Val Arg Ser Lys Arg Ser
305                 310                 315                 320

Arg Leu Leu His Ser Asp Tyr Met Asn Met Thr Pro Arg Arg Pro Gly
                325                 330                 335

Pro Thr Arg Lys His Tyr Gln Pro Tyr Ala Pro Pro Arg Asp Phe Ala
            340                 345                 350

Ala Tyr Arg Ser Arg Val Lys Phe Ser Arg Ser Ala Asp Ala Pro Ala
        355                 360                 365

Tyr Gln Gln Gly Gln Asn Gln Leu Tyr Asn Glu Leu Asn Leu Gly Arg
    370                 375                 380

Arg Glu Glu Tyr Asp Val Leu Asp Lys Arg Arg Gly Arg Asp Pro Glu
385                 390                 395                 400

Met Gly Gly Lys Pro Gln Arg Arg Lys Asn Pro Gln Glu Gly Leu Tyr
                405                 410                 415

Asn Glu Leu Gln Lys Asp Lys Met Ala Glu Ala Tyr Ser Glu Ile Gly
            420                 425                 430

Met Lys Gly Glu Arg Arg Arg Gly Lys Gly His Asp Gly Leu Tyr Gln
        435                 440                 445

Gly Leu Ser Thr Ala Thr Lys Asp Thr Tyr Asp Ala Leu His Met Gln
    450                 455                 460

Ala Leu Pro Pro Arg
465
```

<210> SEQ ID NO 89
<211> LENGTH: 1533
<212> TYPE: DNA
<213> ORGANISM: Artificial sequence
<220> FEATURE:
<223> OTHER INFORMATION: Nucleotide sequence of Y035-28BBZ

<400> SEQUENCE: 89

| | |
|---|---|
| gaggtgcagc tggtgcagag cggcgccgag gtgaagaagc ccggcgccag cgtgaaggtg | 60 |
| agctgcaagg ccagcggcta caccttcagc gactacgaga tgcactgggt gcggcaggcc | 120 |
| cccggccagg gcctggagtg gatgggcgcc atccaccccg gcagcggcga caccgcctac | 180 |
| aaccagcggt tcaagggccg ggtgaccatc accgccgaca gagcaccag caccgcctac | 240 |
| atggagctga gcagcctgcg gagcgaggac accgccgtgt actactgcgc ccggttctac | 300 |
| agctacgcct actggggcca gggcaccctg gtgaccgtga gcgccggtgg aggcggttca | 360 |
| ggcggaggtg gttctggcgg tggcggatcg acatcgtga tgacccagac ccccctgagc | 420 |
| ctgcccgtga cccccggcga gcccgccagc atcagctgcc ggagcagcca gagcctggtg | 480 |
| cacagcaacg gcaacaccta cctgcagtgg tacctgcaga gcccggcca gagccccag | 540 |
| ctgctgatct acaaggtgag caaccggttc agcggcgtgc ccgaccggtt cagcggcagc | 600 |
| ggcagcggca ccgacttcac cctgaagatc agccgggtgg aggccgagga cgtgggcgtg | 660 |
| tactactgca gccagagcat ctacgtgccc tacaccttcg gccagggcac caagctggag | 720 |
| atcaaacgta ccacgacgcc agcgccgcga ccaccaacac cggcgcccac catcgcgtcg | 780 |
| cagccctgt ccctgcgccc agaggcgtgc cggccagcgg cggggggcgc agtgcacacg | 840 |
| agggggctgg acttcgcctg tgattttgg gtgctggtgg tggttggtgg agtcctggct | 900 |
| tgctatagct tgctagtaac agtggccttt attattttct gggtgaggag taagaggagc | 960 |
| aggctcctgc acagtgacta catgaacatg actccccgcc gccccgggcc aacccgcaag | 1020 |
| cattaccagc cctatgcccc accacgcgac ttcgcagcct atcgctccaa acggggcaga | 1080 |
| aagaaactcc tgtatatatt caaacaacca tttatgagac cagtacaaac tactcaagag | 1140 |
| gaagatggct gtagctgccg atttccagaa gaagaagaag gaggatgtga actgagagtg | 1200 |
| aagttcagca ggagcgcaga cgcccccgcg taccagcagg gccagaacca gctctataac | 1260 |
| gagctcaatc taggacgaag agaggagtac gatgttttgg acaagagacg tggccgggac | 1320 |
| cctgagatgg ggggaaagcc gcagagaagg aagaaccctc aggaaggcct gtacaatgaa | 1380 |
| ctgcagaaag ataagatggc ggaggcctac agtgagattg ggatgaaagg cgagcgccgg | 1440 |
| aggggcaagg ggcacgatgg cctttaccag ggtctcagta cagccaccaa ggacacctac | 1500 |
| gacgcccttc acatgcaggc cctgccccct cgc | 1533 |

<210> SEQ ID NO 90
<211> LENGTH: 511
<212> TYPE: PRT
<213> ORGANISM: Artificial sequence
<220> FEATURE:
<223> OTHER INFORMATION: amino acid sequence of Y035-28BBZ

<400> SEQUENCE: 90

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asp Tyr
            20                  25                  30

Glu Met His Trp Val Arg Gln Ala Pro Gly Gln Gly Leu Glu Trp Met
        35                  40                  45

```
Gly Ala Ile His Pro Gly Ser Gly Asp Thr Ala Tyr Asn Gln Arg Phe
    50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Phe Tyr Ser Tyr Ala Tyr Trp Gly Gln Gly Thr Leu Val Thr
             100                 105                 110

Val Ser Ala Gly Gly Gly Ser Gly Gly Gly Ser Gly Gly Gly
         115                 120                 125

Gly Ser Asp Ile Val Met Thr Gln Thr Pro Leu Ser Leu Pro Val Thr
    130                 135                 140

Pro Gly Glu Pro Ala Ser Ile Ser Cys Arg Ser Ser Gln Ser Leu Val
145                 150                 155                 160

His Ser Asn Gly Asn Thr Tyr Leu Gln Trp Tyr Leu Gln Lys Pro Gly
                165                 170                 175

Gln Ser Pro Gln Leu Leu Ile Tyr Lys Val Ser Asn Arg Phe Ser Gly
            180                 185                 190

Val Pro Asp Arg Phe Ser Gly Ser Gly Ser Gly Thr Asp Phe Thr Leu
        195                 200                 205

Lys Ile Ser Arg Val Glu Ala Glu Asp Val Gly Val Tyr Tyr Cys Ser
    210                 215                 220

Gln Ser Ile Tyr Val Pro Tyr Thr Phe Gly Gln Gly Thr Lys Leu Glu
225                 230                 235                 240

Ile Lys Arg Thr Thr Thr Pro Ala Pro Arg Pro Pro Thr Pro Ala Pro
                245                 250                 255

Thr Ile Ala Ser Gln Pro Leu Ser Leu Arg Pro Glu Ala Cys Arg Pro
            260                 265                 270

Ala Ala Gly Gly Ala Val His Thr Arg Gly Leu Asp Phe Ala Cys Asp
        275                 280                 285

Phe Trp Val Leu Val Val Val Gly Gly Val Leu Ala Cys Tyr Ser Leu
    290                 295                 300

Leu Val Thr Val Ala Phe Ile Ile Phe Trp Val Arg Ser Lys Arg Ser
305                 310                 315                 320

Arg Leu Leu His Ser Asp Tyr Met Asn Met Thr Pro Arg Arg Pro Gly
                325                 330                 335

Pro Thr Arg Lys His Tyr Gln Pro Tyr Ala Pro Pro Arg Asp Phe Ala
            340                 345                 350

Ala Tyr Arg Ser Lys Arg Gly Arg Lys Lys Leu Leu Tyr Ile Phe Lys
        355                 360                 365

Gln Pro Phe Met Arg Pro Val Gln Thr Thr Gln Glu Glu Asp Gly Cys
    370                 375                 380

Ser Cys Arg Phe Pro Glu Glu Glu Glu Gly Gly Cys Glu Leu Arg Val
385                 390                 395                 400

Lys Phe Ser Arg Ser Ala Asp Ala Pro Ala Tyr Gln Gln Gly Gln Asn
                405                 410                 415

Gln Leu Tyr Asn Glu Leu Asn Leu Gly Arg Arg Glu Glu Tyr Asp Val
            420                 425                 430

Leu Asp Lys Arg Arg Gly Arg Asp Pro Glu Met Gly Gly Lys Pro Gln
        435                 440                 445

Arg Arg Lys Asn Pro Gln Glu Gly Leu Tyr Asn Glu Leu Gln Lys Asp
    450                 455                 460
```

Lys Met Ala Glu Ala Tyr Ser Glu Ile Gly Met Lys Gly Glu Arg Arg
465                 470                 475                 480

Arg Gly Lys Gly His Asp Gly Leu Tyr Gln Gly Leu Ser Thr Ala Thr
                485                 490                 495

Lys Asp Thr Tyr Asp Ala Leu His Met Gln Ala Leu Pro Pro Arg
                500                 505                 510

<210> SEQ ID NO 91
<211> LENGTH: 45
<212> TYPE: DNA
<213> ORGANISM: Artificial sequence
<220> FEATURE:
<223> OTHER INFORMATION: Primer

<400> SEQUENCE: 91
tgctttggtt tccaggtgca agatgtgagg tgcagctggt gcaga        45

<210> SEQ ID NO 92
<211> LENGTH: 41
<212> TYPE: DNA
<213> ORGANISM: Artificial sequence
<220> FEATURE:
<223> OTHER INFORMATION: Primer

<400> SEQUENCE: 92
tatcggatcc accacctcca cgtttgatct ccagcttggt g        41

<210> SEQ ID NO 93
<211> LENGTH: 22
<212> TYPE: DNA
<213> ORGANISM: Artificial sequence
<220> FEATURE:
<223> OTHER INFORMATION: Primer

<400> SEQUENCE: 93
gatatcaaac tgcagcagtc ag        22

<210> SEQ ID NO 94
<211> LENGTH: 22
<212> TYPE: DNA
<213> ORGANISM: Artificial sequence
<220> FEATURE:
<223> OTHER INFORMATION: Primer

<400> SEQUENCE: 94
gagagggagt actcaccccca ac        22

<210> SEQ ID NO 95
<211> LENGTH: 22
<212> TYPE: DNA
<213> ORGANISM: Artificial sequence
<220> FEATURE:
<223> OTHER INFORMATION: Primer

<400> SEQUENCE: 95
ggctaactag agaacccact gc        22

<210> SEQ ID NO 96
<211> LENGTH: 25
<212> TYPE: DNA
<213> ORGANISM: Artificial sequence
<220> FEATURE:
<223> OTHER INFORMATION: Primer

<400> SEQUENCE: 96
acatcttgca cctggaaacc aaagc                                          25

<210> SEQ ID NO 97
<211> LENGTH: 1473
<212> TYPE: DNA
<213> ORGANISM: Artificial sequence
<220> FEATURE:
<223> OTHER INFORMATION: encoding sequence of Y035/CD3 bispecific
      antibody

<400> SEQUENCE: 97
gaggtgcagc tggtgcagag cggcgccgag gtgaagaagc ccggcgccag cgtgaaggtg      60
agctgcaagg ccagcggcta caccttcagc gactacgaga tgcactgggt gcggcaggcc     120
cccggccagg gcctggagtg gatgggcgcc atccaccccg gcagcggcga caccgcctac     180
aaccagcggt tcaagggccg ggtgaccatc accgccgaca gagcaccag caccgcctac     240
atggagctga gcagcctgcg gagcgaggac accgccgtgt actactgcgc ccggttctac     300
agctacgcct actggggcca gggcaccctg gtgaccgtga gcgccggtgg aggcggttca     360
ggcggaggtg gttctggcgg tggcggatcg gacatcgtga tgacccagac ccccctgagc     420
ctgcccgtga cccccggcga gcccgccagc atcagctgcc ggagcagcca gagcctggtg     480
cacagcaacg gcaacaccta cctgcagtgg tacctgcaga gcccggcca gagcccccag     540
ctgctgatct acaaggtgag caaccggttc agcggcgtgc ccgaccggtt cagcggcagc     600
ggcagcggca ccgacttcac cctgaagatc agccgggtgg aggccgagga cgtgggcgtg     660
tactactgca gccagagcat ctacgtgccc tacaccttcg gccagggcac caagctggag     720
atcaaacgtg gaggtggtgg atccgatatc aaactgcagc agtcaggggc tgaactggca     780
agacctgggg cctcagtgaa gatgtcctgc aagacttctg gctacacctt tactaggtac     840
acgatgcact gggtaaaaca gaggcctgga cagggtctgg aatggattgg atacattaat     900
cctagccgtg gttatactaa ttacaatcag aagttcaagg acaaggccac attgactaca     960
gacaaatcct ccagcacagc ctacatgcaa ctgagcagcc tgacatctga ggactctgca    1020
gtctattact gtgcaagata ttatgatgat cattactgcc ttgactactg gggccaaggc    1080
accactctca cagtctcctc agtcgaaggt ggaagtggag gttctggtgg aagtggaggt    1140
tcaggtggag tcgacgacat tcagctgacc cagtctccag caatcatgtc tgcatctcca    1200
ggggagaagg tcaccatgac ctgcagagcc agttcaagtg taagttacat gaactggtac    1260
cagcagaagt caggcacctc ccccaaaaga tggatttatg acacatccaa agtggcttct    1320
ggagtccctt atcgcttcag tggcagtggg tctgggacct catactctct cacaatcagc    1380
agcatggagg ctgaagatgc tgccacttat tactgccaac agtggagtag taacccgctc    1440
acgttcggtg ctgggaccaa gctggagctg aaa                                 1473

<210> SEQ ID NO 98
<211> LENGTH: 491
<212> TYPE: PRT
<213> ORGANISM: Artificial sequence
<220> FEATURE:
<223> OTHER INFORMATION: amino acid sequence of Y035/CD3 bispecific
      antibody

<400> SEQUENCE: 98

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asp Tyr
            20                  25                  30

-continued

Glu Met His Trp Val Arg Gln Ala Pro Gly Gln Gly Leu Glu Trp Met
            35                  40                  45
Gly Ala Ile His Pro Gly Ser Gly Asp Thr Ala Tyr Asn Gln Arg Phe
        50                  55                  60
Lys Gly Arg Val Thr Ile Thr Ala Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Phe Tyr Ser Tyr Ala Tyr Trp Gly Gln Gly Thr Leu Val Thr
            100                 105                 110
Val Ser Ala Gly Gly Gly Gly Ser Gly Gly Gly Gly Ser Gly Gly Gly
        115                 120                 125
Gly Ser Asp Ile Val Met Thr Gln Thr Pro Leu Ser Leu Pro Val Thr
    130                 135                 140
Pro Gly Glu Pro Ala Ser Ile Ser Cys Arg Ser Ser Gln Ser Leu Val
145                 150                 155                 160
His Ser Asn Gly Asn Thr Tyr Leu Gln Trp Tyr Leu Gln Lys Pro Gly
                165                 170                 175
Gln Ser Pro Gln Leu Leu Ile Tyr Lys Val Ser Asn Arg Phe Ser Gly
            180                 185                 190
Val Pro Asp Arg Phe Ser Gly Ser Gly Ser Gly Thr Asp Phe Thr Leu
        195                 200                 205
Lys Ile Ser Arg Val Glu Ala Glu Asp Val Gly Val Tyr Tyr Cys Ser
    210                 215                 220
Gln Ser Ile Tyr Val Pro Tyr Thr Phe Gly Gln Gly Thr Lys Leu Glu
225                 230                 235                 240
Ile Lys Arg Gly Gly Gly Gly Ser Asp Ile Lys Leu Gln Gln Ser Gly
                245                 250                 255
Ala Glu Leu Ala Arg Pro Gly Ala Ser Val Lys Met Ser Cys Lys Thr
            260                 265                 270
Ser Gly Tyr Thr Phe Thr Arg Tyr Thr Met His Trp Val Lys Gln Arg
        275                 280                 285
Pro Gly Gln Gly Leu Glu Trp Ile Gly Tyr Ile Asn Pro Ser Arg Gly
    290                 295                 300
Tyr Thr Asn Tyr Asn Gln Lys Phe Lys Asp Lys Ala Thr Leu Thr Thr
305                 310                 315                 320
Asp Lys Ser Ser Ser Thr Ala Tyr Met Gln Leu Ser Ser Leu Thr Ser
                325                 330                 335
Glu Asp Ser Ala Val Tyr Tyr Cys Ala Arg Tyr Tyr Asp Asp His Tyr
            340                 345                 350
Cys Leu Asp Tyr Trp Gly Gln Gly Thr Thr Leu Thr Val Ser Ser Val
        355                 360                 365
Glu Gly Gly Ser Gly Gly Ser Gly Gly Ser Gly Gly Ser Gly Gly Val
    370                 375                 380
Asp Asp Ile Gln Leu Thr Gln Ser Pro Ala Ile Met Ser Ala Ser Pro
385                 390                 395                 400
Gly Glu Lys Val Thr Met Thr Cys Arg Ala Ser Ser Ser Val Ser Tyr
                405                 410                 415
Met Asn Trp Tyr Gln Gln Lys Ser Gly Thr Ser Pro Lys Arg Trp Ile
            420                 425                 430
Tyr Asp Thr Ser Lys Val Ala Ser Gly Val Pro Tyr Arg Phe Ser Gly
        435                 440                 445

```
Ser Gly Ser Gly Thr Ser Tyr Ser Leu Thr Ile Ser Ser Met Glu Ala
        450                 455                 460

Glu Asp Ala Ala Thr Tyr Tyr Cys Gln Gln Trp Ser Ser Asn Pro Leu
465                 470                 475                 480

Thr Phe Gly Ala Gly Thr Lys Leu Glu Leu Lys
                485                 490

<210> SEQ ID NO 99
<211> LENGTH: 5
<212> TYPE: PRT
<213> ORGANISM: Artificial sequence
<220> FEATURE:
<221> NAME/KEY: misc_feature
<223> OTHER INFORMATION: Linker

<400> SEQUENCE: 99

Gly Gly Gly Gly Ser
1               5
```